(12) United States Patent
Hickman et al.

(10) Patent No.: US 7,857,731 B2
(45) Date of Patent: Dec. 28, 2010

(54) MOBILE SYSTEMS AND METHODS FOR HEALTH, EXERCISE AND COMPETITION

(75) Inventors: Paul L. Hickman, Los Altos Hills, CA (US); Michael L. Gough, Ben Lomond, CA (US)

(73) Assignee: Icon IP, Inc., Logan, UT (US)

( * ) Notice: Subject to any disclaimer, the term of this patent is extended or adjusted under 35 U.S.C. 154(b) by 0 days.

(21) Appl. No.: 12/489,031

(22) Filed: Jun. 22, 2009

(65) Prior Publication Data

US 2009/0258758 A1 Oct. 15, 2009

Related U.S. Application Data

(60) Division of application No. 11/150,914, filed on Jun. 13, 2005, now Pat. No. 7,549,947, which is a continuation of application No. 10/045,619, filed on Oct. 19, 2001, now Pat. No. 6,921,351.

(51) Int. Cl.
*A63B 71/00* (2006.01)
(52) U.S. Cl. .................... 482/8; 482/1; 482/9; 482/901
(58) Field of Classification Search ............... 482/1–9, 482/900–902; 434/247
See application file for complete search history.

(56) References Cited

U.S. PATENT DOCUMENTS

| | | |
|---|---|---|
| 3,518,985 A | 7/1970 | Quinton |
| 3,602,502 A | 8/1971 | Hampl |
| 3,802,698 A | 4/1974 | Burian et al. |
| 3,845,756 A | 11/1974 | Olsson |
| 3,903,613 A | 9/1975 | Bisberg |
| 4,020,795 A | 5/1977 | Marks |
| 4,112,928 A | 9/1978 | Putsch |

(Continued)

FOREIGN PATENT DOCUMENTS

CN 1162495 10/1997

(Continued)

OTHER PUBLICATIONS

Supplemental Notice of Allowability dated May 5, 2009, 2 pages, U.S. Appl. No. 11/429,725.

(Continued)

*Primary Examiner*—Glenn Richman
(74) *Attorney, Agent, or Firm*—Workman Nydegger

(57) ABSTRACT

An exercise system includes a local system having an exercise apparatus and an associated local computer, where the local computer controls and monitors the operation and use, respectively, of the exercise apparatus. The system further includes a remote system having a remote computer, and a transmission medium preferably including the Internet that couples the local system to the remote system for data communication between the local system and the remote system. The remote system may receive local system data from the local system concerning the use of the exercise apparatus, and the local system may receive remote system data from the remote system concerning the operation of the exercise apparatus. The local computer preferably controls the operation of the exercise apparatus based upon a modifiable script stored in a read/write memory of the local computer, which can be updated by the remote system. A method for controlling an exercise apparatus includes running a modifiable script on a local computer to control the use and to monitor the operation of an exercise apparatus, and communicating with a remote system, preferably via the Internet, to provide the remote system with data concerning the use of the exercise apparatus. The script is stored in read/write memory of the local computer and remote system data received from the remote system may include at least a portion of a new script to be stored in the read/write memory of the local computer.

20 Claims, 32 Drawing Sheets

U.S. PATENT DOCUMENTS

| | | | |
|---|---|---|---|
| 4,151,988 A | 5/1979 | Nabinger | |
| 4,220,996 A | 9/1980 | Searcy | |
| 4,278,095 A | 7/1981 | Lapeyre | |
| 4,358,105 A | 11/1982 | Sweeney | |
| 4,408,613 A | 10/1983 | Relyea | |
| 4,504,055 A | 3/1985 | Wells | |
| 4,542,897 A | 9/1985 | Melton et al. | |
| 4,544,152 A | 10/1985 | Taitel | |
| 4,549,044 A | 10/1985 | Durham | |
| 4,556,216 A | 12/1985 | Pitkanen | |
| 4,571,682 A | 2/1986 | Silverman et al. | |
| 4,642,769 A | 2/1987 | Petrofsky | |
| 4,659,074 A | 4/1987 | Taitel et al. | |
| 4,687,195 A | 8/1987 | Potts | |
| 4,702,475 A | 10/1987 | Elstein et al. | |
| 4,708,337 A | 11/1987 | Shyu | |
| 4,708,837 A | 11/1987 | Baxter et al. | |
| 4,709,917 A | 12/1987 | Yang | |
| 4,757,495 A | 7/1988 | Decker et al. | |
| 4,763,284 A | 8/1988 | Carlin | |
| 4,765,613 A | 8/1988 | Voris | |
| 4,786,049 A | 11/1988 | Lautenschlager | |
| 4,818,234 A | 4/1989 | Redington et al. | |
| 4,828,257 A | 5/1989 | Dyer et al. | |
| 4,837,157 A | 6/1989 | Turnell et al. | |
| 4,842,266 A | 6/1989 | Sweeney, Sr. et al. | |
| 4,842,274 A | 6/1989 | Oosthuizen et al. | |
| 4,848,737 A | 7/1989 | Ehrenfield | |
| 4,860,763 A | 8/1989 | Schminke | |
| 4,866,704 A | 9/1989 | Bergman | |
| 4,889,108 A | 12/1989 | Bond et al. | |
| 4,919,418 A | 4/1990 | Miller | |
| 4,925,183 A | 5/1990 | Kim | |
| 4,925,189 A | 5/1990 | Braeunig | |
| 4,927,136 A | 5/1990 | Leask | |
| 4,934,694 A | 6/1990 | McIntosh | |
| 4,938,474 A | 7/1990 | Sweeney et al. | |
| 4,949,993 A | 8/1990 | Stark et al. | |
| 4,959,713 A | 9/1990 | Morotomi et al. | |
| 4,998,725 A | 3/1991 | Watterson et al. | |
| 5,020,795 A | 6/1991 | Airy et al. | |
| 5,054,774 A | 10/1991 | Belsito | |
| 5,062,632 A | 11/1991 | Dalebout et al. | |
| 5,067,710 A | 11/1991 | Watterson et al. | |
| 5,078,152 A | 1/1992 | Bond et al. | |
| 5,086,385 A | 2/1992 | Launey et al. | |
| 5,089,960 A | 2/1992 | Sweeney, Jr. | |
| 5,104,120 A | 4/1992 | Watterson et al. | |
| 5,113,427 A | 5/1992 | Ryoichi et al. | |
| 5,137,501 A | 8/1992 | Mertesdorf | |
| 5,145,475 A | 9/1992 | Cares | |
| 5,149,084 A | 9/1992 | Dalebout et al. | |
| 5,180,347 A | 1/1993 | Chen | |
| 5,195,935 A | 3/1993 | Fencel | |
| 5,201,772 A | 4/1993 | Maxwell | |
| 5,213,555 A | 5/1993 | Hood et al. | |
| 5,230,673 A | 7/1993 | Maeyama et al. | |
| 5,240,417 A | 8/1993 | Smithson et al. | |
| 5,243,998 A | 9/1993 | Silverman et al. | |
| 5,254,066 A | 10/1993 | Brown et al. | |
| 5,256,115 A | 10/1993 | Scholder et al. | |
| 5,277,678 A | 1/1994 | Friedebach et al. | |
| 5,290,205 A | 3/1994 | Densmore et al. | |
| 5,292,293 A | 3/1994 | Schumacher | |
| 5,299,810 A | 4/1994 | Pierce et al. | |
| 5,308,296 A | 5/1994 | Eckstein | |
| 5,308,300 A | 5/1994 | Chino et al. | |
| 5,313,942 A | 5/1994 | Platzker | |
| 5,314,391 A | 5/1994 | Potash et al. | |
| 5,318,487 A | 6/1994 | Golen et al. | |
| 5,318,491 A | 6/1994 | Houston | |
| D348,493 S | 7/1994 | Ashby | |
| 5,328,420 A | 7/1994 | Allen | |
| 5,328,422 A | 7/1994 | Nichols | |
| 5,335,188 A | 8/1994 | Brisson | |
| 5,352,166 A | 10/1994 | Chang | |
| 5,361,091 A | 11/1994 | Hoarty et al. | |
| 5,375,068 A | 12/1994 | Palmer et al. | |
| 5,382,209 A | 1/1995 | Pasier et al. | |
| 5,385,519 A | 1/1995 | Hsu et al. | |
| 5,385,520 A | 1/1995 | Lepine et al. | |
| 5,387,164 A | 2/1995 | Brown, Jr. | |
| 5,403,252 A | 4/1995 | Leon et al. | |
| 5,407,402 A | 4/1995 | Brown et al. | |
| 5,410,471 A | 4/1995 | Alyfuku et al. | |
| 5,410,472 A | 4/1995 | Anderson | |
| 5,433,679 A | 7/1995 | Szymczak et al. | |
| 5,435,799 A | 7/1995 | Lundin | |
| 5,451,922 A | 9/1995 | Hamilton | |
| 5,462,051 A | 10/1995 | Oka et al. | |
| 5,462,503 A | 10/1995 | Benjamin et al. | |
| 5,462,504 A | 10/1995 | Trulaske et al. | |
| 5,466,200 A | 11/1995 | Ulrich et al. | |
| 5,474,090 A | 12/1995 | Begun et al. | |
| 5,484,389 A | 1/1996 | Stark et al. | |
| 5,489,249 A | 2/1996 | Brewer et al. | |
| 5,512,025 A | 4/1996 | Dalebout et al. | |
| 5,527,239 A | 6/1996 | Abbondanza | |
| 5,535,664 A | 7/1996 | Rokowski | |
| 5,538,486 A | 7/1996 | France et al. | |
| 5,546,324 A | 8/1996 | Palmer et al. | |
| 5,547,439 A | 8/1996 | Rawls et al. | |
| 5,572,643 A | 11/1996 | Judson | |
| 5,577,981 A | 11/1996 | Jarvik | |
| 5,584,779 A | 12/1996 | Knecht et al. | |
| 5,590,128 A | 12/1996 | Maloney et al. | |
| 5,591,104 A | 1/1997 | Andrus et al. | |
| 5,598,849 A | 2/1997 | Browne | |
| 5,600,310 A | 2/1997 | Whipple, III et al. | |
| 5,605,336 A | 2/1997 | Gaoiran et al. | |
| 5,619,412 A | 4/1997 | Hapka | |
| 5,619,991 A | 4/1997 | Sloane | |
| 5,626,539 A | 5/1997 | Piaget et al. | |
| 5,645,509 A | 7/1997 | Brewer et al. | |
| 5,645,513 A | 7/1997 | Haydocy et al. | |
| 5,655,997 A | 8/1997 | Greenberg et al. | |
| 5,663,951 A | 9/1997 | Danneels et al. | |
| 5,667,459 A | 9/1997 | Su | |
| 5,690,582 A | 11/1997 | Ulrich et al. | |
| 5,690,852 A | 11/1997 | Saito et al. | |
| 5,695,400 A | 12/1997 | Fennell, Jr. et al. | |
| 5,697,834 A | 12/1997 | Heumann et al. | |
| 5,702,323 A | 12/1997 | Poulton | |
| 5,704,875 A | 1/1998 | Tanabe | |
| 5,713,794 A | 2/1998 | Shimojima et al. | |
| 5,720,771 A | 2/1998 | Snell | |
| 5,722,418 A | 3/1998 | Bro | |
| 5,738,612 A | 4/1998 | Tsuda | |
| 5,743,833 A | 4/1998 | Watterson et al. | |
| 5,749,372 A | 5/1998 | Allen et al. | |
| 5,752,883 A | 5/1998 | Butcher et al. | |
| 5,752,897 A | 5/1998 | Skowronski et al. | |
| 5,754,765 A | 5/1998 | Danneels et al. | |
| 5,759,199 A | 6/1998 | Snell et al. | |
| 5,771,354 A | 6/1998 | Crawford | |
| 5,777,678 A | 7/1998 | Ogata et al. | |
| 5,779,596 A | 7/1998 | Weber | |
| 5,785,630 A | 7/1998 | Bobick et al. | |
| 5,785,631 A | 7/1998 | Heidecke | |
| 5,810,696 A | 9/1998 | Webb | |
| 5,813,864 A | 9/1998 | Ikuta | |
| 5,836,770 A | 11/1998 | Powers | |
| 5,838,906 A | 11/1998 | Doyle et al. | |
| 5,845,230 A | 12/1998 | Lamberson | |

| Patent No. | Date | Inventor |
|---|---|---|
| 5,854,833 A | 12/1998 | Hogan et al. |
| 5,857,939 A | 1/1999 | Kaufman |
| 5,865,733 A | 2/1999 | Malinouskas et al. |
| 5,873,369 A | 2/1999 | Laniado et al. |
| 5,880,677 A | 3/1999 | Lestician |
| 5,888,172 A | 3/1999 | Andrus et al. |
| 5,890,906 A | 4/1999 | Macri et al. |
| 5,890,995 A | 4/1999 | Bobick et al. |
| 5,905,442 A | 5/1999 | Mosebrook et al. |
| 5,909,544 A | 6/1999 | Anderson, II et al. |
| 5,910,070 A | 6/1999 | Henry et al. |
| 5,911,132 A | 6/1999 | Sloane |
| 5,911,687 A | 6/1999 | Sato et al. |
| 5,916,063 A | 6/1999 | Alessandri |
| 5,917,405 A | 6/1999 | Joao |
| 5,929,748 A | 7/1999 | Odinak |
| 5,929,782 A | 7/1999 | Stark |
| 5,931,763 A | 8/1999 | Alessandri |
| 5,947,869 A | 9/1999 | Shea |
| 5,956,509 A | 9/1999 | Kevner |
| 5,961,561 A | 10/1999 | Wakefield, II |
| 5,964,701 A | 10/1999 | Asada et al. |
| 5,967,975 A | 10/1999 | Ridgeway |
| 5,993,356 A | 11/1999 | Houston et al. |
| 5,995,868 A | 11/1999 | Dorfmeister et al. |
| 5,997,476 A | 12/1999 | Brown |
| 6,004,243 A | 12/1999 | Ewert |
| 6,010,451 A | 1/2000 | Clawson |
| 6,013,007 A | 1/2000 | Root et al. |
| 6,014,432 A | 1/2000 | Modney |
| 6,022,272 A | 2/2000 | Sano |
| 6,033,344 A | 3/2000 | Trulaske et al. |
| 6,042,519 A | 3/2000 | Shea |
| 6,050,822 A | 4/2000 | Faughn |
| 6,050,924 A | 4/2000 | Shea |
| 6,050,942 A | 4/2000 | Rust et al. |
| 6,053,737 A | 4/2000 | Babbitt et al. |
| 6,053,844 A | 4/2000 | Clem |
| 6,059,692 A | 5/2000 | Hickman |
| 6,066,075 A | 5/2000 | Poulton |
| 6,066,705 A | 5/2000 | Calderon et al. |
| 6,106,297 A | 8/2000 | Pollak et al. |
| 6,110,076 A | 8/2000 | Hurt |
| 6,132,337 A | 10/2000 | Krupka et al. |
| 6,148,262 A | 11/2000 | Fry |
| 6,152,854 A | 11/2000 | Carmein |
| 6,152,856 A | 11/2000 | Studor et al. |
| 6,162,151 A | 12/2000 | Tani et al. |
| 6,162,189 A | 12/2000 | Girone et al. |
| 6,171,186 B1 | 1/2001 | Kurosawa et al. |
| 6,171,218 B1 | 1/2001 | Shea |
| 6,193,631 B1 | 2/2001 | Hickman |
| 6,211,451 B1 | 4/2001 | Tohgi et al. |
| 6,231,481 B1 | 5/2001 | Brock |
| 6,231,482 B1 | 5/2001 | Thompson |
| 6,241,524 B1 | 6/2001 | Aoshima et al. |
| 6,244,987 B1 | 6/2001 | Ohsuga et al. |
| 6,244,988 B1 | 6/2001 | Delman |
| 6,251,048 B1 | 6/2001 | Kaufman |
| 6,283,896 B1 | 9/2001 | Grunfeld et al. |
| 6,312,363 B1 | 11/2001 | Watterson et al. |
| 6,322,451 B1 | 11/2001 | Miura |
| 6,356,856 B1 | 3/2002 | Damen et al. |
| 6,358,187 B1 | 3/2002 | Smith |
| 6,371,850 B1 | 4/2002 | Sonoda |
| 6,402,558 B1 | 6/2002 | Hung-Ju et al. |
| 6,450,922 B1 | 9/2002 | Henderson et al. |
| 6,458,060 B1 | 10/2002 | Watterson et al. |
| 6,463,385 B1 | 10/2002 | Fry |
| 6,464,618 B1 | 10/2002 | Shea |
| 6,475,115 B1 | 11/2002 | Candito et al. |
| 6,497,638 B1 | 12/2002 | Shea |
| 6,503,173 B2 | 1/2003 | Clem |
| 6,582,342 B2 | 6/2003 | Kaufman et al. |
| 6,585,622 B1 | 7/2003 | Shum et al. |
| 6,601,016 B1 | 7/2003 | Brown et al. |
| 6,605,020 B1 | 8/2003 | Huang |
| 6,605,038 B1 | 8/2003 | Teller et al. |
| 6,612,492 B1 | 9/2003 | Yen |
| 6,616,578 B2 | 9/2003 | Alessandri |
| 6,626,799 B2 | 9/2003 | Watterson et al. |
| 6,634,992 B2 | 10/2003 | Ogawa |
| 6,638,198 B1 | 10/2003 | Shea |
| 6,645,124 B1 | 11/2003 | Clem |
| 6,648,798 B2 | 11/2003 | Yoo |
| 6,648,802 B2 | 11/2003 | Ware |
| 6,659,916 B1 | 12/2003 | Shea |
| 6,659,946 B1 | 12/2003 | Batchelor et al. |
| 6,669,600 B2 | 12/2003 | Warner |
| 6,687,535 B2 | 2/2004 | Hautala et al. |
| 6,689,057 B1 | 2/2004 | Shinsel et al. |
| 6,700,788 B2 | 3/2004 | Matsushita et al. |
| 6,702,719 B1 | 3/2004 | Brown et al. |
| 6,712,737 B1 | 3/2004 | Nusbaum |
| 6,736,759 B1 | 5/2004 | Stubbs et al. |
| 6,740,007 B2 | 5/2004 | Gordon et al. |
| 6,749,537 B1 | 6/2004 | Hickman |
| 6,783,482 B2 | 8/2004 | Oglesby et al. |
| 6,786,848 B2 | 9/2004 | Yamashita et al. |
| 6,790,178 B1 | 9/2004 | Mault et al. |
| 6,793,607 B2 | 9/2004 | Neil |
| 6,808,472 B1 | 10/2004 | Hickman |
| 6,808,473 B2 | 10/2004 | Hisano et al. |
| 6,824,502 B1 | 11/2004 | Huang |
| 6,825,876 B1 | 11/2004 | Easwar et al. |
| 6,863,641 B1 | 3/2005 | Brown et al. |
| 6,866,613 B1 | 3/2005 | Brown et al. |
| 6,918,858 B2 | 7/2005 | Watterson et al. |
| 6,921,351 B1 | 7/2005 | Hickman |
| 6,976,624 B2 | 12/2005 | Hsiao |
| 6,991,586 B2 | 1/2006 | Lapcevic |
| 6,997,852 B2 | 2/2006 | Watterson et al. |
| 7,022,047 B2 | 4/2006 | Cohen et al. |
| 7,044,891 B1 | 5/2006 | Rivera |
| 7,056,265 B1 | 6/2006 | Shea |
| 7,060,006 B1 | 6/2006 | Watterson |
| 7,060,008 B2 | 6/2006 | Watterson et al. |
| 7,070,539 B2 | 7/2006 | Brown et al. |
| 7,072,789 B2 | 7/2006 | Vock et al. |
| 7,115,076 B2 | 10/2006 | Oglesby et al. |
| 7,128,693 B2 | 10/2006 | Brown et al. |
| 7,166,062 B1 | 1/2007 | Watterson et al. |
| 7,166,064 B2 | 1/2007 | Watterson et al. |
| 7,254,516 B2 | 8/2007 | Case, Jr. et al. |
| 7,350,787 B2 | 4/2008 | Voss |
| 7,354,380 B2 | 4/2008 | Volpe, Jr. |
| 7,455,622 B2 | 11/2008 | Watterson et al. |
| 7,510,509 B2 | 3/2009 | Hickman |
| 7,537,546 B2 | 5/2009 | Watterson et al. |
| 7,549,947 B2 | 6/2009 | Hickman et al. |
| 7,556,590 B2 | 7/2009 | Watterson et al. |
| 7,575,536 B1 | 8/2009 | Hickman |
| 7,625,315 B2 | 12/2009 | Hickman |
| 7,628,730 B1 | 12/2009 | Watterson et al. |
| 7,637,847 B1 | 12/2009 | Hickman |
| 7,645,212 B2 | 1/2010 | Ashby et al. |
| 7,645,213 B2 | 1/2010 | Watterson et al. |
| 7,713,171 B1 | 5/2010 | Hickman |
| 2002/0042328 A1 | 4/2002 | Yoo |
| 2002/0055422 A1 | 5/2002 | Airmet et al. |
| 2004/0012335 A1 | 1/2004 | Shon et al. |
| 2004/0127335 A1 | 7/2004 | Watterson et al. |
| 2004/0162189 A1 | 8/2004 | Hickman |
| 2005/0233859 A1 | 10/2005 | Takai et al. |
| 2005/0233861 A1 | 10/2005 | Hickman |
| 2005/0261609 A1 | 11/2005 | Collings et al. |

| | | | |
|---|---|---|---|
| 2005/0272564 | A1 | 12/2005 | Pyles et al. |
| 2006/0063645 | A1 | 3/2006 | Chiang |
| 2006/0205566 | A1 | 9/2006 | Watterson et al. |
| 2006/0205569 | A1 | 9/2006 | Watterson et al. |
| 2006/0281603 | A1 | 12/2006 | Hickman |
| 2007/0265138 | A1 | 11/2007 | Ashby |
| 2008/0051256 | A1 | 2/2008 | Ashby et al. |
| 2008/0300110 | A1 | 12/2008 | Smith |
| 2009/0258758 | A1 | 10/2009 | Hickman |
| 2009/0270226 | A1 | 10/2009 | Watterson et al. |
| 2009/0270227 | A1 | 10/2009 | Ashby |

FOREIGN PATENT DOCUMENTS

| | | |
|---|---|---|
| CN | 2449755 | 9/2001 |
| DE | 4100559 | 7/1991 |
| EP | 0199442 | 10/1986 |
| JP | H10-243979 | 9/1998 |
| WO | WO8101507 | 6/1981 |
| WO | WO9417860 | 8/1994 |
| WO | WO9638205 | 12/1996 |
| WO | WO9800204 | 1/1998 |
| WO | WO9832496 | 7/1998 |
| WO | WO 2007/081607 | 7/2007 |

OTHER PUBLICATIONS

Office Action dated Sep. 29, 2009, 6 pages, U.S. Appl. No. 11/315,682.

Notice of Allowance and Fee(s) Due dated Oct. 30, 2009, 4 pages, U.S. Appl. No. 10/856,676.

Notice of Allowance and Fee(s) Due dated Nov. 2, 2009, 4 pages, U.S. Appl. No. 12/276,900.

The Fitlinxx Interactive Fitness NetworkTM, Integrated Fitness Corp., brochure, 1998.

The Fitlinxx Interactive Fitness NetworkTM, The Difference Between Surviving and Thriving May Be As Simple as FitlinxxTM, Integrated Fitness Corp., brochure, 1998.

Forbes Digital Tool: Startups, Sweat.equity, www.forbes.com, Feb. 1998.

Netpulse, Networkingout—Coming Distractions: Netpulse Helps Exercisers Surf the Net at the Gym, Accomplish Several Goals at Once, www.netpulse.com, Apr. 1998.

Netpulse, Instead of having an equipment repair technician traveling oer hill and dale, you may soon have equipment repaired via the internet, www.netpulse.com, Jul. 1998.

Netpulse, Infotech is supposed to make life easier-remember? Here's how to be sure it does., www.netpulse.com, Aug. 1998.

Netpulse, Exercise station connects to the Net, Now you can sweat to the Net, www.netpulse.com, Sep. 1998.

Netpulse, New Fitness Equipment Combines Internet, Sweat, Now you can surf and sweat, www.netpulse.com, Jan. 1999.

Netpulse, Hop In, Log On and Sweat, Netpulse exercise machines are the latest Web feat, www.netpulse.com, Feb. 1999.

Netpulse Club WatchTM, Internet Powered Service, brochure, Apr. 1999.

Netpulse, State of the Art, www.netpulse.com, Feb. 2000.

Netpulse, Netpulse Files for Patents on its Pioneering Technology Inventions and Groundbreaking Business Methods in the Media and Fitness Markets, www.netpulse.com, May 2000.

Little Tony, One on One Video Trainer (for Model No. T1T123040), Jun. 1995 (25 pages).

Men's Journal, Squat.com The Home Gym Goes Online, May 2000 (2 pages).

MSNBC.com, Smart Fitness Section, On A Quest for Fitness—The Latest Workout Gear and Gadgets, Feb. 29, 2000 (6 pages).

Options Manual: Video Track/Track Five/Personal Trainer Plus (Part No. 109917) cited as "Options"), Sep. 1992 (4 pages).

PR Newswire, Turn Your Treadmill Into a Internet Appliance with www.iFIT.com, Oct. 19, 1999 (3 pages).

PRO-FORM 8.0 TXP Manual (for Model No. PF080010) (cited as "8.0 TXP"), Nov. 1991 (16 pages).

The Boston Globe, Living Section, p. F1, Wired Workout Local Gyms, Mar. 11, 2000 (2 pages).

The Herald Journal, People in Business, ICON winds Awards, vol. 91, No. 128, May 7, 2000 (1 page).

US Weekly, p. 71, Work Out Online, Mar. 27, 2000 (2 pages).

Communications of the ACM, vol. 35, No. 6, cited as "Comm of the ACM", Jun. 1992 (10 pages).

Ebsco Publishing, New Home Exercise Equipment: Your Computer?, Jun. 2000 (3 pages).

Fortune Magazine, p. 84, Virtual Workouts—Treadmills Possessed, Apr. 17, 2000 (2 pages).

Good Housekeeping, p. 53, A Run for the Money, Feb. 2000 (2 pages).

IEEE Publication, A Telerobotics Construction Set with Integrated Performance Analysis, 0-8186-7108-Apr. 1995 (IEEE) (cited as "Telerobotic Con."), Apr. 1995 (7 pages).

IEEE Publication, Intelligent Monitoring System for Limited System for Limited Communication Path: Telerobotic Task Execution over Internet, 0-8186-7108-4/95 (IEEE) (cited as "Intelligent"), Apr. 1995 (6 pages).

Lifestyler 10.0 ESP Manual (for Model No. 297052) (cited as "10.0 ESP"), Nov. 1992 (16 pages).

1994 Pro-Form First in Fitness, (1994 Copyright ProForm Products, Inc.), (16 pages).

Consumer Reports, Out of the Rat Race, Onto a Treadmill, Feb. 2000 (5 pages).

Consumer Reports, Out of the Rat Race, Onto a Treadmill at http://www.accessmylibrary.com/coms2/summaryU0286-28004514_ITM, Mar. 5, 2007, 8 pages.

Exergaming, en.wikipedia.org, printed Oct. 1, 2007.

Wired, www.wired.com, issue 2.09, Sep. 1994.

"Defendant's Amended Invalidity Contentions," Case No. 2:05-cv-527, signed by Kirk Harris on Mar. 16, 2007.

"Icon Health & Fitness Inc.'s Supplemental Preliminary Invalidity Contentions," Case No. 2-05-cv-527, signed by Brent A. Hansen on Jun. 23, 2006.

"Icon Health & Fitness Inc.'s Preliminary Invalidity Contentions," Case No. 2-05-cv-527, signed by Brent A. Hansen on Jun. 26, 2006.

"Expert Report of Dr. Brent Nelson Pursuant to Federal Rule of Civil Procedure 26(a)(2)(B)," Mar. 13, 2007.

"Netpulse Brings Free Internet Access to Fitness Centers." Newsbytes.com, http://www.newsbytes.com, Jan. 17, 2000.

"Precor and Netpulse Partner to Create the World's First Internet Powered Elliptical." Netpulse press release, Oct. 1, 2999.

Surf While you Sweat.: ABCNEWS.com, Oct. 27, 1998.

"The Best Products of 1999- Business Week's Top Picks of the Most Innovative Products on the Market." Business Week, Dec. 6, 1999.

Netpulse brocure. "Catch the wwwave," available on information and belief at least as early as Feb. 10, 2000.

Winkler, William J., "Pumping Iron With a Digital Friend," Business Week, Dec. 18, 1995, pp. 78a.

Internet Archive Wayback Machine, archive for www.ifit.com, at http://web.archive,org/web/*/www.ifit.com, Sep. 1, 2003.

iFIT.com "Internet Workouts Control Your Treadmill, Bike, or Elliptical," at http://www.ifit.com, Sep. 1, 2003.

ICON Health and Fitness, Nordictrack C2420 (Model No. NTL 14950), 2004.

ICON Health and Fitness, Nordictrack C2420 (Model No. NTL 14951), 2004.

ICON Health and Fitness, Nordictrack C2420 (Model No. NTL 1495.2), 2004.

ICON Health and Fitness, Nordictrack CX 990 (Model No. NEL 09940), 2003.

ICON Health and Fitness, Nordictrack SL 760 (Model No. NTC 89021), 2004.

ICON Health and Fitness, Nordictrack SL 760 (Model No. NTC 89020), 2004.

ICON Health and Fitness, Nordictrack SL 710 (Model No. NTC 07942), 2004.

ICON Health and Fitness, Nordictrack SL 710 (Model No. NTC 07941), 2004.

ICON Health and Fitness, Nordictrack SL 710 (Model No. NTC 07940), 2003.

ICON Health and Fitness, Nordictrack SL 705 (Model No. NTC 05941), 2004.

ICON Health and Fitness, Nordictrack SL 705 (Model No. NTC 05940), 2004.
ICON Health and Fitness, Nordictrack C2420 Manual preceding Specs, 2004.
ICON Health and Fitness, Pro-Form Personal Trainer Plus, available on information and belief at least as early as Jul. 2006.
ICON Health and Fitness, Screenshots of iFit.com, available on information and belief at least as early as Jul. 2006.
ICON Health and Fitness, iFit.com "Log on. Work out." Brochure, 2000.
ICON Health and Fitness, Website printouts (archived docs), 2000.
ICON Health and Fitness, Pro-Form 600 (Model No. PETL60000), 2000.
ICON Health and Fitness, Reebok ACD1 (Model No. RETL11900), 2000.
ICON Health and Fitness, Reebok RT1000 (Model No. RETL16001), 2001.
ICON Health and Fitness, One-on-One Video Trainer (Model No. TLTL21040), 1995.
IEEE Computer Graphics and Applications- EVAC: A Virtual Environment for Control of Remote Imaging Instrumentation, 1996.
IEEE: Performance Analysis of a Gateway Connecting the Cebus to the ISDN, 1993.
Fitness Equipment: Cardio, 1997.
ICON-CYB 034253-034286 and 034323-034328, containing photographs of various fitness equipment systems, 1989-1996, 40 pages.
Mademoiselle, www.iFIT.com, Mademoiselle, Mar. 2000.
Wired, ICON Health and Fitness Image 10.4Qi, Wired, Apr. 2000.
Cooking Light, Cybertrainers are Watching Your Workout, Cooking Light, Aug. 2000.
Villarosa, A Fitness Industry, With Gadgets Galore, the New York Times, Apr. 25, 2000.
Little, Web Creates Workouts With Virtual Trainers, The Birmingham News, Apr. 10, 2000.
San Francisco Chronicle, Let the Web Help You Get Physical, Mar. 16, 2000.
"Workouts that Work," Consumer Reports, pp. 31-39, available on information and belief at least as early as Jan. 1999, 9 pages.
New Balance Fitness Equipment advertisement, Runners World, Feb. 2006, 1 page.
New Balance Fitness Equipment advertisement (with sport block dumbbell advertisement), Runners World, Mar. 2006, 1 page.
T Series T3/T5 Treadmill Operation Manual, copyright 2001, Life Fitness, 30 pages.
Advertisement, "We Just Made Buying a Trackmaster 100% Easier," Athletic Business, Oct. 1991, 2 pages.
Advertisement, "Trackmaster TM500E Treadmill Features Interactive Controller," Athletic Business, Oct. 1991, 1 page.
Advertisement, "Survival Equipment for the New Age," Athletic Business, Oct. 1991, p. 60.
Advertisement, "Introducing the LifeStep Model 9500-We've Made the Best Even Better," Athletic Business, Sep. 1991, 1 page.
Advertisement, "We Just Made Buying a Trackmaster 100% Easier," Athletic Business, Sep. 1991, 2 pages.
Trackmaster Online: Treadmill Controllers: http://web.archive.org/web/20010124093300/www.trackmastertreadmills.com/contrlr.html, available on information and belief at least as early as Jan. 2001, 1 page.
Transcript of Deposition of Michael Benjamin, taken Apr. 11, 2007, from Cybergym Research, LLC v. Icon Health & Fitness, et al., in the Eastern District of Texas, Marshal Division, Case No. 2:05-cv-527 DF, 33 pages.
Michael Benjamin Computation Book, dated Nov. 2, 1991, 14 pages.
Tectrix Fitness Equipment, VR Bike Owners Manual, Jan. 1995, 19 pages.
Tectrix Fitness Equipment, VR Bike Maintenance and Repair manual, Mar. 1997, 55 pages.
Tectrix Fitness Equipment, Photographs of VR Bike, available on information and belief at least as early as 1994, 13 pages.
Tectrix, Tectrix Fitness Equipment History, Jim Sweeney, Jun. 20, 1996, 4 pages.
Tectrix Fitness Equipment, Are We Having Fun Yet? brochure, 1995, 4 pages.
First For Women, No More Bicycle Boredom, Oct. 3, 1994, 2 pages.
Sports Illustrated, Software for Hardbodies, Sep. 19, 1994, 2 pages.
CYBERGEAR, Inc., CyberGear 1000 brochure, which was available, on information and belief, at least as early as 1994, 2 pages.
National Fitness Trade Journal cover, Fall 1995, 1 page.
Tectrix Fitness Equipment, The Body The Brain The Passion The Will product brochure, circa 1998, 24 pages.
Leisure Management, Going Downhill, Virtually, vol. 14, No. 8, Aug. 1994, 2 pages.
Tectrix Fitness Equipment, Sweeney Town from CyberGear for the Tectrix VRBike brochure, which was available, on information and belief, at least as early as 1994, 2 pages.
"Virtual Treadmill Takes Users Anywhere They Want to Go," http://www.ks1.com/?nid=148&sid=6920538, Jun. 24, 2009, 2 pages.
DVD labeled "iFIT.com Media Coverage News Clips Ver. 3.0," dated Mar. 30, 2000.
DVD Labeled "ICON-CYB001" 881 PDF Files Jun. 12, 2006.
CD-ROM Labeled "Supershow 2000," ICON-CYB 034309 Highlight Video Apr. 20, 2006.
CD-ROM Labeled "Supershow 1998," ICON-CYB 034310 Live Video Streaming from Logan, Utah to Atlanta, Georgia, Feb. 10, 1998.
DVD Labeled "1998 Supershow Web Cast," ICON-CYB 034311 Raw video footage, Jun. 2006.
CD-ROM Labeled "Steve Young Webcast," ICON-CYB 034312, Sales Meeting 2000, Jun. 2006.
DVD labeled "Tectrix VR Bike videos, including: 1) Media Coverage News Clips of Tectrix VR Bike, dated Jun. 15, 1994, 11 minutes, 19 seconds; 2) Video demonstrating use of CyberGEAR exercise bike, which was available, on information and belief, at least as early as 1994, 5 minutes, 39 seconds; and 3) Video demonstrating use of Tectrix VR Bike, which was available, on information and belief, at least as early as 1994, 4 minutes, 43 seconds".
Office Action dated Sep. 11, 2000, 3 pages, U.S. Appl. No. 09/349,608.
Notice of Allowance and Issue Fee Due, date mailed Jul. 25, 2001, 2 pages, U.S. Appl. No. 09/349,608.
Notice of Allowance and Fee(s) Due, date mailed Sep. 20, 2004, 7 pages, U.S. Appl. No. 09/641,627.
Restriction Requirement dated Apr. 29, 2005, 4 pages, U.S. Appl. No. 09/641,627.
Office Action dated Jul. 26, 2005, 4 pages, U.S. Appl. No. 09/641,627.
Notice of Allowance and Fee(s) Due, date mailed Feb. 3, 2006, 4 pages, U.S. Appl. No. 09/641,627.
Notice of Allowance and Fee(s) Due, dated Sep. 1, 2006, 4 pages, U.S. Appl. No. 09/641,627.
Notice of Allowance and Fee(s) Due, dated Aug. 8, 2008, 4 pages, U.S. Appl. No. 11/429,858.
Notice of Allowance and Fee(s) Due, dated Jun. 4, 2008, 8 pages, U.S. Appl. No. 11/429,858.
Restriction Requirement dated Apr. 17, 2007, 5 pages, U.S. Appl. No. 11/429,858.
Office Action dated Aug. 22, 2007, 5 pages, U.S. Appl. No. 11/429,858.
Restriction Requirement dated Feb. 5, 2008, 8 pages, U.S. Appl. No. 11/429,858.
Notice of Allowance and Fees(s) Due dated Jun. 18, 2009, U.S. Appl. No. 12/276,900.
Restriction Requirement dated Sep. 23, 2003, 4 pages, U.S. Appl. No. 09/641,600.
Office Action dated Feb. 11, 2004, 4 pages, U.S. Appl. No. 09/641,600.
Notice of Allowance and Fee(s) Due, date mailed Jun. 2, 2004, 4 pages, U.S. Appl. No. 09/641,600.
Office Action dated Feb. 15, 2005, 7 pages, U.S. Appl. No. 09/641,600.
Notice of Allowance and Fee(s) Due, date mailed Sep. 14, 2005, 4 pages, U.S. Appl. No. 09/641,600.
Office Action dated Dec. 18, 2001, 3 pages, U.S. Appl. No. 09/641,220.
Notice of Allowance and Fee(s) Due, date mailed Jul. 1, 2002, 5 pages, U.S. Appl. No. 09/641,220.

Office Action dated Jun. 29, 2004, 3 pages, U.S. Appl. No. 09/776,410.
Notice of Allowance and Fee(s) Due, date mailed Nov. 12, 2004, 4 pages, U.S. Appl. No. 09/776,410.
Notice of Allowance and Fee(s) Due, date mailed Apr. 18, 2005, 5 pages, U.S. Appl. No. 09/776,410.
Notice of Allowance and Fee(s) Due dated Jul. 10, 2009, 4 pages, U.S. Appl. No. 10/856,676.
Notice of Allowance dated Feb. 12, 2009, 4 pages, U.S. Appl. No. 10/856,676.
Notice of Allowance and Fee(s) Due dated Dec. 30, 2008, 8 pages, U.S. Appl. No. 10/856,676.
Notice of Allowance and Fee(s) Due dated Oct. 2, 2008, 8 pages, U.S. Appl. No. 10/856,676.
Office Action dated May 6, 2008, 7 pages, U.S. Appl. No. 10/856,676.
Restriction Requirement dated Oct. 9, 2007, 5 pages, U.S. Appl. No. 10/856,676.
Office Action dated Jan. 24, 2008, 5 pages, U.S. Appl. No. 10/856,676.
Office Action dated Aug. 14, 2009, 6 pages, U.S. Appl. No. 11/314,133.
Office Action dated Jul. 16, 2009, 8 pages, U.S. Appl. No. 11/315,682.
Restriction Requirement dated Jul. 1, 2003, 4 pages, U.S. Appl. No. 09/947,193.
Office Action dated Oct. 23, 2003, 4 pages, U.S. Appl. No. 09/947,193.
Notice of Allowance and Fee(s) Due, date mailed May 14, 2004, 4 pages, U.S. Appl. No. 09/947,193.
Office Action dated Sep. 15, 2005, 5 pages, U.S. Appl. No. 09/947,193.
Notice of Allowance and Fee(s) Due, date mailed Jan. 26, 2006, 5 pages, U.S. Appl. No. 09/947,193.
Notice of Allowance and Fee(s) Due, date mailed Aug. 16, 2006, 4 pages, U.S. Appl. No. 09/947,193.
Restriction Requirement dated Mar. 26, 2007, 5 pages, U.S. Appl. No. 11/429,725.
Office Action dated Jun. 6, 2007, 5 pages, U.S. Appl. No. 11/429,725.
Restriction Requirement dated Nov. 14, 2007, 5 pages, U.S. Appl. No. 11/429,725.
Final Office Action dated Feb. 28, 2008, 8 pages, U.S. Appl. No. 11/429,725.
Notice of Allowance and Fee(s) Due dated Jun. 4, 2008, 9 pages, U.S. Appl. No. 11/429,725.
Notice of Allowance and Fee(s) Due dated Sep. 8, 2008, 4 pages, U.S. Appl. No. 11/429,725.
Office Action dated Jan. 30, 2009, 2 pages, U.S. Appl. No. 11/429,725.
Restriction Requirement dated Sep. 21, 2004, 4 pages, U.S. Appl. No. 10/106,842.
Office Action dated Nov. 12, 2004, 4 pages, U.S. Appl. No. 10/106,842.
Notice of Allowance and Fee(s) Due, date mailed Mar. 14, 2005, 6 pages, U.S. Appl. No. 10/106,842.
Notice of Allowance and Fee(s) Due, date mailed Mar. 29, 2006, 6 pages., U.S. Appl. No. 11/132,740.
Notice of Allowance and Fee(s) Due, date mailed Jun. 30, 2003, 5 pages, U.S. Appl. No. 09/933,701.
Office Action dated Aug. 22, 2006, 5 pages, U.S. Appl. No. 10/674,911.
Office Action dated Dec. 12, 2006, 7 pages, U.S. Appl. No. 10/674,911.
Office Action dated Jul. 2, 2007, 5 pages, U.S. Appl. No. 10/674,911.
Office Action dated Nov. 28, 2007, 8 pages, U.S. Appl. No. 10/674,911.
Office Action dated Apr. 22, 2008, 10 pages, U.S. Appl. No. 10/674,911.
Office Action dated Aug. 18, 2008, 9 pages, U.S. Appl. No. 10/674,911.
Notice of Allowance and Fee(s) Due, date mailed Jan. 28, 2009, 15 pages, U.S. Appl. No. 10/674,911.
Office Action dated Jun. 27, 2008, 13 pages, U.S. Appl. No. 11/833,070.
Office Action dated Oct. 31, 2008, 23 pages, U.S. Appl. No. 11/833,070.
Office Action dated Jun. 16, 1997, 4 pages, U.S. Appl. No. 08/766,513.
Office Action dated Feb. 17, 1998, 5 pages, U.S. Appl. No. 08/766,513.
Notice of Allowance and Issue Fee Due, date mailed Sep. 22, 1998, 3 pages, U.S. Appl. No. 08/766,513.
Response to Rule 312 Communication, dated Jun. 2, 1999, 2 pages, U.S. Appl. No. 08/766,513.
Office Action dated Dec. 10, 1999, 3 pages, U.S. Appl. No. 09/273,591.
Notice of Allowance and Fee(s) Due, date mailed Jul. 14, 2000, 2 pages, U.S. Appl. No. 09/273,591.
Office Action dated Dec. 18, 2001, 3 pages, U.S. Appl. No. 09/690,701.
Office Action dated Sep. 25, 2002, 4 pages, U.S. Appl. No. 09/690,701.
Final Office Action dated Mar. 26, 2003, 4 pages, U.S. Appl. No. 09/690,701.
Advisory Action dated Jun. 16, 2003, 2 pages, U.S. Appl. No. 09/690,701.
Notice of Allowance and Fee(s) Due, date mailed Nov. 24, 2003, 5 pages, U.S. Appl. No. 09/690,701.
Restriction Requirement dated Dec. 29, 2004, 4 pages, U.S. Appl. No. 10/729,356.
Office Action dated Feb. 16, 2005, 5 pages, U.S. Appl. No. 10/729,356.
Restriction Requirement dated Feb. 21, 2006, 5 pages, U.S. Appl. No. 10/729,356.
Notice of Allowance and Fee(s) Due, date mailed Jun. 13, 2006, 6 pages, U.S. Appl. No. 10/729,356.
Response to Rule 312 Communication, dated Jul. 30, 2007, 2 pages, U.S. Appl. No. 10/729,356.
Office Action dated Jan. 14, 2008, 7 pages, U.S. Appl. No. 10/729,356.
Office Action dated Jul. 01, 2008, 9 pages, U.S. Appl. No. 10/729,356.
Notice of Allowance and Fee(s) Due, date mailed Mar. 19, 2009, 7 pages, U.S. Appl. No. 10/729,356.
Office Action dated Jan. 24, 2005, 4 pages, U.S. Appl. No. 10/773,617.
Notice of Allowance and Fee(s) Due, date mailed Apr. 17, 2006, 4 pages, U.S. Appl. No. 10/773,617.
Notice of Allowance and Fee(s) Due, date mailed Jul. 6, 2006, 4 pages, U.S. Appl. No. 10/773,617.
Office Action dated May 16, 2007, 4 pages, U.S. Appl. No. 10/773,617.
Office Action dated Jan. 24, 2008, 8 pages, U.S. Appl. No. 10/773,617.
Final Office Action dated Apr. 24, 2008, 10 pages, U.S. Appl. No. 10/773,617.
Office Action dated Oct. 16, 2008, 9 pages, U.S. Appl. No. 10/773,617.
Notice of Allowance and Fee(s) Due dated May 29, 2009, 4 pages, U.S. Appl. No. 10/773,617.
Office Action dated Jun. 26, 2008, 4 pages, U.S. Appl. No. 11/440,703.
Notice of Allowance and Fee(s) Due dated Dec. 17, 2008, 8 pages, U.S. Appl. No. 11/440,703.
Office Action dated Jun. 13, 2008, 6 pages, U.S. Appl. No. 11/657,701.
Office Action dated Jan. 6, 2009, 8 pages, U.S. Appl. No. 11/657,701.
Office Action dated Apr. 16, 2009, 7 pages, U.S. Appl. No. 11/657,701.
Office Action dated Sep. 24, 2009, 11 pages, U.S. Appl. No. 11/657,701.
Office Action dated Dec. 18, 2001, 3 pages, U.S. Appl. No. 09/690,178.
Notice of Allowance and Fee(s) Due, date mailed Sep. 23, 2002, 5 pages, U.S. Appl. No. 09/690,178.

Office Action dated Mar. 7, 2003, 4 pages, U.S. Appl. No. 09/690,178.
Notice of Allowance and Fee(s) Due, date mailed Nov. 24, 2003, 4 pages, U.S. Appl. No. 09/690,178.
Response to Rule 312 Communication, dated Jan. 21, 2004, 2 pages, U.S. Appl. No. 09/690,178.
Office Action dated Jan. 27, 2005, 6 pages, U.S. Appl. No. 10/751,334.
Final Office Action dated Aug. 25, 2005, 6 pages, U.S. Appl. No. 10/751,334.
Notice of Allowance and Fee(s) Due, date mailed Jun. 12, 2006, 4 pages, U.S. Appl. No. 10/751,334.
Restriction Requirement dated Apr. 17, 2007, 5 pages, U.S. Appl. No. 10/751,334.
Restriction Requirement dated Aug. 9, 2007, 5 pages, U.S. Appl. No. 10/751,334.
Office Action dated Jan. 25, 2008, 7 pages, U.S. Appl. No. 10/751,334.
Office Action dated Jun. 2, 2008, 7 pages U.S. Appl. No. 10/751,334.
Office Action dated Nov. 25, 2008, 6 pages U.S. Appl. No. 10/751,334.
Notice of Allowance and Fee(s) Due dated Jun. 1, 2009, 7 pages, Office Action dated Jun. 1, 2008, 7 pages U.S. Appl. No. 10/751,334.
Office Action dated Jun. 15, 2004, 4 pages, U.S. Appl. No. 10/045,619.
Notice of Allowance and Fee(s) Due, date mailed Mar. 14, 2005, 4 pages, U.S. Appl. No. 10/045,619.
Restriction Requirement dated Jul. 27, 2006, 5 pages, U.S. Appl. No. 11/150,914.
Restriction Requirement dated Oct. 18, 2006, 5 pages, U.S. Appl. No. 11/150,914.
Office Action dated Feb. 22, 2007, 6 pages, U.S. Appl. No. 11/150,914.
Final Office Action dated Dec. 12, 2007, 8 pages, U.S. Appl. No. 11/150,914.
Advisory Action dated Feb. 7, 2008, 3 pages, U.S. Appl. No. 11/150,914.
Office Action dated Apr. 28, 2008, 6 pages, U.S. Appl. No. 11/150,914.
Office Action dated Dec. 31, 2008, 7 pages, U.S. Appl. No. 11/150,914.
Notice of Allowance and Fee(s) Due, date mailed Apr. 15, 2009, 5 pages, U.S. Appl. No. 11/150,914.
Office Action dated Aug. 18, 2008, 6 pages, U.S. Appl. No. 11/150,914.
Office Action dated May 1, 2008, 4 pages, U.S. Appl. No. 11/849,068.
Office Action dated Aug. 21, 2008, 6 pages, U.S. Appl. No. 11/849,068.
Office Action dated Apr. 16, 2009, 7 pages, U.S. Appl. No. 11/849,068.
Office Action dated Dec. 10, 2008, 6 pages, U.S. Appl. No. 11/849,068.
Notice of Allowance and Fee(s) Due dated Feb. 19, 2010, 27 pages, U.S. Appl. No. 11/314,133.
Notice of Allowance and Fee(s) Due dated Feb. 19, 2010, 4 pages, U.S. Appl. No. 11/315,682.
Supplemental Notice of Allowability, dated Apr. 21, 2010, 2 pages, U.S. Appl. No. 11/315,682.
Non-Final Office Action dated Feb. 22, 2010, 5 pages, U.S. Appl. No. 12/467,776.
Notice of Allowance and Fee(s) Due dated Feb. 12, 2010, 8 pages, U.S. Appl. No. 11/657,701.
Final Office Action dated Mar. 12, 2010, 7 pages, U.S. Appl. No. 11/849,068.
Notification of the First Office Action issued on Jun. 12, 2009 by the State Intellectual Property Office of the People's Republic of China for Chinese Patent Application No. 200680048743.X, which was nationalized from and claims priority to PCT Publication No. WO 2007/081607, 19 pages (including original Chinese version and English translation.
Text of the Response to First Office Action and Amended Claims for the first Office Action, submitted Oct. 26, 2009 to the State Intellectual Property Office of the People's Republic of China for Chinese Patent Application No. 200680048743.X, which was nationalized from and claims priority to PCT Publication No. WO 2007/081607, 17 pages (including original Chinese version and English translation).
Notification of the Second Office Action issued on Dec. 25, 2009 by the State Intellectual Property Office of the People's Republic of China for Chinese Patent Application No. 200680048743.X, which was nationalized from and claims priority to PCT Publication No. WO 2007/081607, 10 pages (including original Chinese version and English translation).
Notice of Allowance and Fees Due, 4 pages, U.S. Appl. No. 11/314,133, mailed May 10, 2010.
Notice of Allowance and Fees Due, 4 pages, U.S. Appl. No. 11/315,682, mailed May 13, 2010.
Notice of Allowance and Fees Due, 4 pages, U.S. Appl. No. 12/467,776, mailed Jun. 7, 2010.

SUNDAY
- NO EXERCISE

MONDAY
- 10 MINUTES CYCLING
- 232 CALORIES
- 6 MINUTES AT 80% HEARTRATE
- 1.8 MILES
- DIFFICULTY 6
- 10 MINUTES WEIGHTS
- 172 CALORIES
- 20 REPS @ 100 LBS.
- 20 REPS @ 80 LBS.

TUESDAY
ETC.

MOBILE SYSTEMS AND METHODS FOR HEALTH, EXERCISE AND COMPETITION

CROSS-REFERENCE TO RELATED APPLICATIONS

This application is a divisional application of U.S. patent application Ser. No. 11/150,914, filed Jun. 13, 2005, now U.S. Pat. No. 7,549,947 entitled MOBILE SYSTEMS AND METHODS FOR HEALTH, EXERCISE AND COMPETITION, which is incorporated herein by reference and which is a continuation application of U.S. patent application Ser. No. 10/045,619, filed Oct. 19, 2001, entitled METHOD AND APPARATUS FOR REMOTE INTERACTIVE EXERCISE AND HEALTH EQUIPMENT, now U.S. Pat. No. 6,921,351, which is incorporated herein by reference.

BACKGROUND

1. Technical Field

This invention relates generally to health and exercise equipment, and more particularly to computer networked systems including health or exercise equipment.

2. The Relevant Technology

Good health is a fundamental requirement for a happy and long life. A multi-billion dollar health and fitness industry has grown to help individuals meet this requirement. For example, there are a great many gymnasiums which provide facilities and equipment for aerobic and musculature development, and there are hundreds, if not thousands, of weight loss and diet centers and programs. The goals of these many programs typically include weight loss and/or maintenance, the improvement of aerobic fitness, improved circulation, increased strength, and body building or shaping.

There are several problems encountered with the use of gymnasiums, fitness centers, and diet centers. For one, they tend to be fairly expensive due to the need to maintain the facilities, pay rent and payroll, buy equipment, etc. In addition, these centers tend to be inconvenient in that they require a special trip to the center by individuals wishing to use their facilities. Both the price and the inconvenience tend to discourage use of these centers over time, allowing the individuals to lose incentive and drop out of their fitness or diet program.

A partial solution to this problem is home exercise and health equipment. Again, a large industry has arisen to provide exercise and health equipment for the home. This equipment tends to be more of the aerobic type, e.g. stationary bicycles, rowing machines, "step" machines, etc., although weight lifting apparatus, sometimes referred to as "resistance trainers," are also widely used in the home. These types of home exercise and health equipment increasingly use sophisticated electronics, such as microprocessors, to monitor the level of exercise and to provide exercise programs for the user.

Unfortunately, even well designed home exercise and health equipment often fall into disuse over time. This is because individuals, even in their own home, often lack the incentive to exercise when there are other, more enjoyable, activities available. Also, since there is typically not the camaraderie often found in a health club, diet center, etc., it is easier for users, as individuals, to discontinue their exercise or diet program.

Personal trainers have been used both at fitness clubs and in the home. Personal trainers are individuals who usually have a fitness training background and who typically provide personal training services to an individual customers. Personal trainers can be very effective in that they provide personal motivation and feedback to an individual in the exercise program, and thus often foster a more effective and longer-lasting exercise program. The downside of personal trainers is, particularly in the home setting, their relatively high cost. It is not unusual for a personal trainer to charge hundreds of dollars per month for their services. Therefore, while these personal trainers are very effective, they tend to be used by only a small percentage of the population.

It is also desirable to make exercise more of a group experience. It is well established that people are more likely to exercise in a group setting than they are on their own. With stationary exercise equipment this, in the past, could only be accomplished by physically locating the exercise apparatus near to each other, e.g. in a health club setting. With mobile exercise equipment, the exercisers would have to group together, such as assembling a group for bicycle ride. In either case, the ability to share a group exercise experience required users to physically get together. Also, such group exercise experiences were typically limited to same-type exercise equipment. That is, bicycle riders rode with bicycle riders, swimmers swam with swimmers, etc.

Even the individual and group experiences within a gymnasium or health club can be somewhat lacking. The exercise equipment are typically stand-alone, without allowing for the gathering of exercise session parameters, interactivity, remote communications, etc. It would be desirable to have such experiences expanded with enhanced capabilities as well.

BRIEF SUMMARY

The present invention provides an exercise and health system which is convenient, affordable, and effective. The system includes computerized exercise and/or health equipment (the "local system") that can provide feedback and encouragement to the user, i.e. can serve as a "virtual personal trainer." These local systems often include a local server to service multiple exercise devices. In addition, the system includes a remote system communicating over a bi-directional data channel (preferably the Internet) with the exercise and health equipment. This remote system can include remote servers communicating with the local system, and remote work stations used by trainers and users to interact with the remote servers and local systems.

Since the exercise and health equipment can communicate with the user, it is possible for the health equipment to provide incentive and motivation to the user much in the same fashion as a human personal trainer. In addition, the health and exercise equipment can store data and other parameters concerning the exercise or other activities which can be used to monitor the progress and to vary the exercise program or script. In this way, the local system can serve as a "virtual personal trainer." The data and other parameters can also be stored in the local server and uploaded to the remote server. From there, the data and parameters can be processed and/or accessed from the workstations and the local systems.

The remote server is preferably associated with a number of local systems. The remote server can be considered to be the communication tool of a human personal trainer via a workstation, as opposed to the "virtual personal trainer" emulated by software in the local system. Further, the remote server can provide for competitions and group exercising between virtually any number of users in any number of locations. Some of the users may be in fixed locations (such as on a rowing machine or a stationary bicycle), while other users may be in mobile locations, such as bicyclists and joggers. With appropriate handicapping, a person on a stationary bicycle can race with a person on a road bicycle (or even join the Tour de France), or with a person on a rowing machine. Further, "virtual" competitions can be held wherein an exercise device represents, for example, a spaceship, such that the more energy expended by the user results in faster spaceship movement. Such "virtual" competitions may use standard sensor of the exercise equipment to "steer" the spaceships. For example, a person on a fixed rowing machine could steer by pulling harder on one oar than another, or "fire" a missile by pushing forward on both oars. However, it is anticipated that various "out of band" signals may also be used to create a virtual competition.

In a preferred embodiment of the present invention, a distributed wide area network (WAN) such as the Internet is used to couple local servers, remote servers, and workstations together. Users at local systems can interact visually and even in a tactile manner with other users over the Internet. For example, a first user at a first local station can take a "virtual ride" with another user at a second local station through the Internet connection. Likewise, a remote "personal trainer" can interact with a user at a local station via the Internet communication linkage.

The systems, methods, and apparatus of the present invention therefore can provide an effective exercise, dietary, and health program for a great number of individuals. The computerized health equipment provides incentive and encouragement to stay in the program, due to the "virtual personal trainer" of the local system, the human personal trainer of the remote system, and by the various services provided by the enterprise as a whole as supported by the server systems, peer systems, etc. For example, a variety of services of products can be offered to the users of the system to further their health and fitness goals. In addition, the camaraderie of exercising with other users can be provided.

The described invention therefore creates a "virtual gymnasium" anywhere and everywhere it is desired. For example, exercise equipment within a traditional gymnasium or health club can interact with exercise equipment that is out of doors or in a home environment. Furthermore, multiple exercise equipment can communicate with a local server (in, for example, a home, gymnasium, or health club setting) for the gathering of exercise session parameters, providing user feedback, generating reports, etc.

It will be appreciated that implementations of the present invention are ubiquitous, appliance-like, and scaleable. In particular, by providing an inexpensive base controller for minimal "in-band" communications, the controller can be provided on virtually every exercise apparatus at minimal cost, leading to the ubiquitous nature of the invention. By providing "plug-and-play" functionality, the system becomes appliance-like. In the wireless embodiments of the local system, a compatible exercise device needs only be brought into proximity with a local server to become a part of the system. Further, the local server has an extremely simple base interface: a reset switch. Of course, additional interfaces such as a touch-screen video display can add further functionality. Finally, the system is scalable because the same base architecture can be used to couple from one piece of exercise equipment to many pieces of exercise equipment to the local and/or remote servers of the system.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

Figure 1:
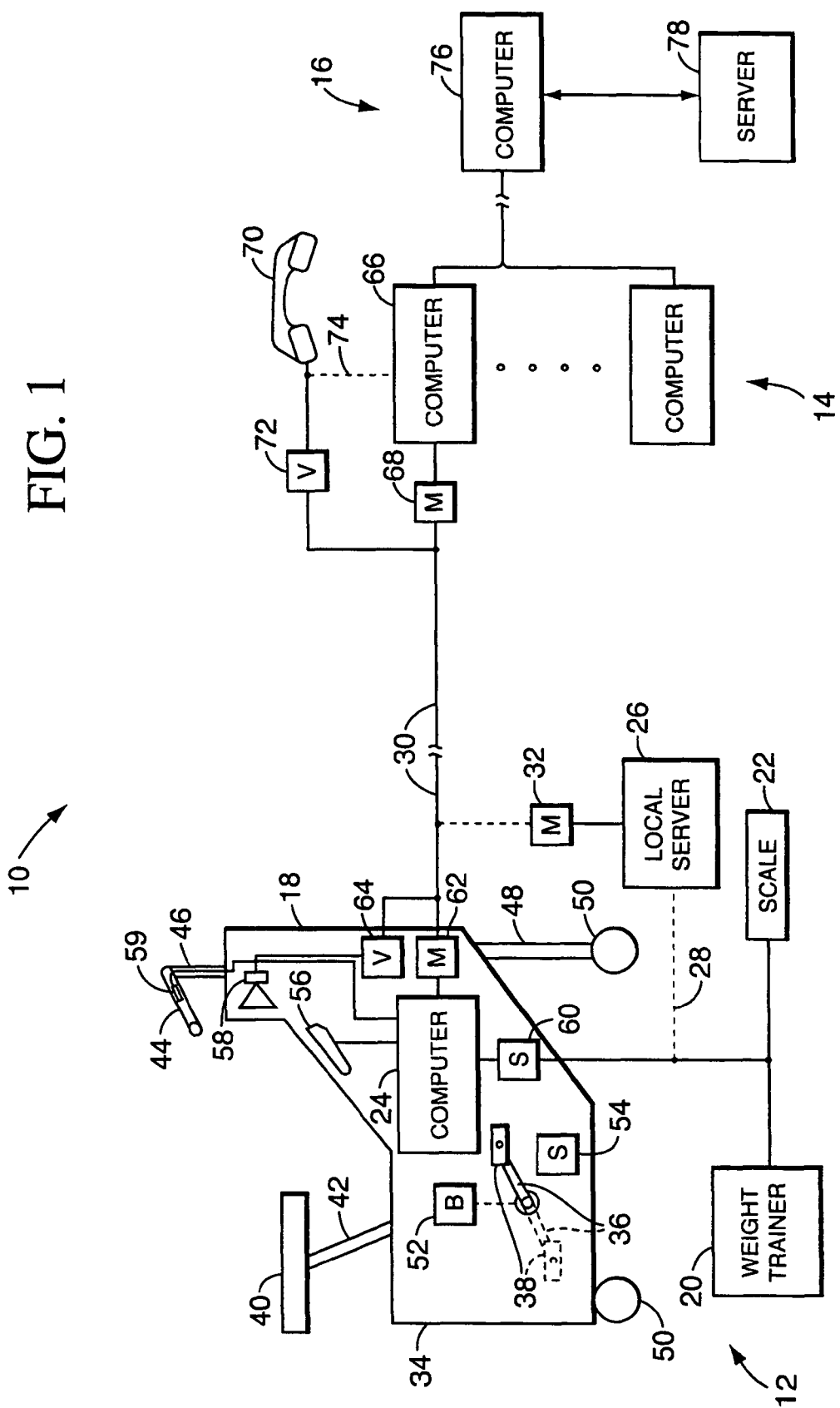
FIG. 1 is a block diagram of a health and fitness system in accordance with the present invention.

In FIG. 1, a health and fitness system 10 in accordance with the present invention includes one or more local systems 12, one or more remote systems 14, and one or more server systems 16. The local systems 12 are typically home-based systems designed for the promotion of the health and fitness of individual users within a family. The remote systems 14 may be home or business based, and are used as data gathering and storage stations, as well as communication stations, between a human personal trainer and users of local systems 12. As will be discussed in greater detail subsequently, the remote system 14 is associated with a relatively large number of local systems 12, e.g. a personal trainer with a remote system might be in communication with 100 or more individual users of local systems 12. This is made possible, in part, by providing a "virtual personal trainer" at each of the local stations 12 to partially or fully replace the need for a human personal trainer at the local station. The server systems 16 can communicate with the remote systems 14 to provide server and control functions across the entire enterprise, i.e. over the entire system 10. As also will be discussed in greater detail subsequently, the server system 16 is associated with a number of remote systems 14.

The local system 12 includes one or more health or fitness devices such as a stationary bicycle 18, a weight or "resistance trainer" 20, a scale 22, etc. Associated with a local system 12 is a computer 24 which, in this preferred embodiment, is integrated into the stationary bicycle 18. A stationary bicycle as a "base unit" is given merely by way of example, as any piece of equipment (a rowing machine, a step machine, etc.) could house the computer 24, or the computer 24 could be housed separately. The computer 24 can serve as a "local server" for other health and fitness devices at local system 12, such as the weight trainer 20 and the scale 22. Alternatively, a separate local server 26 can be used to control and/or support various devices in local system 12 via data and control lines 28, and communicate with the remote system 14 via a telephone line 30 and a modem 32. However, in the present preferred embodiment, the assumption is that the local server 26 and modem 32 are not required and that the computer 24 will serve not only to control the operation and data gathering function of the stationary bicycle 18, but will also provide these functions for the weight trainer 20 and the scale 22. Of course, the weight trainer 20 and the scale 22 may include their own computer systems for local control purposes.

The stationary bicycle 18 includes a housing 34 which, as stated previously, preferably houses the computer 24, a crank 36 provided with a pair of pedals 38, a seat 40 supported by a seat stem 42, handle bar 44 supported by handle bar stem 46, legs 48, and feet 50. The various components of the stationary bicycle 18 are typically attached to a rigid frame that is internally connected to the housing 34.

The weight trainer 20 is preferably a resistance-type weight trainer, such as a bench press machine, a biceps curl machine, a squat machine, etc. Typically the use grasps a bar connected to a cable that is attached to a resistance device. This resistance device can be weights, or can be an active resistance device such as a motor, or a passive resistance device such as an electrically actuated brake. Active resistance devices are advantageous in that they can provide a force-feedback that can closely mimic real-world conditions, i.e. the actual forces that might be felt by a user when lifting real weights with a human "spotter" or trainer. In any event, the amount of resistance to movement of the bar (or other portions of a piece of exercise equipment) is preferably under the control of the computer 24 and the script that it is running. Particularly with active resistance devices, the control by the local computer is important. This is because a tight feed-back loop between sensors and actuators (such as motors, solenoids, etc.) is desirable to create realistic force feed-back. This would be difficult to accomplish in a realistic manner over a communication linkage, unless such a linkage were extremely fast. However, even in the case of an extremely fast communication linkage, the performance of a remote computer would likely diminish as it was attempting to control even one local system, let alone many local systems. The scale 22 preferably provides an electrical connection to the computer 24 through an I/O port to allow the computer 24 to monitor the weight of the person standing on the scale.

The computer 24 is coupled to a variety of input/output (I/O) devices including a brake 52, a sensor 54, a display 56, a heart rate monitor (HRM) 59, a loudspeaker 58, an interface 60, a modem 62, and a voice board 64. In this fashion, the computer 24 can control and monitor the various functions of the stationary bicycle 18.

More particularly, computer 24 can, under software and hardware control, control the electrically actuated brake 52 which is coupled to the crank 36 of the stationary bicycle. In this fashion, the pedaling force that must be exerted on pedals 38 to cause the crank 36 to rotate at a given speed can be varied under computer control. This electrically actuated brake can be electric/mechanical brake, electric/magnetic brake, etc. as it is well known to those skilled in the art. The brake 52 can be passive (i.e. one that creates a frictional, magnetic or other drag) or active (e.g. a motor/generator that resists the movement of the crank 36). The sensor 54 is typically used to determine the rotations-per-minute (RPM) of the crank 36. In this way, the computer 24 can receive information concerning the level of effort being exerted by a user of the stationary bicycle 18. Rotation sensors are well known those skilled in the art. The sensor 54 can also measure other parameters such as the force (torque) being applied to pedal 38, again to provide information to the computer as to the level of effort being exerted by the user of the bicycle.

The computer can provide an output on a display 56 that can be viewed by an individual user sitting on seat 40. This display can be a simple light display, e.g. a series of light emitting diodes (LEDs) or it can be a full video display. A preferred embodiment of the present invention provides a full video display to provide instructions and encouragement to a user of the stationary bicycle. For example, an image of a "virtual personal trainer" can be provided on the video display 56. This image is preferably the image of the human personal trainer who is in charge of the remote system 14.

The loudspeaker 58 provides another important communication medium to the user of the stationary bicycle 18. For example, under computer 24 control, the user can be told with either a digitally synthesized or digitally recorded voice to pedal faster, pedal slower, that they are doing a good job, etc. Of course, analog recording techniques can be used as well, but are considered to be less flexible and desirable. Preferably, the voice being used is that of the personal trainer associated with the remote system 14 that oversees that local system 12. Both voice synthesis and digital voice recording on computer systems 24 are well known to those skilled in the art.

A local interface 60 can be used to couple the computer 24 to additional health and fitness devices. In this instance, the local interface 60 is coupled to the weight trainer 20 and to the scale 22. This additional health and fitness systems can either "dumb" systems with limited digital computation and storage capabilities, or they can include full fledged computer system such as the computer system 24. In the present embodiment, the weight trainer 20 and scale 22 include digital control circuitry (e.g. a microcontroller) which can communicate with the more powerful computer 24 of the stationary bicycle 18. The various I/O devices, such as the loudspeaker 58 can be used in conjunction with these other devices 20 and 22, e.g. the weight detected by the scale 22 can be announced on the loudspeaker 58 along with an indication that this is an increase or decrease in weight from the last session. Also, as mentioned previously, the weight trainer 20 can include the equivalent of the electrically controlled brake 52 which allows the resistance of the weight bar or handle to be varied to provide resistance ("weight") training. This control of the brake within the weight trainer 20 can be controlled by a "script" of the computer 24.

The computer 24 is also coupled to a modem 62 for communication over a telephone line 30. Alternatively, the computer 24 can be coupled to the remote computer 14 by other communication linkages, such as ISDN digital transmission line, via a local area network, or via a wide area network (WAN) such as the Internet. In other words, the telephone line 30 represents only one type of data communication channel between the local systems 12 and the remote system 14. The Internet, which has been growing rapidly in popularity, is a particularly good communication linkage due to its ubiquitousness, power, and flexibility. As will be appreciated by those skilled in the art, the Internet is one form of distributed packet network where data is broken into packets which can travel along a multitude of paths between source and destination. The Internet (and private networks known as Intranets) are packet networks operating on the well-known TCP/IP protocols.

The present embodiment also includes a voice board 64 which can bypass the modem such that the loudspeaker 58 can be driven directly to the telephone line 30 in an analog fashion. Combination modem/voice boards are commercially available for personal computer systems, and are well known to those skilled in the art.

The remote system 14 includes, for example, a remote system computer 66 which is coupled to the telephone line 30 by a modem 68. In addition, a telephone 70 can be coupled to the line 30 by a voice board 72. Alternatively, the telephone 70 can be coupled to a separate telephone line so that simultaneous telephone and data links can be made. Still further alternatively, it is known to those skilled in the art that a single telephone line can be made to support both voice and data transmission. In any event, the telephone 70 can communicate directly with the loudspeaker 58 of the stationary bicycle 18 over the standard analog telephone line 30. Alternatively, the telephone 70 can communicate with the computer 66 as indicated by the broken line 74 and the computer 66 can communicate digital voice data via modem 68, telephone line 30 and modem 62, to the computer 24. The computer 24 can then store or pass through the digital voice data and play the voice input to the user of local station 12 via speaker 58.

As noted above, the computer 66 is used to communicate with the local system 12 via computer communication link or "transmission medium" such as the telephone line 30 or an equivalent. This communication can include the downloading of data and instructions to the computer 24, and can include the uploading of information from the computer 24 to the computer 66. This allows for interactive communication between the remote system 14 and the local systems 12.

The server stations 16 are used to further consolidate information from multiple remote system 14 and to provide a variety of services to the remote systems 14. While the remote system 14 may be housed in human personal trainer homes or work sites, the server system(s) 16 are preferably more regional or national in origin. In this way, the main office of the enterprise can access each of the server systems 16 to provide upgrades for software, exercise programs, exercise equipment scripts, etc., as well as receiving information from the remote computers 66 that can be used for further analysis and for providing further services. Part of this analysis can be on the general and specific level of fitness of various individual users of the local system 12, as well as marketing information that can be used to offer product and services particularly tailored for the various users of the local system 12. The performance of the human personal trainers at remote stations 14 can also be monitored. It should be noted that the server 16 can include direct connect server 76 and peer server 78 that can either be direct server itself (like server 76) to a number of remote stations 14, or which can be a specialized server (such as a dietary analysis server) coupled to one or more direct connect servers 76. In addition, higher-level servers can be used to further consolidate data from the direct connect servers 76 and/or the peer servers 78. For example, the direct connect servers 76 can be regional in scope, while higher level servers can be national or international in scope.

Figure 2:
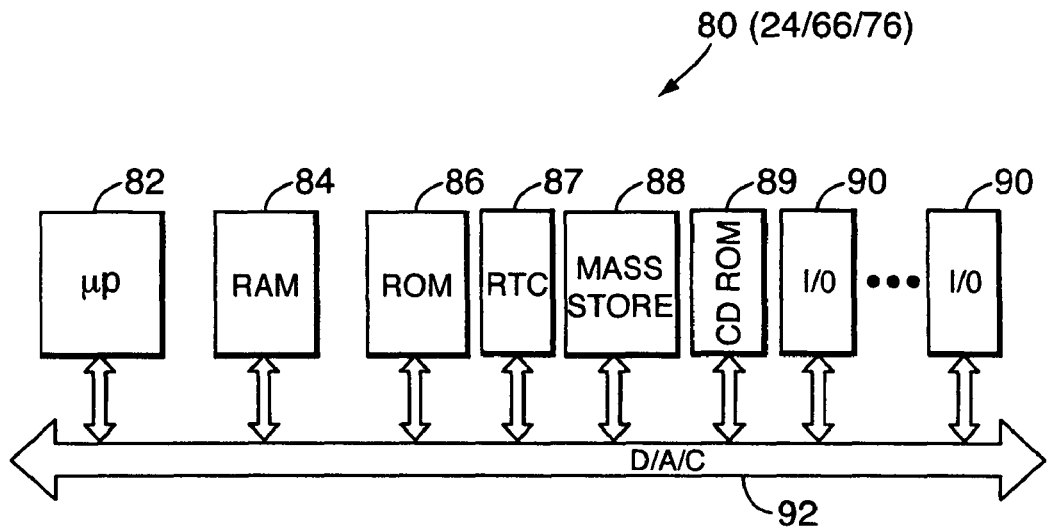
FIG. 2 is a block diagram of the local, remote, and server system computers of the present invention.

In FIG. 2, a computer 80 is shown in a block diagram form. This basic computer architecture can be used for the local system computer 24, the remote system computer 66, and the server system computer 76. Of course other and equivalent architectures (in the computational sense), such as parallel processing computers can be used in the present invention as well. In the disclosed embodiment, the computer 80 includes a microprocessor 82, random access memory (RAM) 84, read only memory (ROM) 86, real time clock (RTC) 87, digital mass storage 88, CD-ROM drive 89, and a number of input/output (I/O) ports 90. Preferably, the digital mass storage 88 is read/write memory such as a hard disk with adequate storage capacity (e.g. 40 megabytes to 2 gigabytes or more). In addition, CD-ROM drive 89 can be coupled to the bus to provide, in particular, images to be displayed on a display 56 of the local system 12. The various components 82-90 address, pass data, and pass control signals through a bus 92 which typically includes data (D), address (A), and control (C) lines, as it is well known to those skilled in the art. In addition, there are control and "glue" chips typically provided in the form of a "chipset" which are used to couple the various components of the system together. The design and manufacture of computer systems such as computer system 80 is well known to those skilled in the art, and such computer systems are commercially available, both as complete systems and as subsystems (e.g. motherboards) from a variety of commercial sources.

Figure 3:
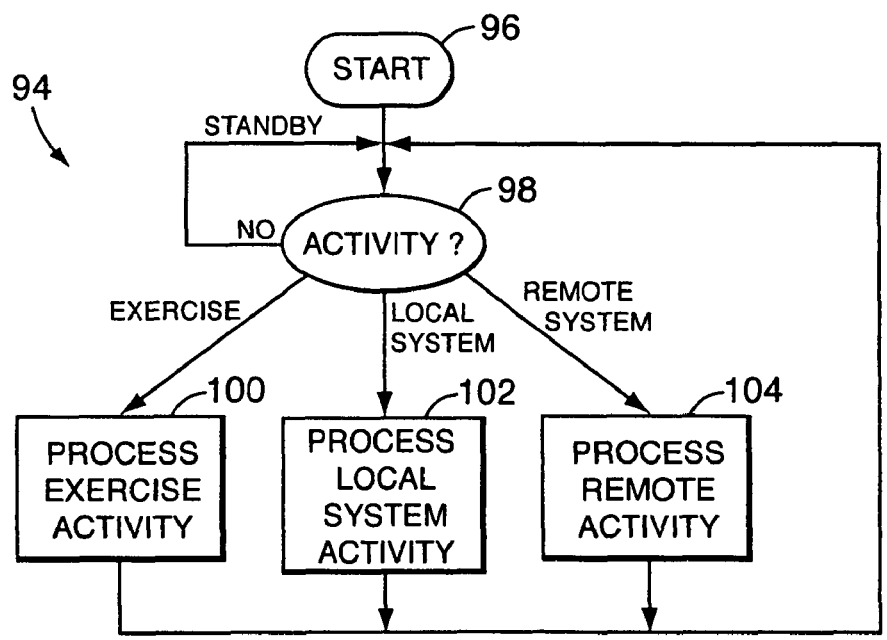
FIG. 3 is a flow diagram of a process running on a local system computer of the present invention.

In FIG. 3, a process 94 implemented on a local system computer 24 is illustrated in a flow diagram. The process begins at 96 and, in a decision operation 98, it is determined whether there is any activity which requires the attention local system computer. If not, the computer system 24 is in a "standby" mode and process control is returned to operation 98 in a recurring manner. If operation 98 does determine that there is some activity, one or more of multiple branches are made to process the activity. If the activity is "Exercise", e.g. the stationary bicycle 18, the weight trainer 20, or the scale 22 is to be used, an operation 100 processes the exercise activity. If it is a "Local System" activity such as routine housekeeping, the local system activity is processed in an operation 102. If it is a "Remote System" activity, the remote system activity is processed in an operation 104. After the completion of any one of steps 100, 102, and 104, process control is returned to operation 98. Of course, other types of activities can be initiated by operation 98 such as, for example, a shut down activity which would cause a power-down of system, as will be appreciated by those skilled in the art.

Figure 4:
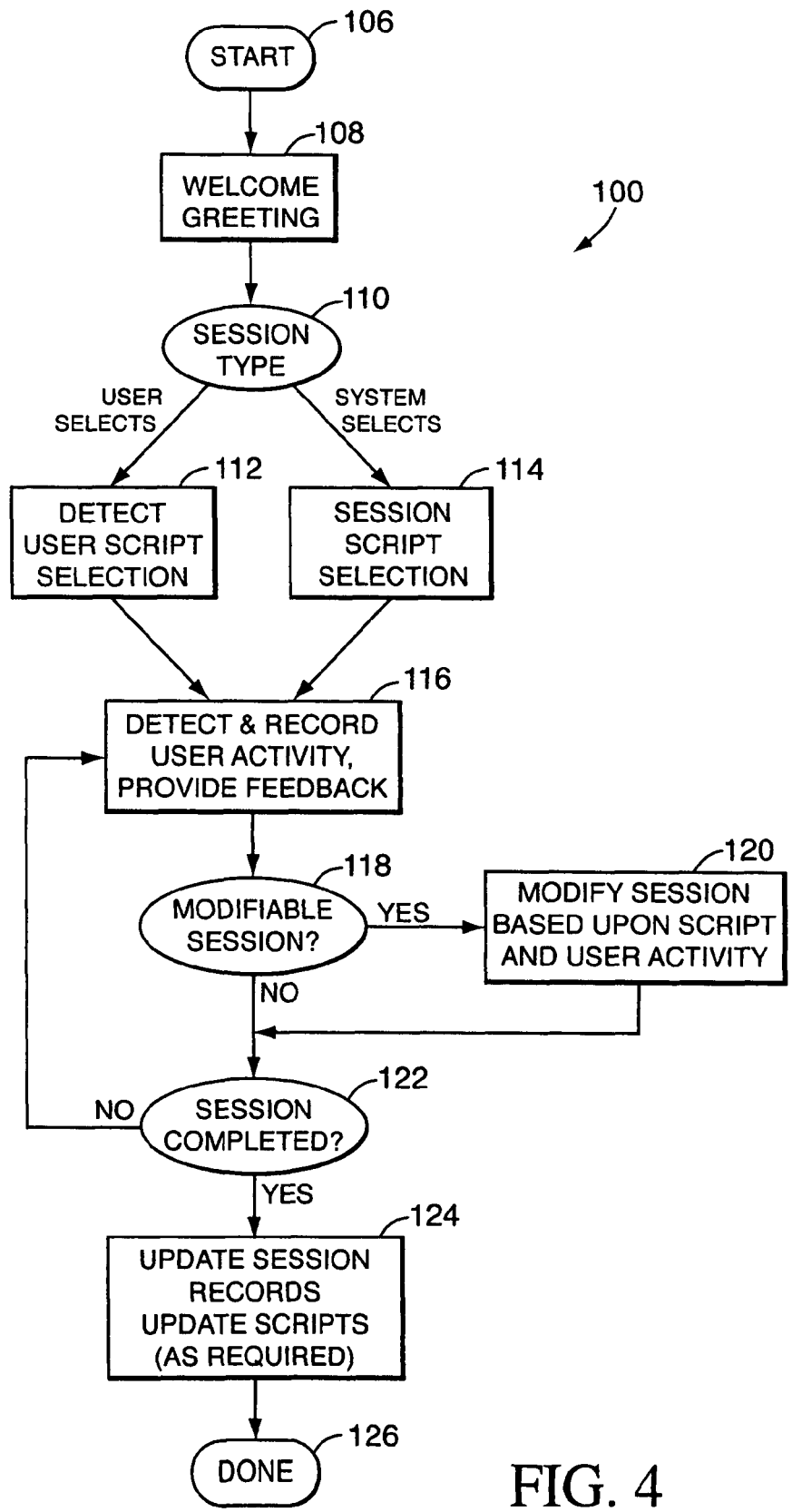
FIG. 4 is a flow diagram of the "Process Exercise Activity" operation of FIG. 3.

In FIG. 4, operation 100 of FIG. 3 is illustrated in greater detail. The process 100 begins at operation 106 and, in an operation 108, a "welcome greeting" is created. This welcome greeting can be displayed on the screen 56 and/or can be heard from the speaker 58, and can be personalized to both the individual user of the local system 12 and the human personal trainer of remote station 14. For example, the image of the personal trainer can show up on the screen 56 with his voice saying "Good morning, Fred! I haven't seen you since last Wednesday. Let's try to get in a good work-out today!" This greeting forms a part of a "virtual personal trainer" at local system 12 which replaces some or all of the need for a human personal trainer to be present at the exercise session at the local system 12. The "virtual personal trainer" is, therefore, a computerized process which emulates part or all of the functions traditionally performed by a human personal trainer.

Next, in a selection operation 110, the user decides whether he wants to select his own training program for that session or if he would like the system 12 to select the program. If the user selects the program, he creates a user "script" of what kind of exercise program he would like to perform that day. For example, if the user wishes to simply bicycle at a fixed resistance for thirty minutes, that can be entered in operation 112. Alternatively, more complex "scripts" can indicate that he would like to bicycle with interval training for thirty minutes, and then do five repetitions on the weight trainer 20.

If, however, the user allows the system 12 to select the section type, operation 114 controls the script selection. This is the preferred mode for using the local station 12 in that the script can be influenced not only by the local station 12, but also by the human personal trainer at the remote system computer 66. For example, data concerning the user's previous performances and the personal trainer's guidance can be stored in mass storage 88 (e.g. on a hard disk) so that a custom-tailored, interactive exercise program can be provided.

As noted above, the exercise program preferably proceeds according to "scripts." A script is simply a sequence of exercise or other health-related events that are performed in fixed or variable sequences. The order and structuring of the script can be modified based upon monitoring the user's performance or by other user feedback. For example, if it is detected that the user is getting tired due to a slowing of the exercise repetition rate, the operations or parameters of the exercise script can be modified accordingly. In other words, certain script steps can be skipped or the parameters concerning the steps can be modified. For example, if a user is determined to be tiring by the local system 12, and if the script says the next exercise event is to be ten repetitions on the weight trainer 20, that operation could be skipped. Alternatively, the weight training operation could still be done, but the resistance parameters could be modified. For example, instead of doing ten repetitions at a hundred pounds resistance on the weight trainer 20, eight repetitions at eighty pounds of resistance might be called for. The script therefore provides a general framework of a desired exercise session which can be varied based upon human personal trainer input from remote system 14, user input at local station 12, and detected user performance at local station 12.

Once the script has been initiated in either operations 112 or 114, an operation 116 detects and records user activity and provides feedback to the user. This operation will be discussed in greater detail subsequently. Such parameters as the rotations per minute (RPM) of the crank 36, the timing and speed of the resistance weight repetitions of weight trainer 20, the detected weight on the scale 22, etc. can all be recorded in the mass storage 88 of the local system computer 24. In addition, user feedback is provided. For example, if the person is cycling too slow on the stationary bicycle 18, the computer 24 can generate a encouragement on speaker 58 that the person should pedal faster. Alternatively, if it is determined that the user is over-exerting, such as pedaling too fast, a cautionary warning can be issued on speaker 58 to slow down. Another important input is the heart rate monitor (HRM) 59 which detects if the heart (pulse) rate is rising too high.

Next, in an operation 118, it is determined whether the session is a modifiable session. Most sessions are preferably be modifiable, unless the user selects, in an operation 112, a non-modifiable session. If the session is modifiable, the session is modified in an operation 120 based upon the selected script and upon user activity or other input. For example, if the heart rate monitor 59 detects that the pulse rate is too high, the resistance on the crank 36 can be reduced via a signal to the brake 52. Next, in an operation 122, it is determined whether the session is completed. This is usually based on the script, although the user can always terminate a session. If the session is not completed, process control is returned to operation 116 to repeat the loop. If the session is completed, the session records are updated in the mass storage 88, as are the scripts, as indicated in operation 124. The process 100 is then completed at operation 126.

Figure 5:
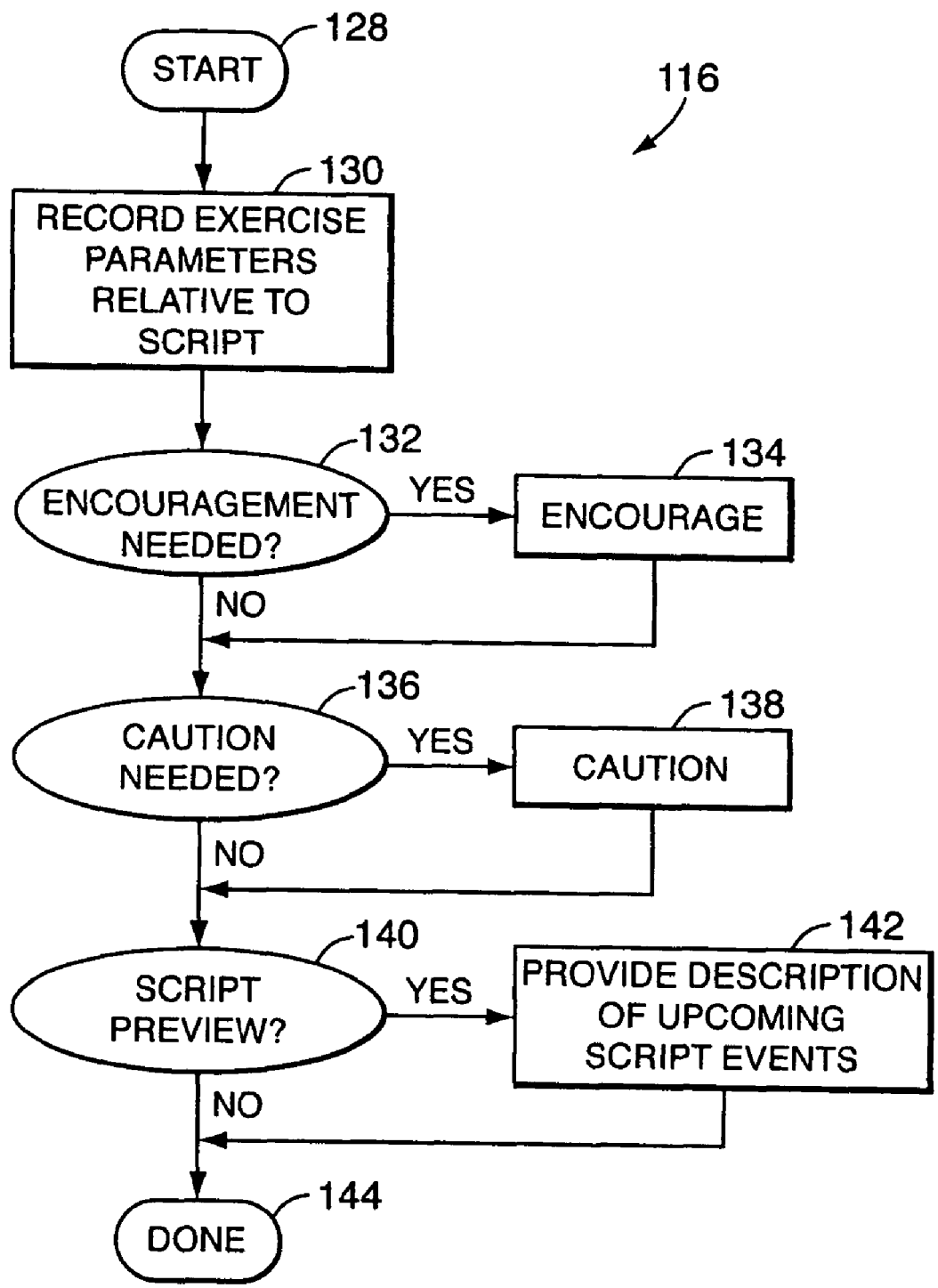
FIG. 5 is a flow diagram of the "Detect And Record User Activity, Provide Feedback" operation of FIG. 4.

In FIG. 5, the operation 116 of FIG. 4 is explained in greater detail. Process 116 begins at 128 and, in an operation 130, exercise parameters relative to the script are stored, preferably in mass storage 88. These parameters depend on the type of exercise being done, and the type of sensory input available to the system 12, but typically includes such things as time, RPM, resistance, machine state, etc. These exercise parameters are used to control the implementation of the exercise script, and are stored for later analysis.

Figure 6:
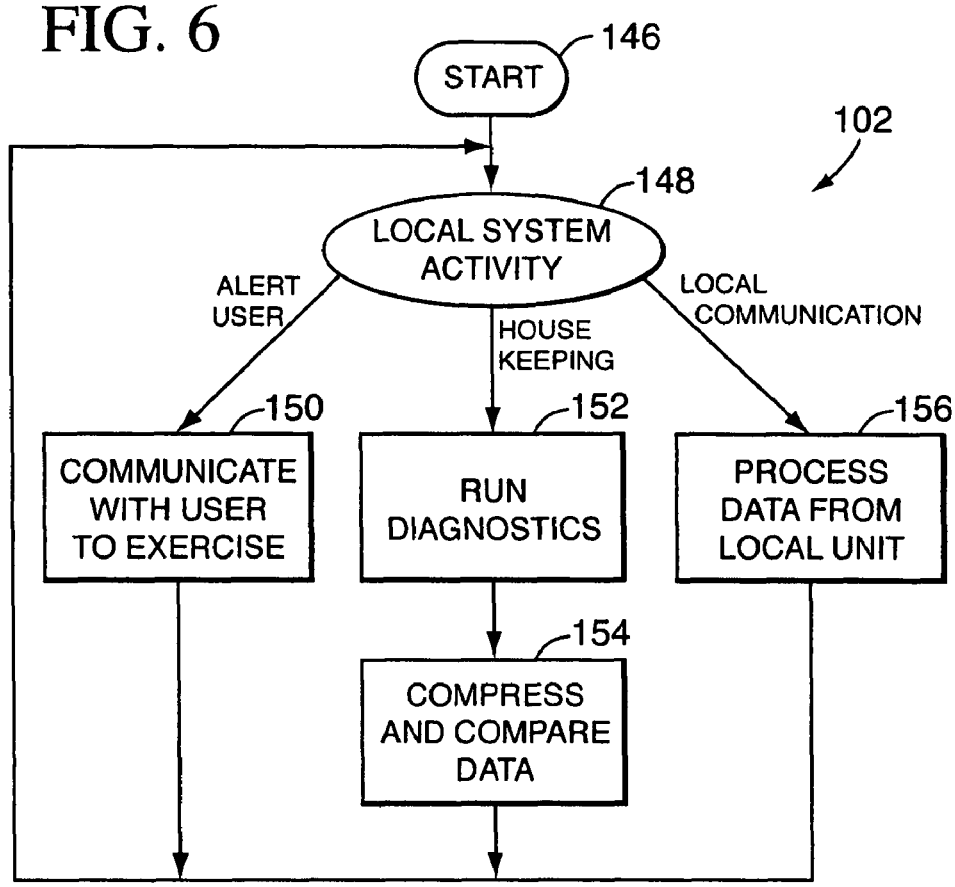
FIG. 6 is a flow diagram of a "Process Local System Activity" operation of FIG. 3.

Next, in an operation 132, it is determined whether encouragement is needed. An example of encouragement being needed is when the person is slowing down below the suggested repetition rate or speed in the script or, for example, has stopped exercising entirely. In such circumstances, encouragement is given in an operation 134. Again, this encouragement can be auditory via speaker 58, or visual via display 56, a combination of the two, or in any other suitable fashion. Next, in an operation 136, it is determined whether a caution is needed. If so, the caution is given in an operation 138 either through auditory, visual, or other ways. Caution might be needed if the user is exercising faster than that suggested by the script or if a dangerous physical condition is detected, such as by the HRM 59. Next, in an operation 140, it is determined if a script preview should be provided. If yes, an operation 142 provides an auditory, visual or other type of preview of upcoming script events. For example, the system 12 could be taking a user on a imaginary bicycle ride through the country. The script preview would then, in an operation 142, indicate something like "We are now approaching a hill. You will note an increased resistance to pedaling in a few seconds which will steadily increase until we reach the crest of the hill in about one and a half minutes." These operations 134, 138, and 142 are further examples of the local system 12 serving as a "virtual personal trainer." The process 116 is completed at operation In FIG. 6, operation 102 of FIG. 3 is illustrated in greater detail. Process 102 begins at operation 146 and, in an operation 148, it is determined what type of local system activity is to be performed. Three different local system activities will be discussed herein by way of example. As a first example, the local system activity can be to alert the user as indicated in an operation 150. For example, the local computer 24 can detect that it is time for a scheduled exercise session. The computer 24 can then communicate with the user via speaker 58 that it is time for a scheduled exercise. In this instance, the computer 24 would use a real time clock (RTC) 87 to know that it was time to initiate the exercise session. After completion of operation 150, process control is returned to operation 148.

A second type of local system activity would be housekeeping. For example, in an operation 152, diagnostics can be run to check the operability and calibration of the various components of local system 12. Also, in an operation 154, data compression, hard disk compaction, and data preparation can be accomplished.

A third example of local system activity detected by operation 148 is a local communication within the local system 12. For example, the weight trainer 20 or the scale unit 22 might be communicating to the computer 24 via the interface 60 or vice-versa. An operation 146 processes the data from the local unit accordingly and can provide commands to the local unit for the exercise or health session. Process control is then returned to operation 148 after the completion of operations 150, 154, and 156.

Figure 7:
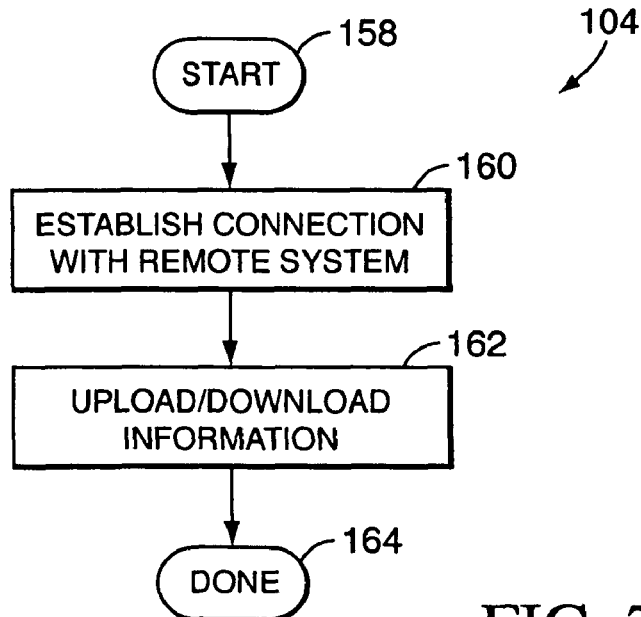
FIG. 7 is a flow diagram of the "Process Remote Activity" operation of FIG. 3.

In FIG. 7, operation 104 of FIG. 3 is illustrated in greater detail. The process 104 begins at 158 and, in an operation 160, the connection is established with the remote system. Next, in an operation 162, information is uploaded or downloaded, the process is completed at 164. It should be noted that the connection of operation 160 can be either an incoming connection or an outgoing connection. If there is an outgoing connection to a remote system computer 66 the modem 62 makes connection with the telephone line 30 and dials the telephone number of the remote system computer 66. For an incoming connection, the modem 62 detects an incoming call on telephone line 30, picks up the line, and connects to the local system computer 24.

Since the systems 12 are typically home based, the user may wish to use a single telephone line for both normal telephone needs and for use by the system 12 for operation 160. It would, of course, be simpler to have an additional telephone line installed simply for the system 12, but this may be impractical from a cost point of view. If the system 12 is sharing the telephone line with the other telephones and devices in the household, mechanisms and/or processes are preferably provided to prevent interference with normal telephone usage. If the local system 12 initiates the call to the server 66, it would simply need to detect whether the telephone line was available so as not to interfere with other use of the telephone line. It can help ensure this availability by calling at unusual times, such as the middle of the night or when it is known that the user is away from the home, e.g. at work.

However, with incoming calls from a computer 66 to the computer 24 on a single home line, some way of distinguishing between calls for the local system 12 and other kinds of telephone calls should be preferably provided. Again, this could be time-based such that it is implied that a telephone call in the middle of the night is for the local system 12. The RTC 87 could be used for timing purposes in this situation, or the computer could simple start a counter. In this instance, the modem 62 would pick up the telephone quickly before other devices, such an answering machine for a facsimile machine, would have a chance to pick it up. Alternatively, the local system 12 could allow a number of "rings" before picking up the line. For example, the local system 12 could allow the telephone line 30 to ring six times before modem 62 picks up the line. In a still further instance, the computer 66 might be calling a local computer 24 and have the phone line picked up by the user or by another device (like a telephone answering machine) coupled to the telephone line 30. In this instance, the computer 66 could hang up the line and call back a second time. Since the computer 24 can monitor the line via modem 62, it could know that a call back within, for example, thirty seconds of a hang up is for the computer 24. Alternatively, it could listen to the line on the first call to determine if it was computer 66 calling, and then pick it up the line 62 immediately on any call back, or call back the remote system computer 66 itself when the telephone line was free. Again, RTC 87 can be used for timing purposes, or counters can be used, as is well known to those skilled in the art.

Information being uploaded can include parameters and data stored in the mass storage 88 concerning the exercise sessions by the user(s) of the local system 12. It can also include other system information used for diagnosing or improving the operation of the local system 12. In addition, information can be downloaded to the local system 12 from the remote system computer 66 to, for example, change exercise scripts for a user, provide upgrades for the software running on the local system computer 24, etc.

Figure 8:
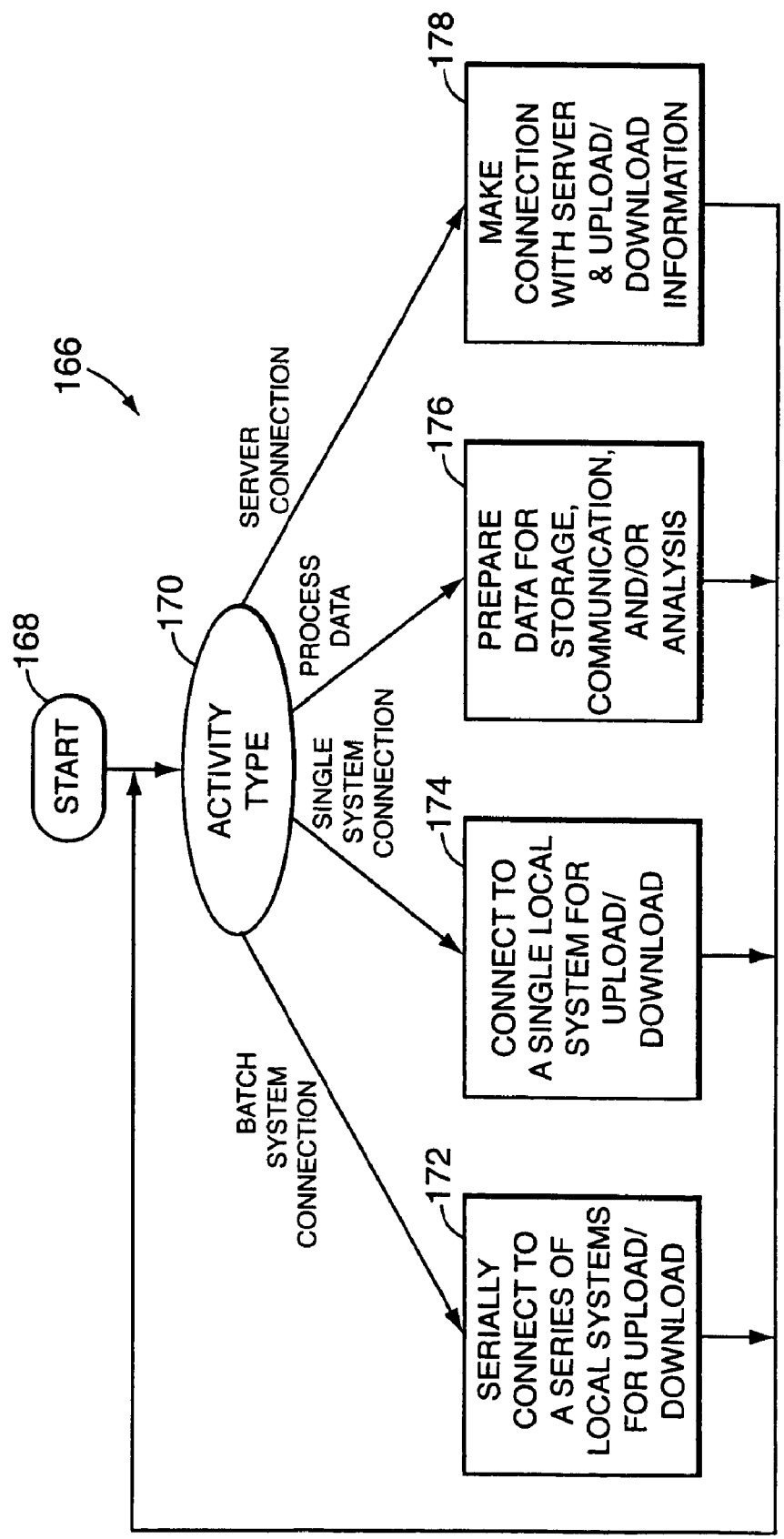
FIG. 8 is a flow diagram of a process running on a remote system computer of the present invention.

In FIG. 8, a process 166 running on a remote system computer 66 is illustrated. The process 166 begins at 168 and, in an operation 170, an activity type is determined. A first type of activity is a batch system connection whereby the remote system computer 66 sequentially connects with a series of local systems for the uploading or downloading of information. This process is accomplished in operation 172. A batch system connection can be used to update the software on a number of computers 24 of local system 12, or to upload exercise session data from a number of local systems 12 on a regular basis, e.g. daily, weekly, monthly, etc.

If operation 170 detects a single system activity type, an operation 174 connects the remote system computer 66 to a single local system 12 for uploading and/or downloading as described previously. If an activity type "Process Data" is detected by operation 170, an operation 176 prepares data on the computer 66 for storage, processing, communication, and/or analysis. Examples of some types of analysis of the data will be discussed subsequently with referenced to FIGS. 8a-8c. Finally, if an activity type "Server Connection" is detected, a connection is made with the server 76 to upload or download information. The server connection can be initiated by the computer 66, or it can be initiated by the server system computer 76 depending on the circumstances. Upon the completion of any of the operations 172, 174, 176, and 178, process control is returned to operation 170.

Figures 8A, 8B:
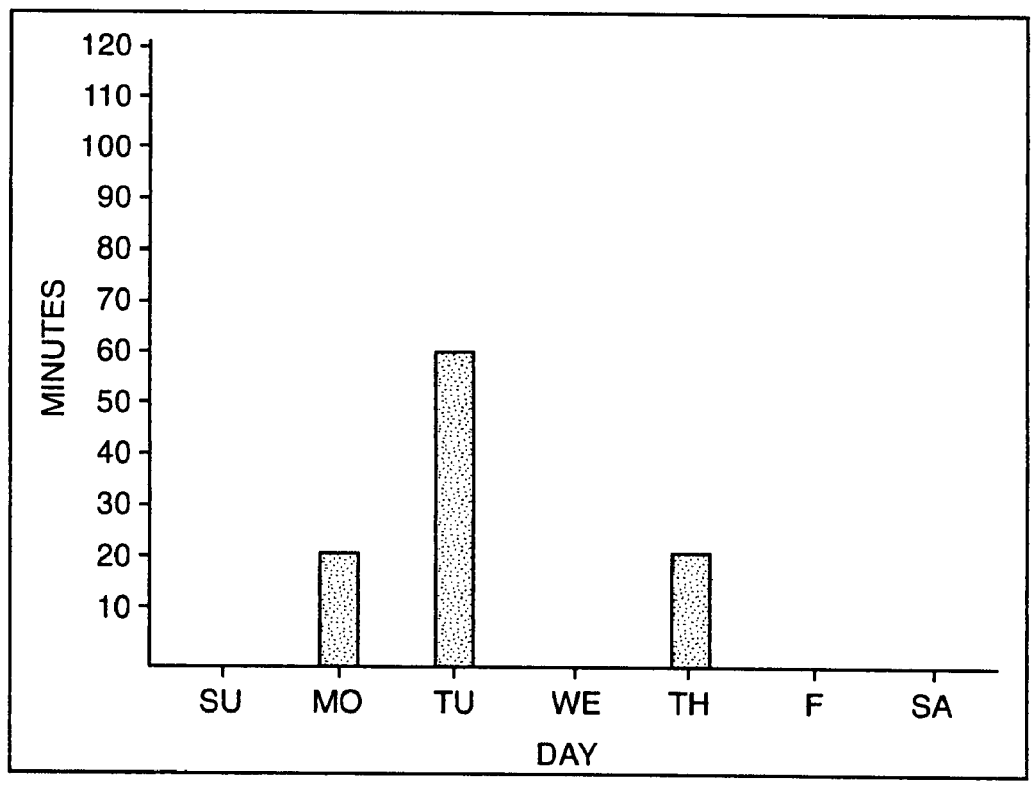
FIGS. 8a, 8b, and 8c are three examples of data analysis performed in the "Process Data" operation 176 of FIG. 8.
Figure 8C:
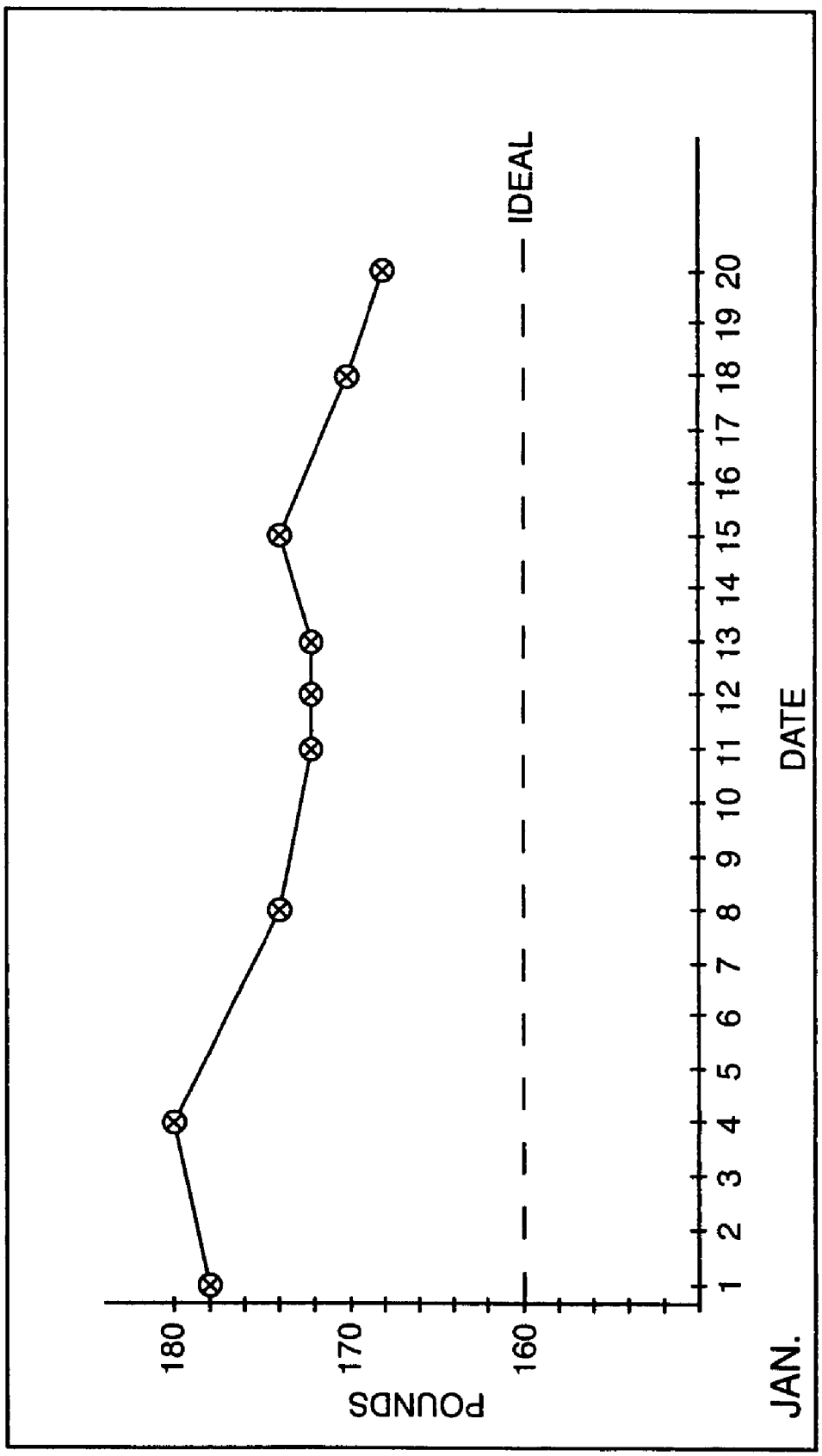

In FIGS. 8a-8c, several examples of types of data analysis that can be performed on the remote system computer 66 in operation 176 of process 166 are illustrated. Of course, this analysis can be accomplished at any of the computers on the system 10 including the remote system computer 66, server system computer 76, peer system computer 78, or even on the local system computer 24. In FIG. 8a, a display of exercise activity is shown. This display can be on the display on a video display, such as a display 56, or it can be printed to make a permanent record. Along the y axis are the number of minutes of exercise, and along the x axis are the days of the week. As seen in the illustration of FIG. 8a, on Monday the user had twenty minutes of exercise, on Tuesday the user had sixty minutes of exercise, and on Thursday the user again had twenty minutes of exercise.

In FIG. 8b, another display or print out of, preferably, the remote system computer 66 is a summary of daily exercise activity. As noted, the Monday twenty minute exercise session actually consisted of a ten minute cycling session and a ten minute weight session. Also includes is a summary of the number of calories burned and other parameters associated with those activities.

In FIG. 8c, a plot of the user's weight as taken from scale 22 is shown illustrating the day-by-day weights of the user during part of the month of January. In this way, users are provided with good feed-back concerning the progress he/she is making in reaching their ideal weight. This information can be used by the remote or server systems to modify the exercise scripts and/or provide dietary counseling or products to the individual users of local stations 12.

As noted, the analysis of the data is preferably accomplished at the site of the human personal trainer, i.e. the site of the remote system computer 66. However, this analysis can also be accomplished at upstream or downstream computers. As mentioned previously, the computer 24 of the local system 12 is perfectly capable of making these types of analysis and displaying the on the display 66. Also, a simple printer I/O port can be provided in the stationary bicycle 18 to allow a printout of the graphs and charts that were shown by way of example in FIGS. 8a, 8b, and 8c.

Figure 9:
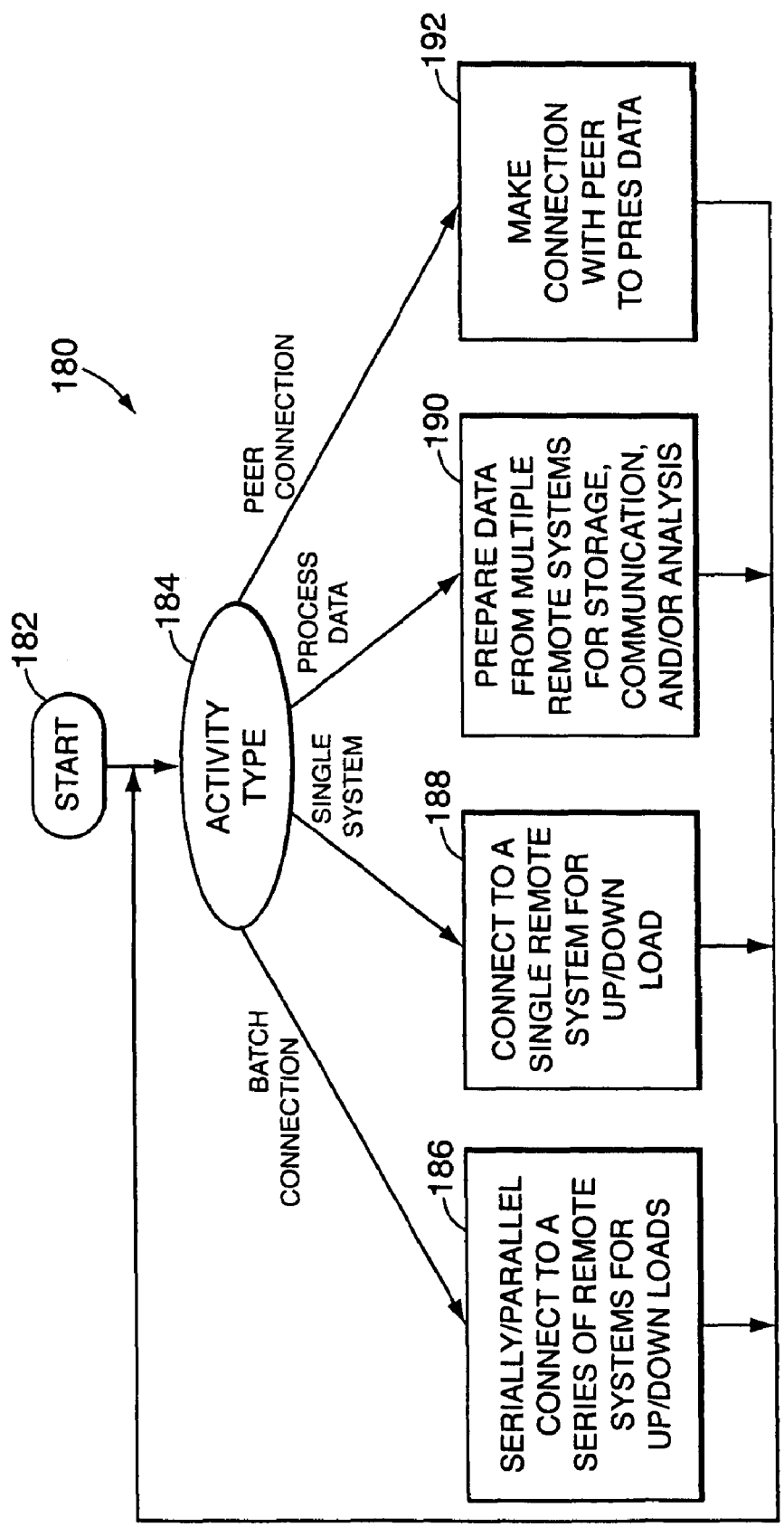
FIG. 9 is a flow diagram of a process running on a server system computer of the present invention.

In FIG. 9, a process 180 running on server system computer 76 is illustrated. In many ways, the process 180 running on the server system computer 76 is very similar to the process 166 running on the remote system computer 66. The process 180 begins at 182 and, in an operation 184, an activity type is detected. One type of activity type is the batch connection where the server sequentially (e.g. serially and/or in parallel) connects to a series of remote system computers 66 for uploading and downloading information. This process is accomplished at operation 186. Another activity type detected by operation 184 is the single system connection accomplished in operation 188. In operation 188, the server connects to a single remote system for uploading or downloading. In the case of operation 186 where there is a batch connection, the server system computer 76 will almost always be the initiating computer for the connection. With the single system connection however, the initiation of the connection can come either from the server 76 or from the remote system computer 66.

If operation 184 detects a "Process Data" activity type, the data for multiple remote system computers 66 (which includes data from multiple local system 12) is prepared for storage, processing, communication, and/or analysis in an operation 190. If an operation 184 determines that there is to be a peer-to-peer connection with a peer server 188, an operation 192 makes the connection with the peer server to pass data back and forth. Of course, there are other activity types that can be performed by the process on server system computer 76, these four being by way of example. After the completion of operations 186, 188, 190, or 192, process control is returned to operation 184 to detect another activity type.

Figure 10:
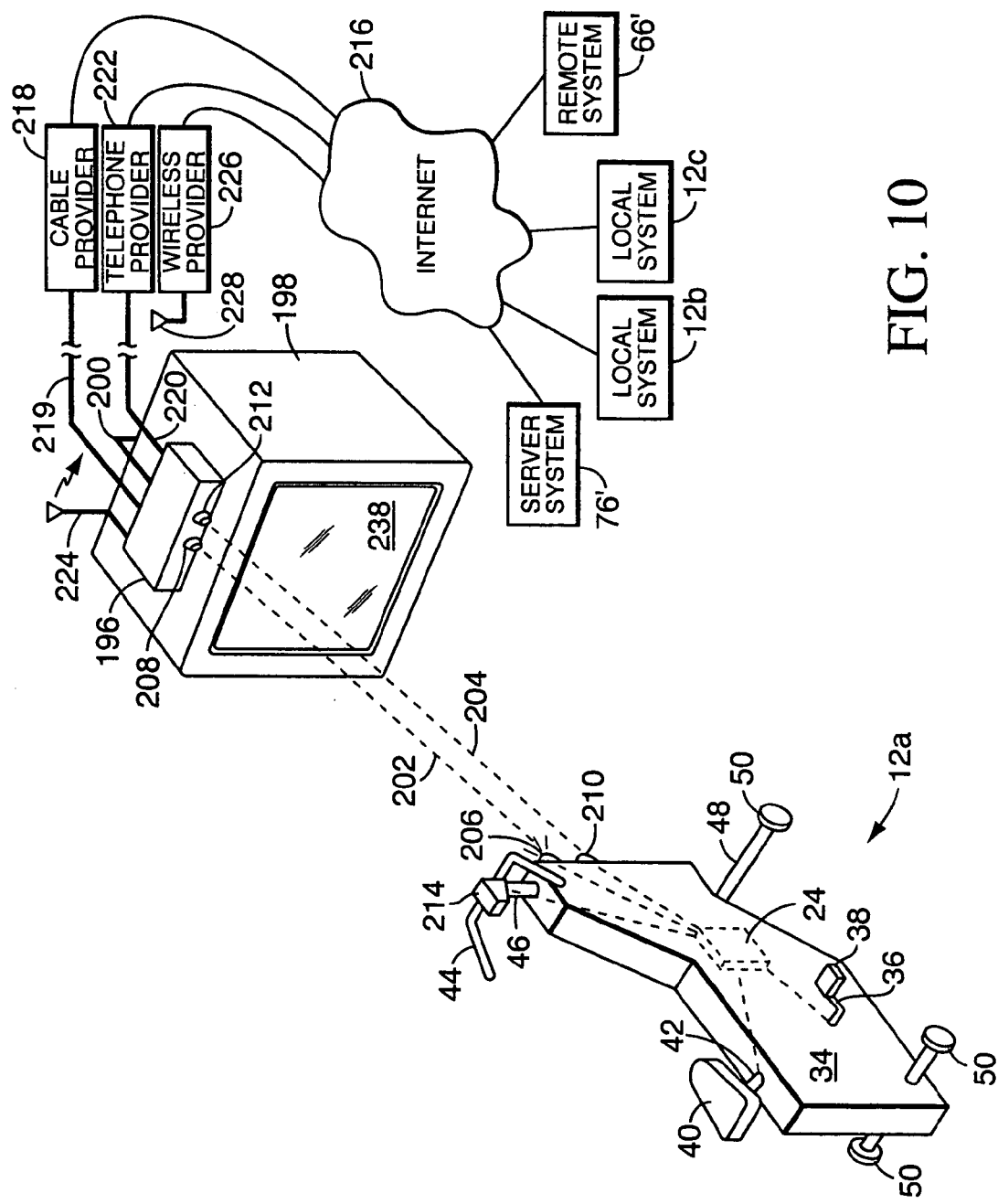
FIG. 10 is an illustration of a local system connected to other local systems, remote systems, and server systems via the Internet.

In FIG. 10, an Internet linked version of the present invention is illustrated. Those portions of the system that are similar to those previously described use the same reference numbers. It should be understood that while this embodiment is described in terms of the Internet, is also applicable to other forms of networking. However, a data packet network such as the Internet, or an Intranet, operating on a TCP/IP protocol is preferred.

In FIG. 10, a local system 12a is provided with an Internet access apparatus 196, and an enlarged video display such as a television 198. The television 198 can be any standard television (currently typically an analog television) which can develop an image provided over a cable or wire 200 from the Internet access apparatus 196. Internet access apparatus such as apparatus 196 are available from variety of vendors at the present time, and are generally referred to as a "set-top Internet boxes." Set-top Internet box 196 typically communicates with a user via Infrared (I/R) data linkages, such as I/R linkages 202 and 204. In the present invention, these linkages are used to communicate with the local system 12a, as will be appreciated by those skilled in the art. Some optimization of the software in the apparatus 196 may be preferable to communicate with the local system 12a, although standard apparatus 196 can also be used by having the local system 12a emulate a remote I/R unit or remote I/R keyboard.

Local system 12a includes an I/R transmitter 206 which produces an I/R beam 202 that can be detected by an I/R detector 208 of the Internet access apparatus 196. The local system 12a also includes an I/R receiver 210 which receives an I/R beam 204 generated by an I/R transmitter 212 of the Internet access apparatus 196. Techniques for communicating between electronic devices with I/R beams are well-known to those skilled in the art.

If a higher-bandwidth linkage or "link" is preferred between the local system 12a and the Internet access apparatus 196, a cable or the like can be provided to connect the two. Also, it will be appreciated by those skilled in the art that the Internet apparatus 196 is only one method for accessing the Internet, other methods including the use of personal computers, etc. Higher-bandwidth is likely to be desired if a video camera 214 is used to transmit video over the Internet.

The Internet access apparatus can be coupled to the Internet 216 by a number of communication linkages or "transmission media." For example, if the Internet access apparatus 196 includes a cable modem, a cable 217 can be coupled to an Internet server at a cable provider 218 to couple to the Internet 216. Alternatively, if the Internet access apparatus is provided with a standard modem, a telephone line 220 can be coupled to a Internet server at a telephone provider 222 to couple to the Internet 216. Finally, if a wireless modem is provided by Internet access apparatus 196 with an antenna 224, an Internet server at a wireless provider 226 with an antenna 228 can be used to couple to the Internet 216.

Also coupled to the Internet 216 are one or more local systems, such as local systems 12b and 12c, one or more remote systems 66', and/or one or more server systems 76'. Since the local, remote, and server systems are all coupled to the Internet 216, their hierarchy is more a logical hierarchy rather than a physical or wired hierarchy. In other words, the local systems can talk with each other and with the remote system 66, and the remote systems can talk with each other and with the server system 76 in a "logical hierarchy."

Figure 11:
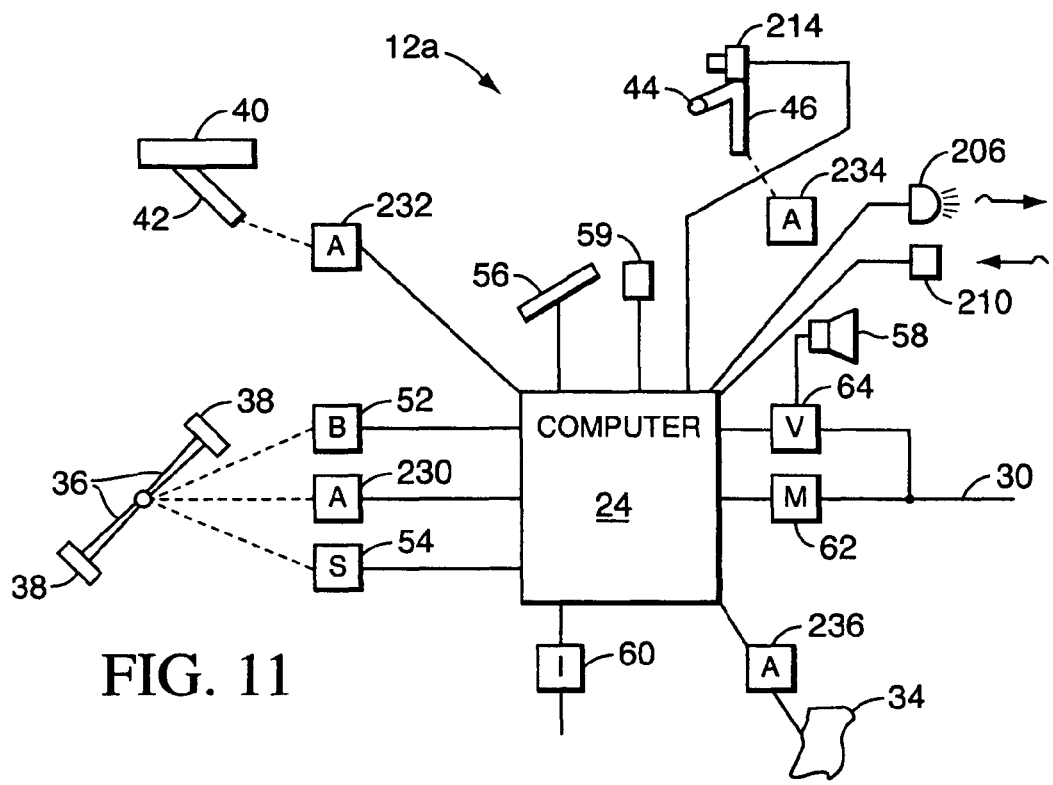
FIG. 11 is a block diagram of the local computer of the local system of FIG. 10.

In FIG. 11, a computer system 24 ("local computer") of local system 12a is illustrated in greater detail. As previously described, the local computer 24 can comprise the motherboard of a standard personal computer that has been programmed to perform the process of the present invention. Most of these processes have already been described, and will not be repeated here. The computer 24 is operative to control the I/R transmitter 206 and the I/R detector or receiver 210 to implement communication with the Internet access apparatus 196. As mentioned previously, these communication linkages can be augmented or substituted by other types of communication linkages, such as a higher-bandwidth cable or twisted pair linkage to the Internet access apparatus 196. In addition, the computer 24 can receive video data from a video camera 214 of the user. This video data can either be real time data, or a series of video "snapshots," e.g. a "frame" a video sent every few seconds. Preferably, if this video data is to be sent over the Internet, it is compressed by some form of standard compression algorithm, such as MPEG.

Also shown in FIG. 11 are a number of "active" actuators 220, 222, 224, and 226. These actuators are controlled by computer 24. Actuator 230 is coupled to the crank 36 of the pedal 38 to provide a tactile, haptic, or "force" feedback on the pedal 38. Likewise, actuators 232, 234, and 236 are provided to provide a tactile, haptic or "force" feedback on the stem 42 of seat 40, on the stem 46 of handlebar 44, and on the frame or enclosure 34 itself. Therefore, "real-world" forces such as hitting a rock, wind forces (which tend to exert the force on the handlebar 44) and others can be imparted on the user of the local system 12a.

The actuators 230-236 can be motors, solenoids, and other forms of force-producing mechanisms. They can be electrically, hydraulically, or pneumatically controlled, although electrically controlled actuators are preferred. It should also be noted that the actuators can also serve as sensors that can be "read" by the computer 24. Also, the actuators can be used to provide mechanical resistance. For example, the actuator 230 can eliminate the need for a friction-type brake 52. Also, the actuator 234, if of a suitable type, can be used to both sense the position of the handlebar 44 and to provide a force feedback on those handlebars.

Figure 12:
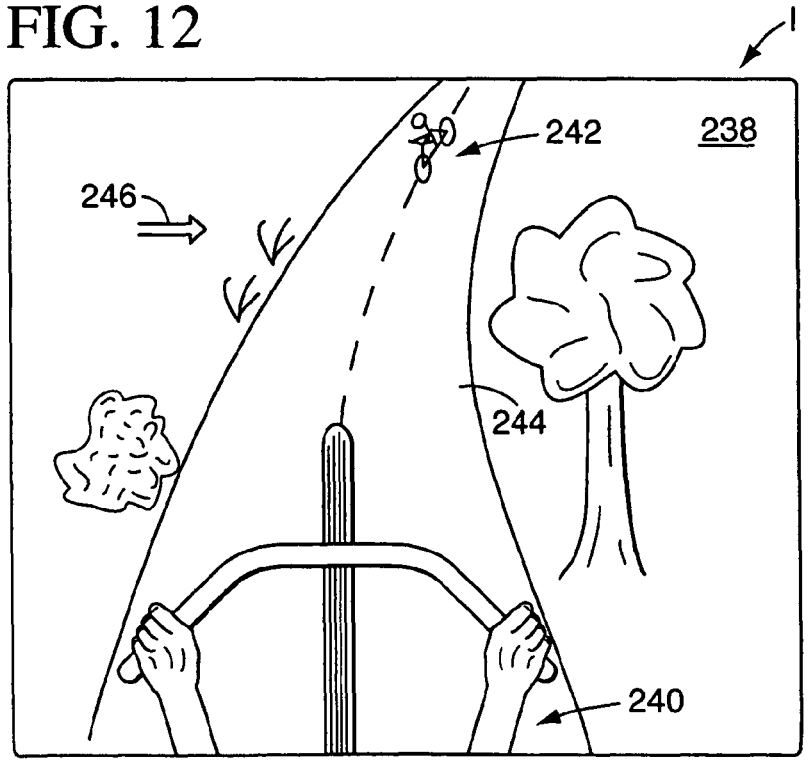
FIG. 12 is an illustration of a "virtual ride" taking place over the Internet with users using two separate local systems.

In FIG. 12, a "virtual exercise session" in a "virtual world" is illustrated. More particularly, an image I is developed on the screen 238 of the television 198 which simulates both the user 240 and one or more individuals 242. These one or more other individuals can be users at other local machines, or can be the "personal trainer" at another local system or at a remote system. In this instance, the user is riding a bicycle along a road 244 and is trailing behind the other user 242 also riding a bicycle. Through the use of the actuators, the user 240 can feel the surface of the road, can get a "boost" when going downhill and feel a "drag" as he goes uphill, can feel the affects of a wind 246, can feel the lessening of resistance to pedaling when "drafting," i.e. riding closely behind, the other user 242, etc. With the use of the video camera 214, an image of the other user 242 can be provided on the screen 238, e.g. pasted onto the cycling figure's body 242, as can be the image of the user 240 on the screen of the local system of user 242.

Of course, there are many "virtual worlds" that one or more users of the exercise apparatus can inhabit. For example, the user can be a standard gymnasium or health club, and wander from exercise equipment to exercise equipment while interacting with other user/exercisers and personal trainers in this virtual world. In consequence, the user 240 is motivated to exercise in much the same way as if he journeyed to a gymnasium or health club, without leaving the comfort and convenience of home.

Figure 13:
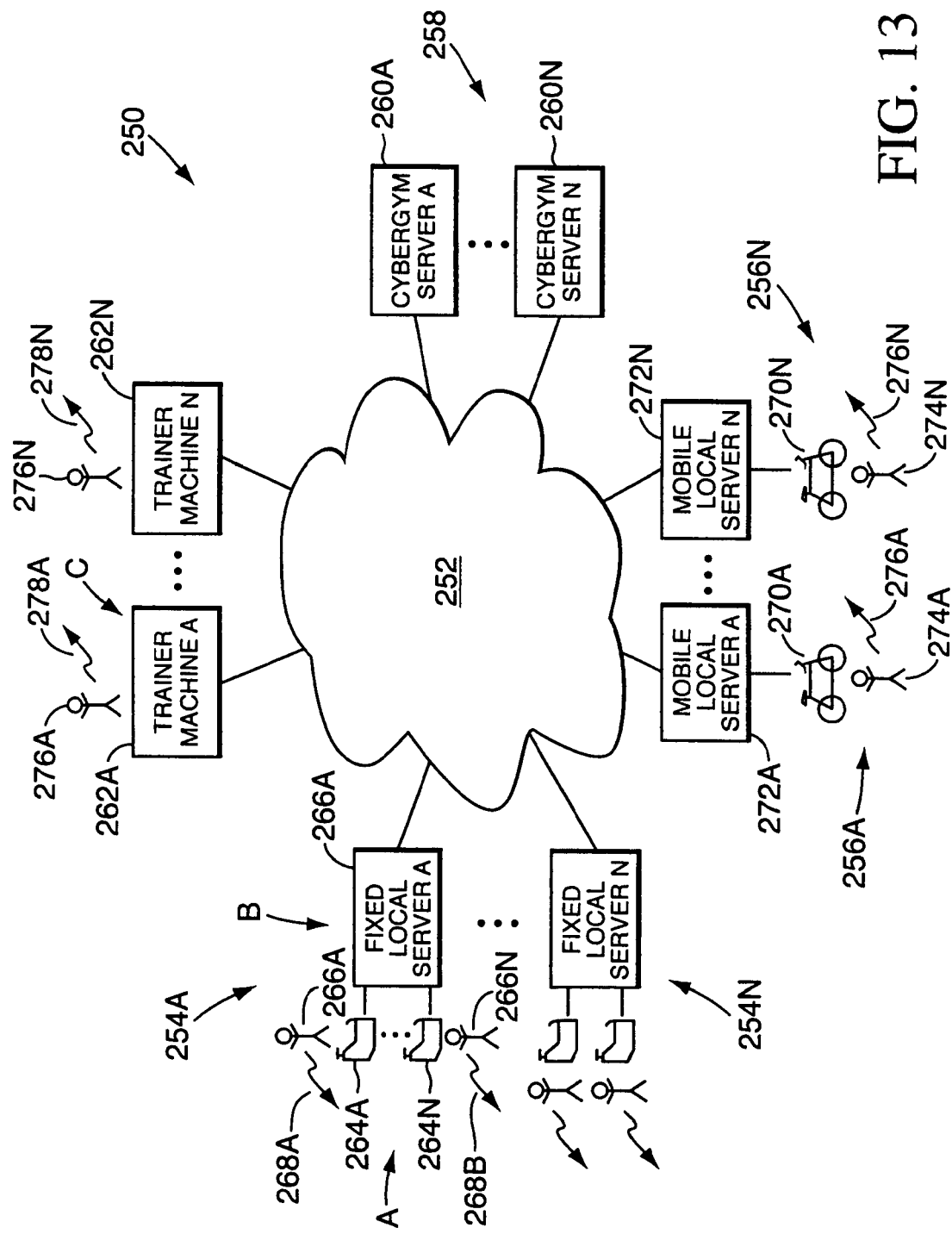
FIG. 13 is an illustration of a remote interactive exercise and health system in accordance with the present invention.

FIG. 13 illustrates a remote interactive exercise and health system 250 in accordance with a preferred embodiment of the invention. This embodiment, as was the case with the previous embodiments, may be implemented over a wide area network (WAN) such as the Internet 252. The remote interactive exercise and health system 250 preferably includes a number of fixed local systems 254A-254N and one or more mobile local systems 256A-256N. The system 250 also preferably includes a remote server 258 which can include one or more physical or "virtual" servers 260A-260N. The system 250 also includes one or more trainer machines 262A-262N.

A fixed local system, such as fixed local system 254A, typically includes one or more health and/or exercise devices (often referred to herein as simply "exercise devices", "exercise apparatus", etc.) such as exercise devices 264A-264N. These one or more exercise devices 264A-264N are associated with a fixed local server 266. Of course, additional fixed local servers can be implemented as will be appreciated by those skilled in the art. The exercise devices 264A-264N can be of a variety of types such as stationary bicycles, weight lifting machines, operation machines, treadmills, scales, etc. As a minimum, the exercise devices 264A-264N should include at least one sensor which permits data to be processed and sent to the remote server system 258 via the Internet 252. The exercise devices can also include passive devices such as scales, heart rate monitors, etc., which typically have an output dependent upon one or more sensors. It is preferable, but not essential, that the exercise device 264A-264N includes some type of feedback or actuator which mechanically influence the exercise device to vary the resistance, provide tactile feedback, provide haptic feedback, etc., to a user.

Typically associated with an exercise device is a user such as user 266A-266N. The users 266A-266N interact with the system 250 at least through the exercise devices 264A and 264N. Such interaction will be referred to herein as "in-band" interaction. However, the users 266A-266N can also interact with system 250 through "out-of-band" interactions 268A-268B. As will be discussed in greater detail subsequently, these "out-of-band" interactions do not necessarily go through the Internet 252. For example, a user 266A may be interacting with the fixed local server 266A on a separate, high speed data connection to provide real time video information to the exercise device 264A. Alternatively, the out-of-band interaction 268A could be a cellular phone conversation with a personal trainer.

Of course, out-of-band interaction can also be performed in-band. In a preferred embodiment of the present invention, an inexpensive controller and interface providing low-data rate "in-band" transfers for an exercise device is seen to be preferable. Such a controller will add only minimally to the cost of the exercise device (which typically needs a controller anyway), permitting manufacturers to provide the "in-band" compatibility on virtually their entire product line. This "in-band" transfer is primarily a transfer of sensor data (from the exercise device) and scripts and other data to the exercise device. Other, high bandwidth transfers, such as streaming video and audio, etc., can be accomplished with an add-on "out of band" device. For example, a head mounted display and earphones can provide an out of band experience. Nonetheless, other embodiments of the present invention utilizes a single, high-speed channel, such as an 802.11 protocol channel, to couple the exercise device to the rest of the system. Of course, this would require a much more complex controller, approaching the complexity of a personal computer, to be provided for the exercise device. If a suitably powerful controller were provided in the exercise device, then all data transfers could be "in-band."

Similarly, the mobile local systems 256A-256N typically include mobile exercise devices 270A-270N and mobile local servers 272A-272N. In this instance, there is usually a one-to-one correspondence between a mobile exercise device 270A and a mobile local server 272A. However, in alternate embodiments of the present invention, two or more exercise device 270A may be associated with a single mobile local server 272A by, for example, wireless connection. Often, the mobile exercise devices 270A include one or more sensors, such as an RPM sensor, a GPS sensor, an elevation sensor, an energy expended (wattage) sensor, a pulse rate sensor, an oxygen saturation sensor, etc. The mobile exercise devices 278A are typically not provided with actuators, although it is possible to do so. For example, a mobile bicycle can be provided with an actuator which would shift gears on the bicycle. Nonetheless, other feedback can be provided to a user of mobile exercise equipment 270A through the "in-band" and/or "out of band" connection, such as current location, advice from the trainer, etc., via, for example, a display on a bicycle computer. Again, associated with each of the mobile exercise devices 27A-27N are one or more users 274A-274N. These users can interact with the system 250 by the "in-band" experience and/or by an out-of-band experience 276A-276N. Again, these out-of-band experiences can be high speed data connections to the local mobile computer or true out-of-band experiences such as a cellular telephone conversation with the trainer.

The remote server 258 is in an at least part time communication with the local systems 254A-254N and mobile systems 256A-256N. As will be appreciated by those skilled in the art, the remote server system 258 can include one or more physical and/or virtual servers 260A-260N. This permits the easy scalability of the system 250 as more users and trainers use the system. Typically, the remote server system 258 is the intermediary for communication between local systems and trainer machines, but in alternate embodiments of the present invention, local servers may communicate directly with each other or through the Internet 252 or directly to a trainer machine through the Internet 252 or other transmission media, as will be appreciated by those skilled in the art.

The trainer machines 262A-262N are typically associated with individual trainers 276A-276N. The trainers may interact with the system 250 through in-band communication or may communicate with, for example, users 266A-266N and 274A-274N through out-of-band communication 278A-278N. Such out-of-band communication can be, as explained previously, cellular or telephonic communication with one or more users. Alternatively, streaming video and/or audio, video files, audio files, graphics, etc. can be provided to the user and/or the trainer through an in-band or out of band communications link. The trainer machines 262A-262N are preferably personal computer systems using the Microsoft Windows or Mackintosh operating systems, for example, and provided with a display screen, keyboard, and pointing device such as a mouse. Preferably, the interface between the trainers 276A-276N is a World Wide Web (WWW) type interface. For example, a web browser such as MICROSOFT EXPLORER or NETSCAPE NAVIGATOR can be used on the trainer machines 262A-262N to access a secure website on the remote server system 258, as will be explained in greater detail subsequently.

The present system is well suited for franchise and multi-level marketing systems. Trainers can buy a franchise, or operated as an independent contractor, and sell memberships to users. A user can then either buy or lease a local system, along with the service provided by the trainer. As trainers obtain too many clients for them to personally manage, they can create sub-franchiser or sub-contractor trainers for some of the clients. The top level trainers will not only obtain compensation for each of their direct clients, but they will also obtain a smaller share of the compensation for their indirect clients through the sub-franchiser or sub-contractors. Trainers can also be sponsored, e.g. by a company for its employees.

Figure 14:
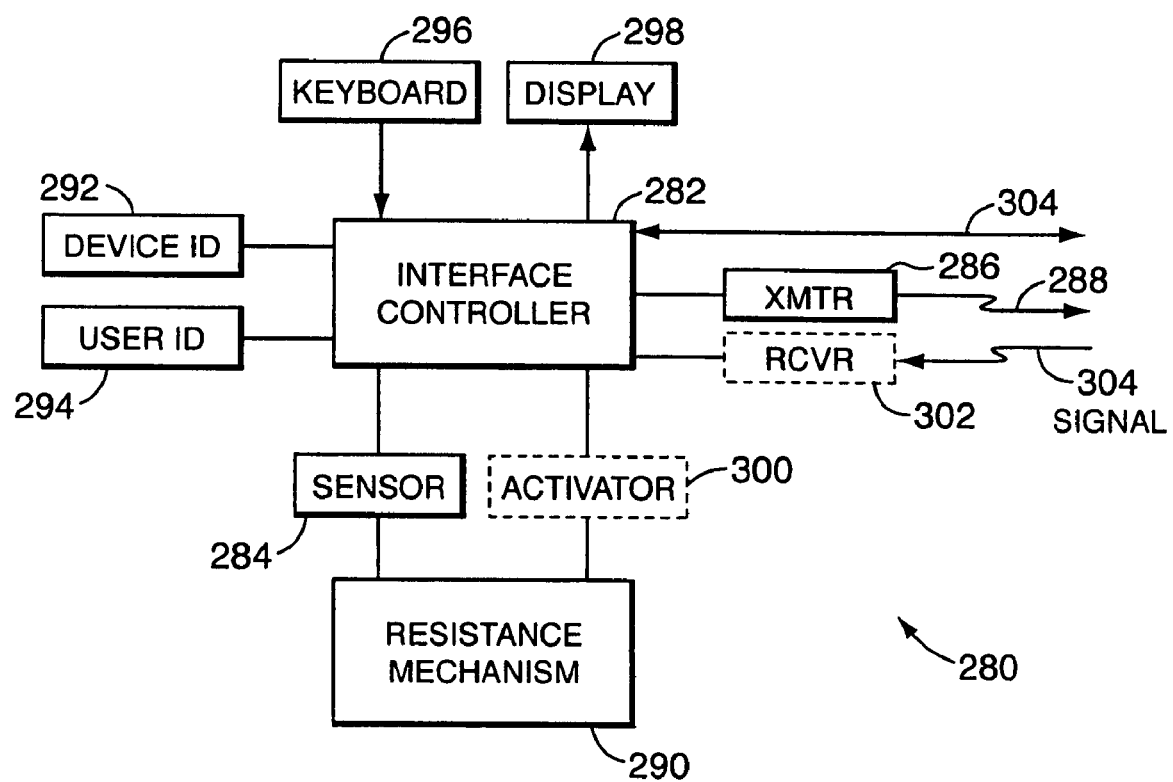
FIG. 14 is a block diagram of a preferred control circuitry for an exercise device of the system illustrated in FIG. 13.

FIG. 14 is a block diagram of an exercise device circuit which can be associated with, for example, an exercise device 264A-264N or 270A-270N. More particularly, an exercise device controller 280 includes an interface controller 282, a sensor 284, and a transmitter 286. By "transmitter" 286, it is meant that the appropriate drivers are provided to create a signal 288 which can be transmitted to a local server via wired, optical, wireless, or other transmission media. The sensors 284 are preferably coupled to a resistance mechanism or actuator 290. The interface controller preferably also includes a device ID 292, a user ID 294, switches and keyboard 296, and a display 298, such as a flat panel display. The controller 280 can also optionally include an actuator 300 and a receiver 302. The receiver 302, like the transmitter 286, can receive a signal 304 via a variety of transmission media including wired, wireless, optical, fiber optic, etc.

A reason for "in-band" base functionality is to make the basic controller ubiquitous to exercise equipment. By making the base functionality whereby interaction with the sensors and actuators of the exercise equipment is supported, but not necessarily high-bandwidth interactions, the controller can be made very inexpensively and put into almost any exercise device with electronic circuitry. The more expensive circuitry for high-bandwidth interactions can be provided separately with the "out of band" capabilities of the present invention.

The interface controller 282 is preferably an integrated microcontroller having microprocessor, RAM, EPROM, and various interfaces. Alternatively, the interface controller can be implemented with discrete components. The purpose of the interface controller is twofold, namely to interact with the sensor and/or actuator of an exercise device and to provide communication interfaces to a user and to other portions of the remote interactive system 250. It is desirable that the interface controller be relatively low cost so they can be added to each piece of manufactured exercise device such that the interface become ubiquitous.

In addition to communicating with sensor 284 and actuator 300, the interface controller 282 can provide a display on display 298 to enhance the exercise session for the user. The display can provide internally developed parameters such as RPM (in the example of a stationary bicycle), it can also display information provided by, for example, the trainer via the system 250. The keyboard 296 is used to input various user commands into the system.

Preferably, each exercise device is provided with a device ID 292. This identifies the particular device to the system 250. In one preferred embodiment, the device ID is stored in an EPROM internal to the interface controller 282. In other embodiments of the present invention, the device ID can be provided by dip switches or other coding mechanisms that can be read by the interface controller 282.

Also preferably, each user is provided with a user ID 294. This permits a user to use any piece of compatible equipment by entering his or her user ID, such that the system 250 knows that he or she is using that exercise device. The user ID can be provided through the keyboard 296, or can be provided in the form of a physical key that can attach, for example, to a keychain. Magnetic keys which can store a user ID 294 are well known to those skilled in the art.

Communications between the interface controller and the rest of the system 250 through the transmitter 286 and the optional receiver 302 comprise "in-band" communication. However, there can also be out-of-band communication signals 304 between the controller 280 and, for example, a local server 266A. These "out-of-band" signals can include, for example, high speed data communication to provide real time video (e.g. streaming video over the Internet) on the display 298.

Figure 15:
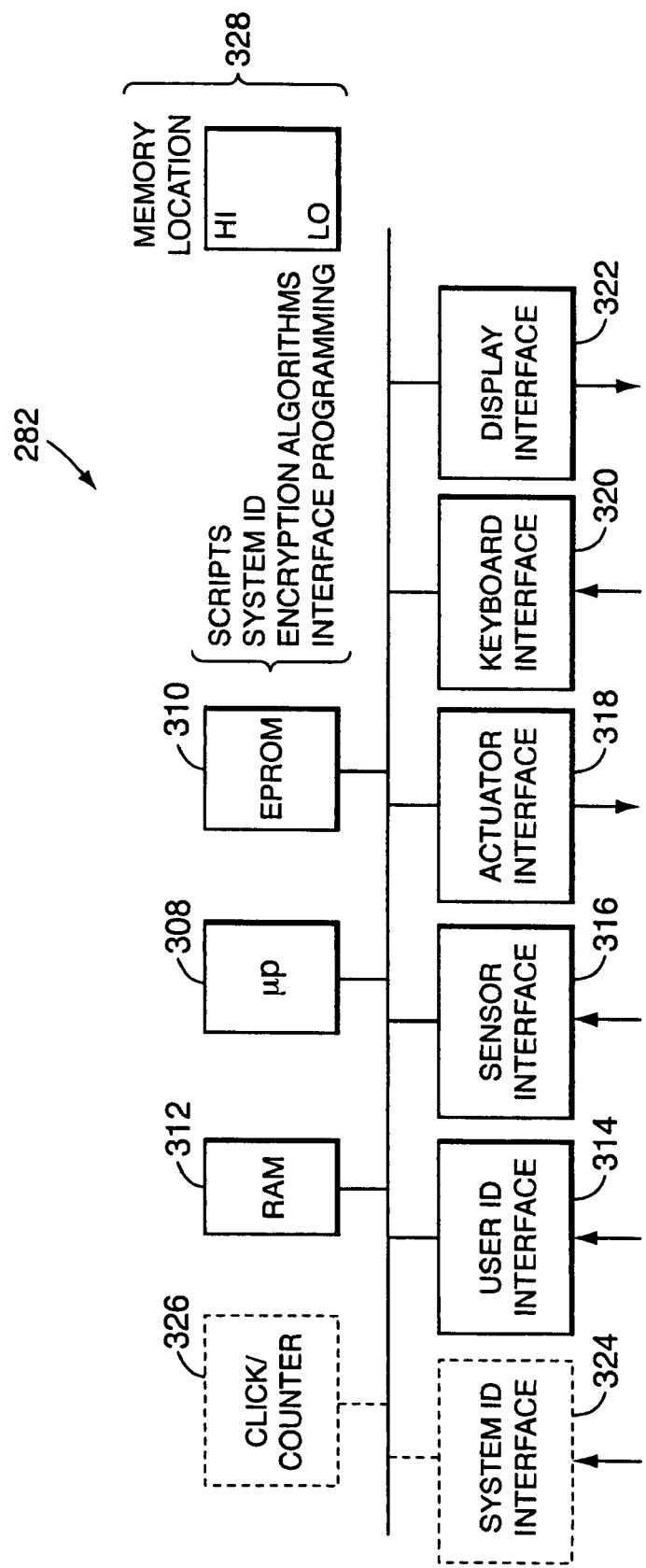
FIG. 15 is a block diagram of a preferred architecture for an interface of FIG. 14.

FIG. 15 is a block diagram of an exemplary interface controller 282 of this invention. The interface controller 282 preferably includes a system bus 306 which interconnects a number of components such as a microprocessor 308, an EPROM 310, RAM 312, and a number of interfaces 314-322. Optionally, the interface controller 282 can include a system ID interface 324 and a clock/counter 326, both of which would also be coupled to bus 306.

In certain embodiments, it is preferable that as many as the components of controller 282 as is possible are integrated into a single device. For example, the microprocessor, RAM, and EPROM, as well as a number of the I/O devices, can be integrated into a single chip. The EPROM can be EEPROM which allows the electrical reprogramming of the EPROM. Alternatively, the controller 282 can be made from discrete devices.

The EPROM 310 includes the program instructions for the controller 282. These program instructions will be described in greater detail with reference to FIGS. 16, 17, 18 and 19. Also, preferably, this system or device ID can be stored in the EPROM 310 during factory installation. The RAM 312 is used as "scratch pad" memory by the microprocessor and can serve as a buffer for the various I/O devices. The EPROM 310 and the RAM 312 comprise the primary memory for the controller 282 which may have a memory map as indicated at 328. In this exemplary illustration, interface programming, encryption algorithms, system ID, and scripts are mapped into memory locations ranging from low (LO) memory to high (HI) memory.

The various input/out (I/O) devices include a user ID interface 314, a sensor interface 316, an actuator interface 318, a keyboard interface 320, and a display interface 322. The primary direction of data flow is indicated by the arrow to each of these I/O devices. That is, the user ID interface provides user ID information to the system 282, and is therefore primarily an input device. Likewise, sensor interface 316 and the keyboard interface 320 primarily provide information to the system 282 and therefore are also input devices. The actuator interface 318 and the display interface 322 "display" will provide outputs from the controller 282 and, therefore, are primarily output devices. As will be appreciated by those skilled in the art, input devices include analog-to-digital circuitry (A/D), while output devices include digital-to-analog (D/A) circuitry.

As noted above, a preferred embodiment of the invention stores the system ID in the EPROM 312. However, it may also be desirable to have a system ID provided externally to the controller 282 via system or device ID interface 324. This would more securely couple the device ID to the physical device, such that the controller 282 or EPROM could not be removed and placed on another exercise device. Also shown is an optional clock and counter, which in a certain embodiments is a real time clock. The clock/counter 326 is used to time various intervals, such as sleep mode, pulling schedules, etc.

Figure 16:
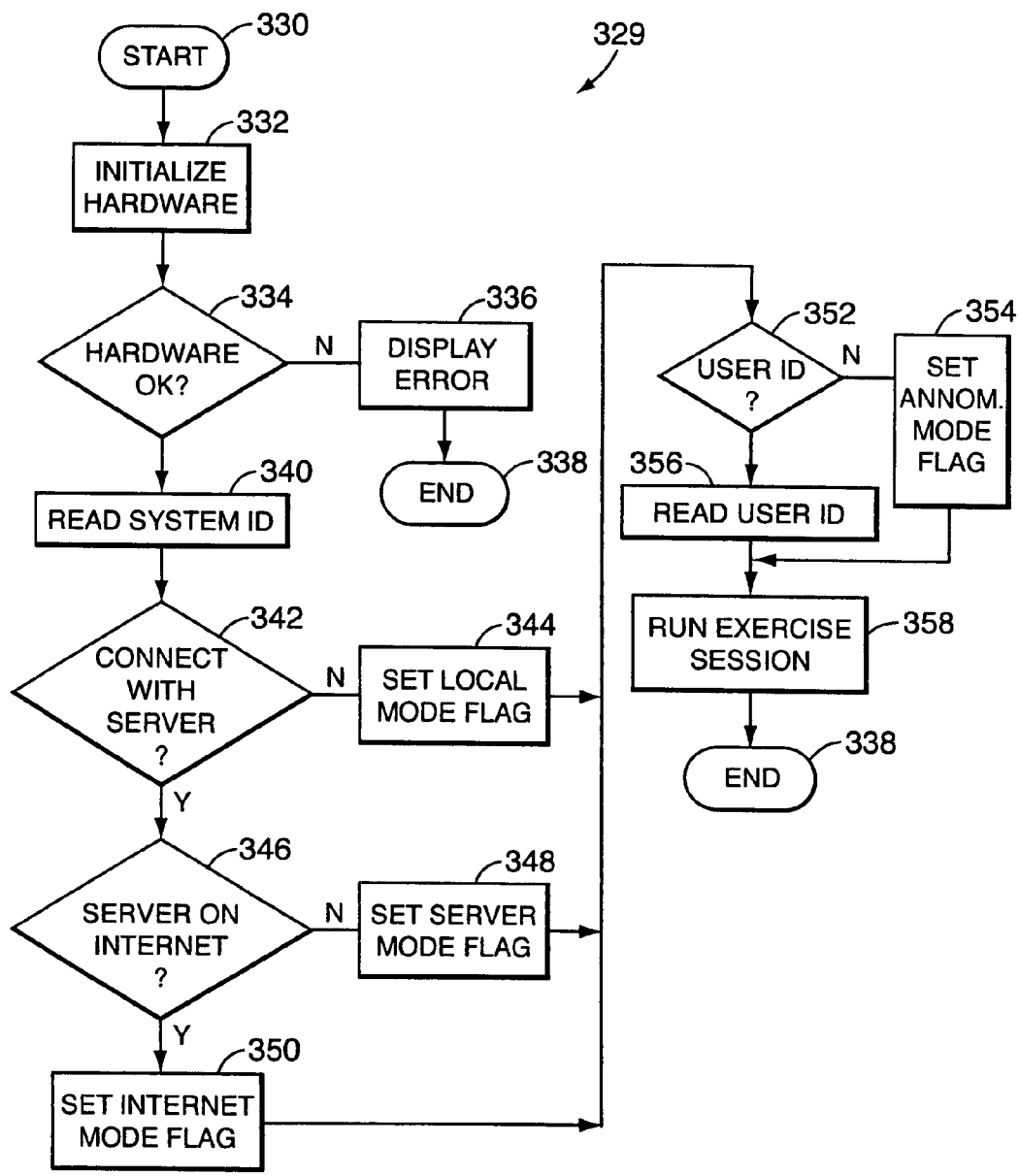
FIG. 16 is a flow diagram of a process executed by the microprocessor of FIG. 15.

FIG. 16 illustrates part of the interface programming stored in the EPROM 310 of FIG. 15. More particularly, a process 329 is implemented on the controller 282 which begins at 330 and, in an operation 332, the process initializes the hardware. As will be appreciated by those skilled in the art, this involves the writing to certain registers and the initialization of counters and other variables in the controller 282. Next, in an operation 334, it is determined whether the hardware is operating correctly. This is typically accomplished under microprocessor 308 control wherein data is written to and read from memory and various buffers, and wherein commands are sent to the various I/O devices to see if they operate correctly. If the hardware check is not okay, an error is displayed in operation 336, preferably on the display 298 of the exercise device controller 280. The process then ends at 338. However, if the hardware is determined to be functional, an operation 340 reads the system ID. Next, in operation 342, the controller 282 of an exercise device, for example 264A, attempts to connect with a local server, such as server 266A. If it does not successfully connect with the server, a "local mode" flag is set to indicate that there is no server connection. If the controller 282 does connect with the server, an operation 246 determines whether the server is on the Internet. If the server (such as a server 266A or 272A) is not connected to the Internet, an operation 348 sets the server mode flag to indicate the server is not on the Internet. If operation 346 determines that the server is on the Internet, an operation 350 sets an Internet mode flag.

Next, an operation 352 determines if there is a user ID. The invention can work in either an user identified mode, or in an unanimous mode. If there is no user ID as determined by operation 352, an operation 354 sets an anonymous mode flag. If there is a user ID, an operation 356 reads the user ID for use by the system. Finally, the exercise session is run in an operation 358 and the process ends at 338.

Figure 17:
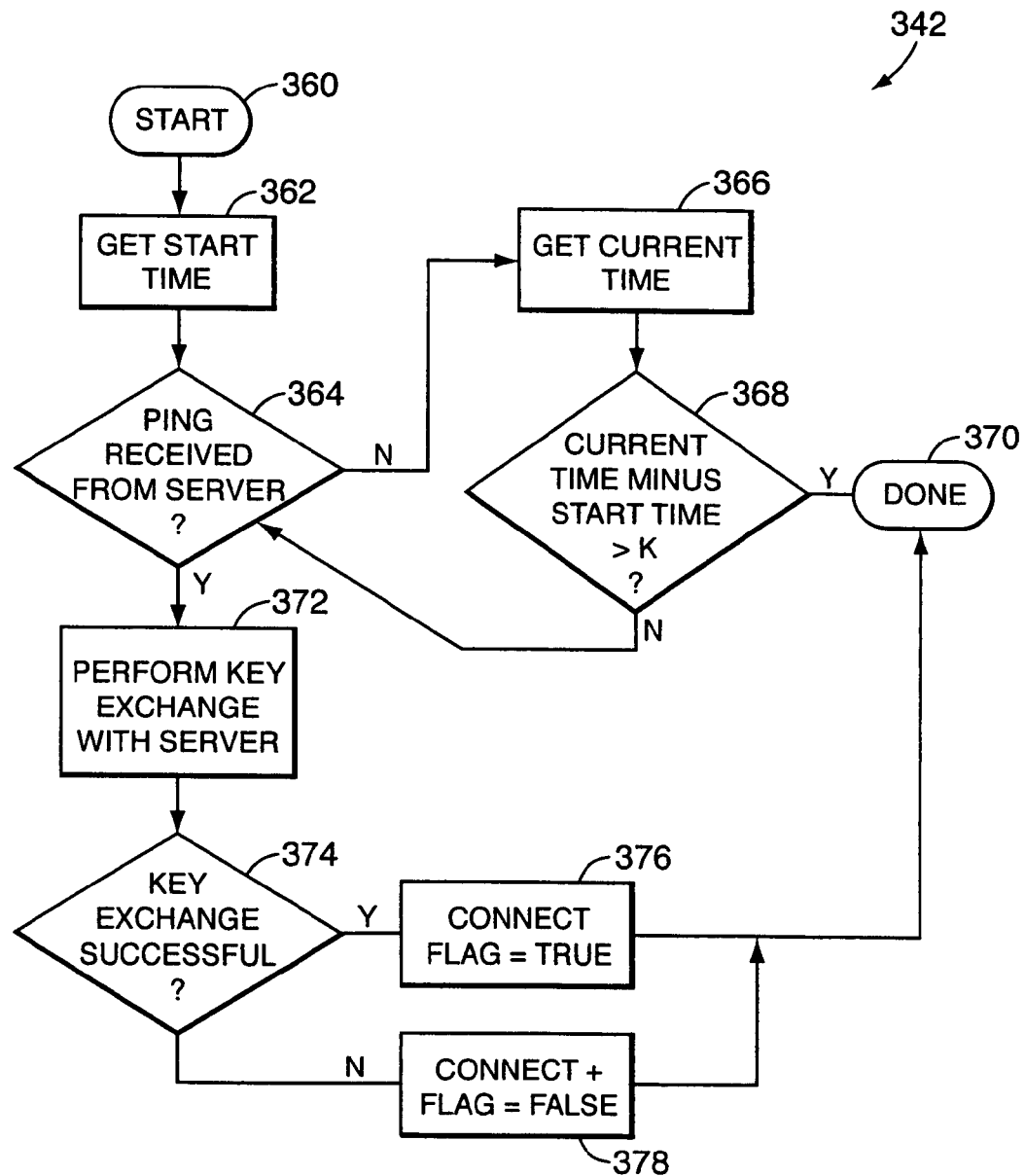
FIG. 17 is a flow diagram illustrating the "Connect with Server?" process of FIG. 16 in greater detail.

In FIG. 17, the process "Connect with Server?" 342 of FIG. 16 is illustrated in greater detail. Process 342 begins at 360 and, in operation 362, the start time is obtained and stored. Next, in operation 364, it is determined whether a "ping" is received from the server. By "ping" it is meant that a message is sent from the server and addressed to the exercise device having the primary purpose of determining whether the exercise device is active or "alive." If operation 364 does not receive a ping from the server, the current time is obtained in operation 366 from, for example, the real time clock 226, and an operation determines whether the difference between the current time and the start time is greater than a constant K. If it is, the process 342 has "timed out" and the operation is complete at 370.

If a ping has been received from the server as determined by operation 364, an operation 372 performs a key exchange with the server. As will be appreciated by those skilled in the art, this key exchange should be secure using one of several well known key exchange algorithms. For example, the well-known Diffie-Hellman algorithm is suitable. In one embodiment, the server can encrypt its key with a first encryption code, send it to the exercise device which then adds its own key and encrypts the entire package with its own encryption. The doubly-encrypted packet is then sent back to the server which decrypts with its encryption code, removing its own key and encrypting the encrypted packet including the key of the exercise device. The encrypted packet is then sent back to the exercise device to remove its encryption and, finally, the encrypted packet is then sent back to the server where it is decrypted by the server to remove the exercise devices key. Thus, by using multiple transmissions, the keys can be securely exchanged without broadcasting any unencrypted data.

Process 342 continues at operation 374 where it is determined whether the key exchange was successful. If it was successful, a connect flag is set to true in an operation 376 and the process 342 is completed at 370. Otherwise, the connection flag is set to false in operation 378, and the process is likewise completed.

Figure 18:
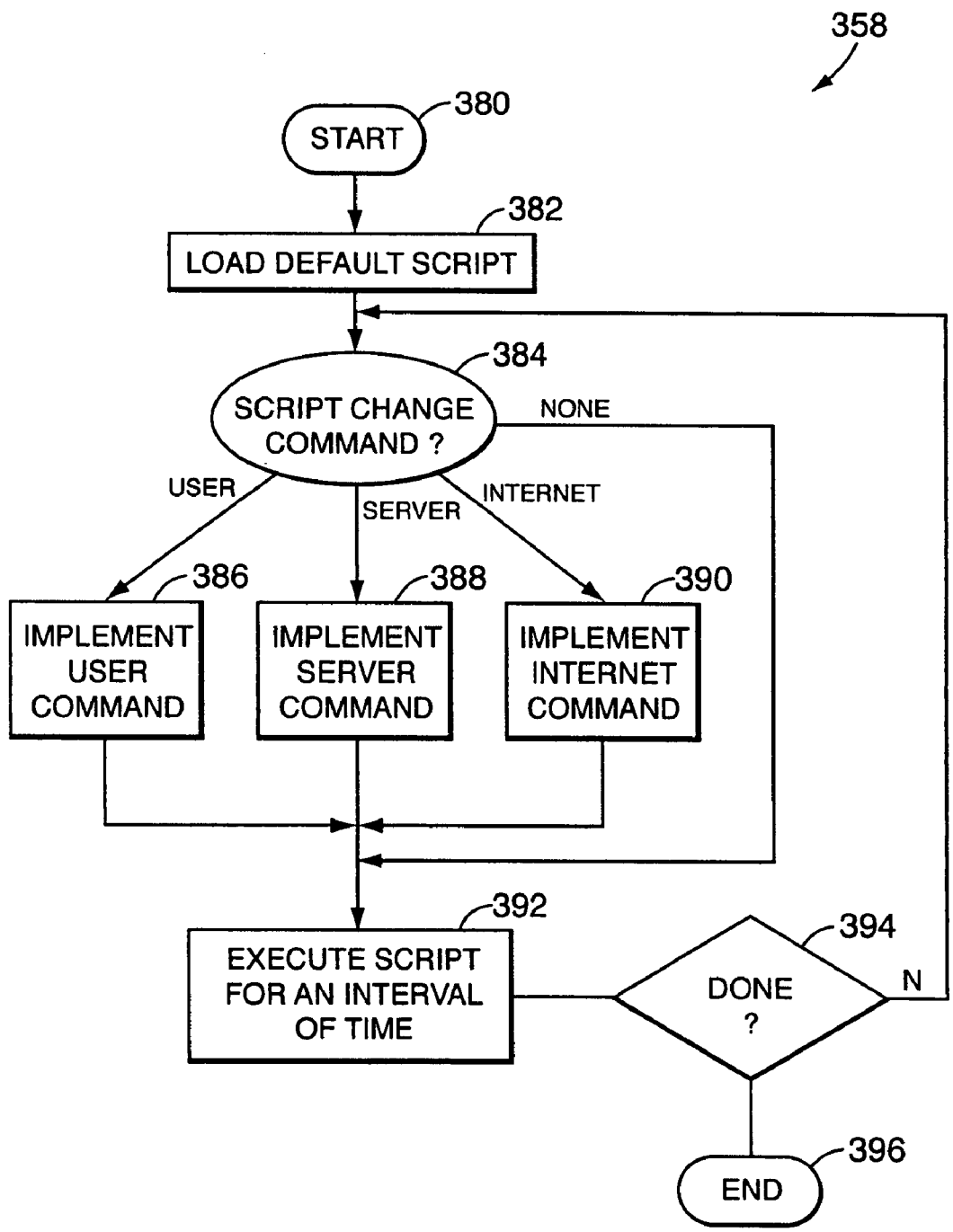
FIG. 18 is a flow diagram illustrating the "Run Exercise Session" process of FIG. 16 in greater detail.

In FIG. 18, the process "run exercise session" 358 of FIG. 16 is illustrated in greater detail. The operation 358 begins at 380 and, in an operation 382, a default script is loaded. Next, in an operation 384, it is determined whether there is a script change command. These script change commands are preferably (but not necessarily) of at least three different types. A first type of script change command is a user script change command which is implemented in an operation 386. A second type of script change command is a server script change command which is implemented in an operation 388. A third type of script change command is an Internet script change command which is implemented in an operation 390.

After the implementation of one of the script change commands in operations 386, 388, or 390, or in the absence of a script change command, an operation 392 executes the script on the exercise device for an interval of time. An operation 394 determines whether the process is done, and, if not, process control is returned to operation 384 to look for additional script change commands. Otherwise, the process is completed at 396.

As used herein, a "script" is a sequence of data or commands which can be used to influence the operation of the exercise equipment. Therefore, a script can be a computer program, such as a Java Applet, or it can be a proprietary script language which is interpreted by the controller of the exercise equipment, or it can be a string of data or parameters, (e.g., duration, level, scaling, etc.), that is acted upon by the controller to influence the operation or use of the exercise device. It will therefore be appreciated that the term "script" broadly encompasses the locally executed functionality in the exercise equipment controller to influence the operation of the exercise device. Of course, as will be appreciated by those skilled in the art, portions of the "script" can be distributed, for example, to the local server or, via the Internet, to one or more systems, sensors, or machines connected to the Internet.

Figure 19:
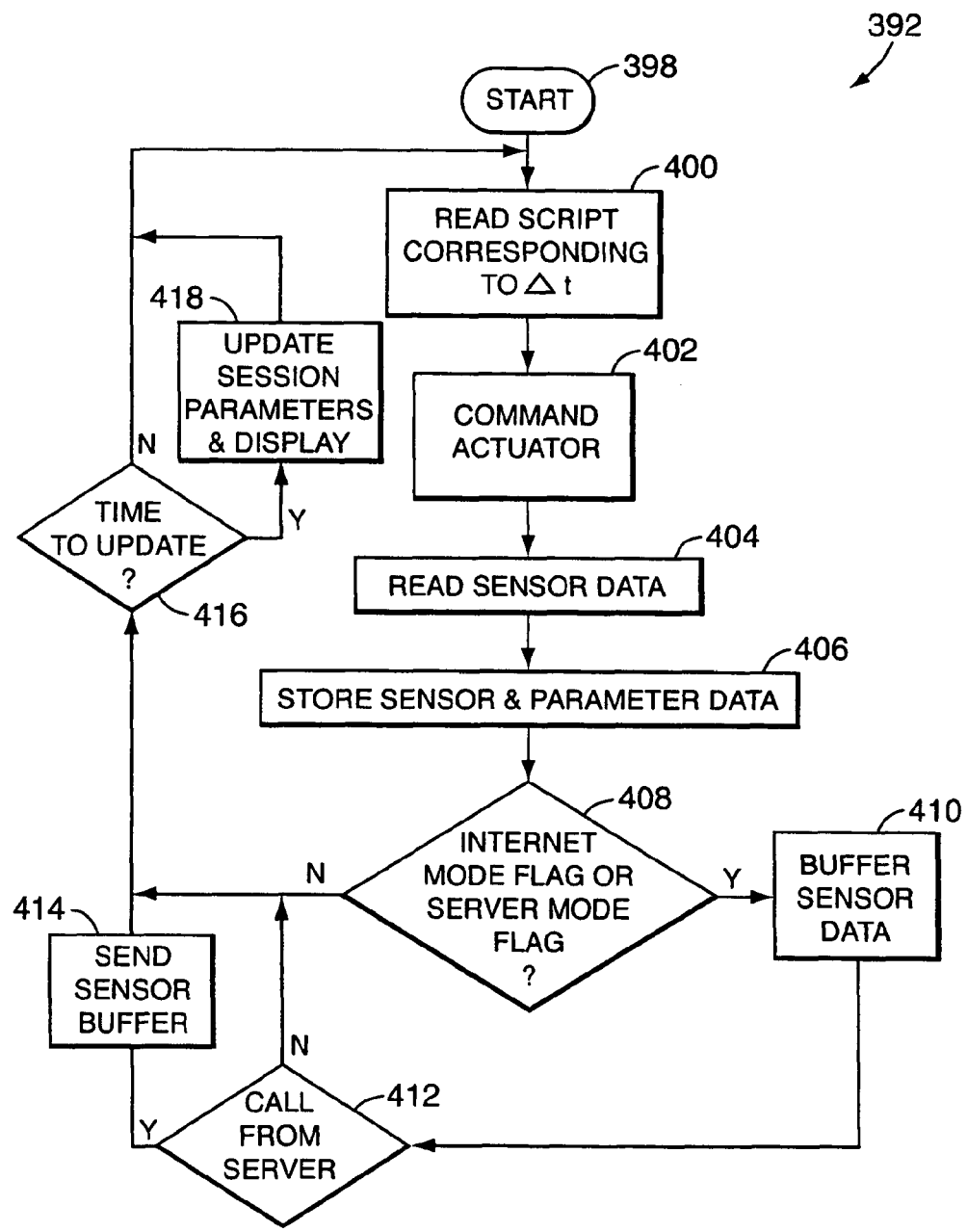
FIG. 19 is a flow diagram illustrating the "Execute Script" process of FIG. 18 in greater detail.

FIG. 19 is a flow diagram illustrating the "executed script" operation 392 of FIG. 18 in greater detail. Operation 392 begins at 398 and, in an operation 400, the script is read according to a time interval .DELTA.t. In an operation 402, any actuator is sent its command, and in an operation 404, any sensor data is read. As will be appreciated by those skilled in the art, an actuator command is typically accomplished by placing data in an output buffer of the actuator interface which is then converted by D/A converters to analog signals which can control the actuator. As will also be appreciated by those skilled in the art, the reading of sensor data is typically accomplished by reading a sensor data buffer in the sensor interface which was produced by taking analog signals produced by the sensor and digitizing them with a A/D converter. The sensor and parameter data are stored in an operation 406 for later reference and processing. This data can typically be stored in buffers provided in the RAM Memory 312.

Next, an operation 408 determines whether there is an Internet mode flag or a server mode flag. If so, the sensor data is buffered in operation 410. An operation 412 then determines whether there is a call from the server and, if so, the sensor buffer is sent to the server in an operation 414. If there is no Internet mode flag or server mode flag or after the completion of operations 412 and 414, an operation 416 determines whether it is time to create an update. If so, an operation 418 updates the session parameters and the display. That is to say, the session parameters are updated in a memory store, such as RAM 312, and a display is provided such as on display 322. Process control then returns to operation 400. The process 392 continues to operate until an interval of time has elapsed at which time operation 392 ceases and operation 394 on FIG. 18 takes process control.

Figure 20:
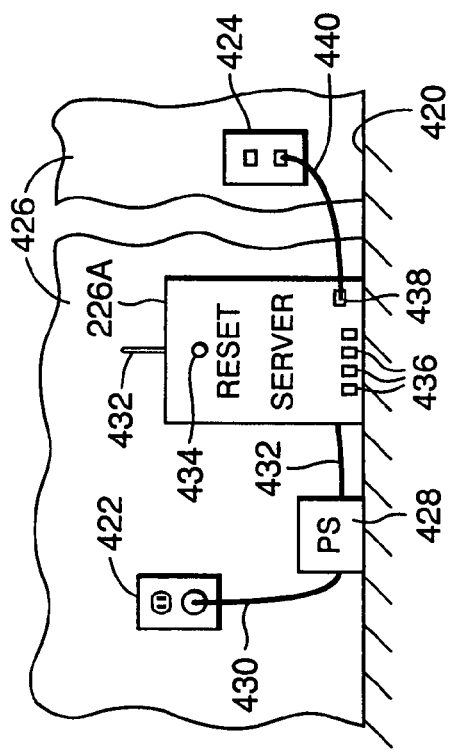
FIG. 20 is an illustration of a fixed local server of FIG. 13.

In FIG. 20, a fixed local server 266A is graphically illustrated. In this embodiment, the server 266A sits on a floor 420 between an electrical outlet 422 and a telephone outlet 424, both of which are provided in a portion of a wall 426. In this embodiment, the server 266A is provided with an external power supply 428, which also sits on the floor 420. The supply power 428 has a cord 430 which plugs into one of the sockets of electrical outlet 422 and has another cord 432 to provide DC power to the server 266A.

The server 266A is preferably provided with an antenna 432, a reset button 434, a number of exercise device connection sockets 436, and an Internet connection socket 438. In a preferred embodiment of the invention, the server 266A communicates with the exercise devices wirelessly through radio transmission emanating from antenna 432, for example. In a wireless system, the transmitter 286 and receiver 302 of controller 280 in FIG. 14 are radio frequency transmitters and receivers. Alternatively, the server can communicate with the exercise devices by other wireless communication forms, such as infrared communication. Still further, the server can communicate with the exercise devices via a hard wire, coaxial cable, fiber optic cable, etc., connection through one of the exercise device connection sockets 436. Likewise, while the server 266A is shown to be coupled to the telephone outlet 424 by a telephone cable 440, the server 266A could also make an Internet connection through wireless devices, such as a radio modem. Further, while the outlet 424 is described as a "telephone" outlet, it will be appreciated that it also represents other hard wire and/or wireless connections to the Internet including DSL, Ti lines, fractional Ti lines, etc. That is, the telephone outlet 424 represents either an analog or digital signal connection between the outlet and the Internet which could actually be implemented by a number of different protocols.

In certain embodiments of the present invention, the human-computer interface of the local server is kept as simple as possible. For example, one embodiment of the invention the server has only a reset button as an interface. This makes the server "appliance-like" and therefore very easy to use. In other embodiments of the present invention, more complex human-computer interfaces such as a touch-screen display providing a menu of options can be provided. The wireless embodiments of the present invention also help in the appliance-like nature of the local system, as well as its scalability. For example, a new exercise device can be added to a local system by simply bringing it into proximity to the local server and hitting the reset button of the local server, and an exercise device can be removed from the local system in a similarly easy fashion. One exercise device or many exercise devices can be associated with a local server in a very scalable manner. Further, many local servers, trainer machines, and remote servers can be added to the system in a scalable fashion.

Figure 21:
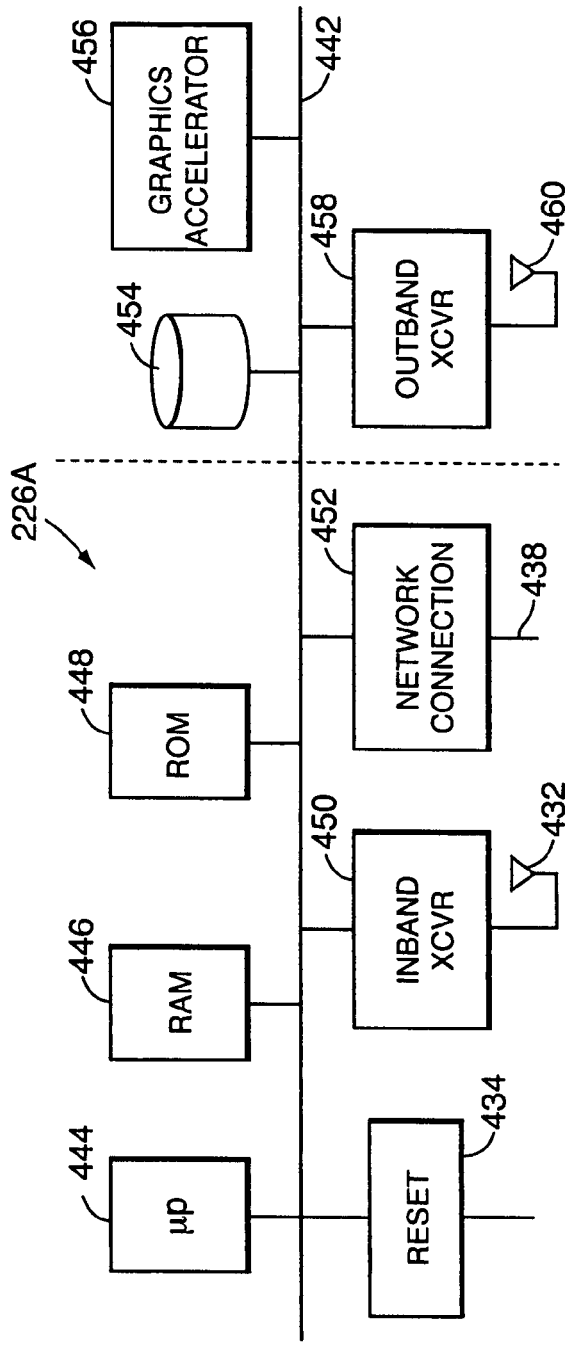
FIG. 21 is a block diagram of the server illustrated in FIG. 20.

In FIG. 21, the server 226A includes a typical computer architecture including a bus 442 to which is a coupled a microprocessor 444, random access memory (RAM) 446, read only memory (ROM) 448, as well as a number of peripherals 434, 450 and 452. The microprocessor 444, RAM 446, and ROM 448 are relatively center components and they are available from a variety of manufacturers. However, it is preferable to have the microprocessor 444 be an Intel compatible Pentium class processor so that it can run standard operating instrument systems such as the Linux operating system. Preferably, a journaling file system such as Reiser FS would be used so that the integrity of the file system would be preserved in the event of a sudden power failure. For simplicity, the RAM 446 should be static RAM (SRAM) and the ROM 448, depending on the implementation, may be an EPROM.

The reset button 34 is coupled to the bus 442 by appropriate interface circuitry such that a reset command can be sent to the microprocessor 444. An in-band transceiver 450 is coupled to the bus 442 to send and receive electromagnetic radiation (radio signals) via the antenna 432. The in-band transceiver 450 communicates with the in-band transmitter 286 and the in-band receiver 302 of 614. The network connection 452 couples the bus to the Internet socket 438. Depending on the type of Internet connection, the network connection 452 may take a variety of forms. For example, the network connection 452 can be a modem and the Internet connection is by regular telephone line. Alternatively, the network connection can be an Ethernet connection for connection to a digital line such as a DSL or T1 line. As is well known by those skilled in the art, the network connection is configured for the appropriate connection type.

In an expanded version of the server 226A, there is also provided a mass storage device such as a hard disk drive 454, a graphics accelerator 456, and an out-of-band transceiver 458. The addition of an hard disk drive is desirable and then it supports standard operating systems such as the Linux operating systems. Of course, other operating systems could be supported such as Windows NT, Unix, etc. However, the Linux operating system is particularly well suited for this application since it is inexpensive (free), easily configurable, and well suited for Internet connection applications. The hard disk drive can also serve as a local store for scripts, programs, commands, buffered items, graphics, video and audio informations, etc. The graphics accelerator 456 is useful for graphically driven outputs which, in a preferred embodiment, would be sent to a user by an out-of-band transceiver 458. For example, the user could use a wireless, headmounted display with display screens in front of each of his or her eyes as well as ear phones. This type of information is of too high of a bandwidth for the preferred, low bandwidth in-band transceiver 450, but could be handled by an out-of-band transceiver 458 transmitting on an antenna 460. By providing this form of out-of-band communication, high quality and stereo video information could be sent to a user, as well as high fidelity and stereo audio information. This information can be viewed on a television screen, a computer monitor, a headmounted display, a display associated with the exercise device, etc., by way of the out-of-band transceiver. While the out-of-band transceiver is shown to be wireless in this embodiment, it will be appreciated by those skilled in the art that the out-of-band transceiver can also be a wired transceiver such that connection media such as electrical wire, coaxial cable, fiber optic, etc., can be used. Further, other forms of wireless transmission and reception can be used with the out-of-band transceiver 458 as well, including, but not limited to, I/R transmission and/or reception. Of course, all communication can be "in band" if the investment is made in the hardware necessary to support high-bandwidth communication. For example, the exercise equipment controller can include sufficient processing and peripheral power to utilize 802.11 wireless interconnections, which would provide enough bandwidth for completely "in-band" communications in certain embodiments of the invention.

Figure 22:
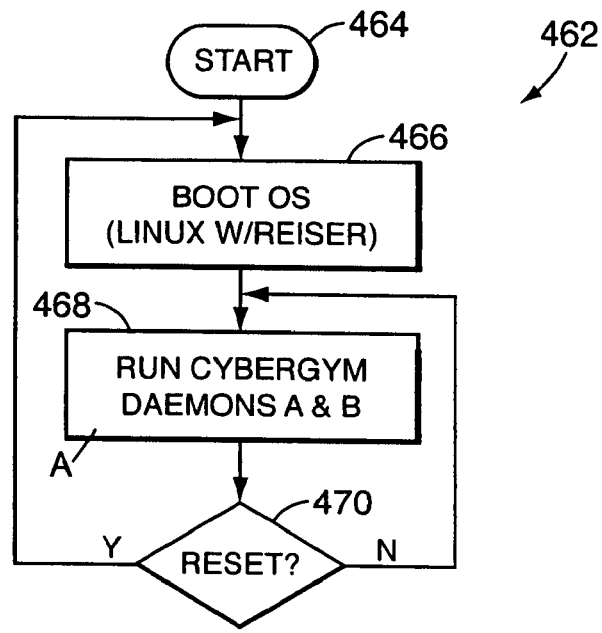
FIG. 22 is a flow diagram of a process implemented by the microprocessor illustrated in FIG. 21.

FIG. 22 illustrates the server operating system 462 which is implemented on the server 226A. The operating system begins at 464 with power on and, in an operation 466, the operating system is booted. As mentioned previously, a preferred operating system is Linux, which is a public domain operating system. Preferably, the Linux is provided with Reiser FS to prevent power up and power down glitches. The booting of an operating system, including Linux with Reiser FS, is well known to those skilled in the art. Next, in an operation 468, one or more daemons are executed. In this example, two daemons are run including Cybergym Daemon A and Cybergym Daemon B. As well known to those skilled in the art, a daemon is a process which runs substantially without interaction with the end user. An operation 470 determines whether there has been a reset based upon the pressing of a reset button 434 of FIG. 20 and, if so, the entire system is reset by turning over operational control to operation 466. If there is no reset command, the Cybergym daemon continues to operate.

Figure 23:
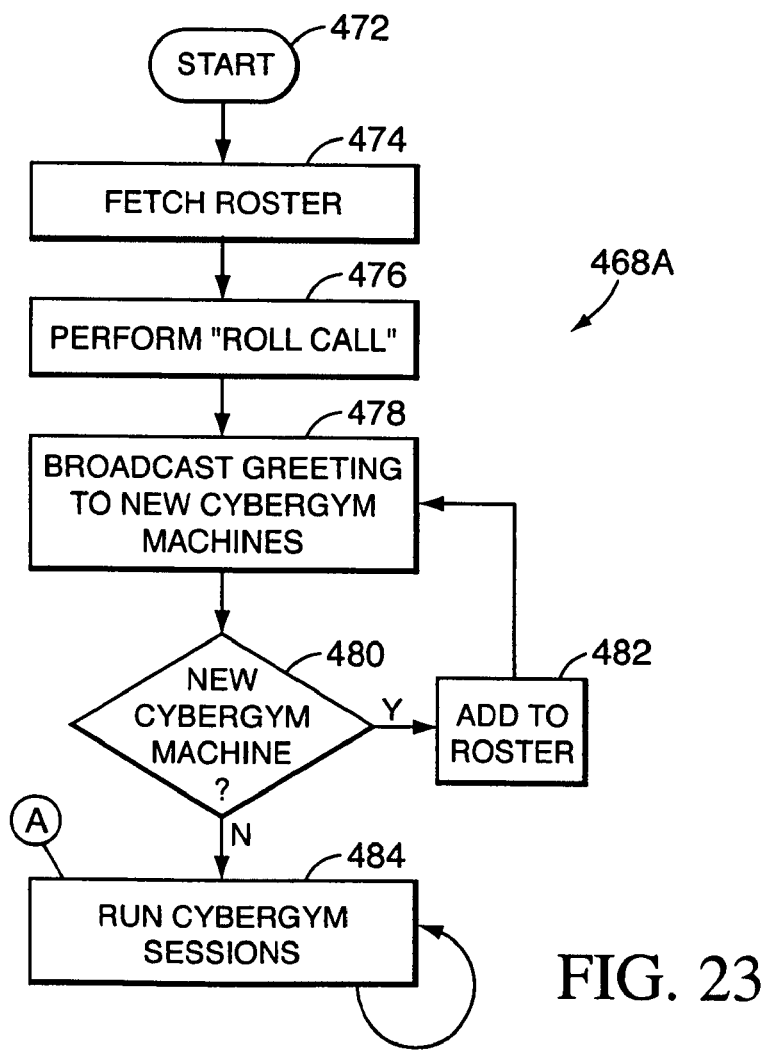
FIG. 23 is a flow diagram of the "Run Cybergym Daemon A" of FIG. 22.

In FIG. 23, the running of Cybergym Daemon A as part of process 468 is illustrated in greater detail. The process 468 begins at 472 and, in an operation 474, the roster is fetched. As used herein, a "roster" is a list or the like of all exercise devices that are "known" to this server. That is, a server only communicates with a known list or "roster" of exercise devices, aka "client machines." Next, the server performs a roll call of the exercise devices on its roster in an operation 476. If an exercise device which is on the roster does not respond despite repeated attempts, it is eventually removed from the roster. If the exercise device does respond, it is told to go to sleep, and is checked off on the roster that it met the roll call. Next, in an operation 478, there is a broadcast greeting to new CYBERGYM machines, i.e., to new exercise devices which may have been brought within connection range to the server. If a new Cybergym machine is detected in an operation 480, it is added to the roster and the broadcast greeting is again sent until the operation 480 does not attack any new exercise devices. At that point, the Cybergym sessions begin to execute with operation 484.

Figure 24:
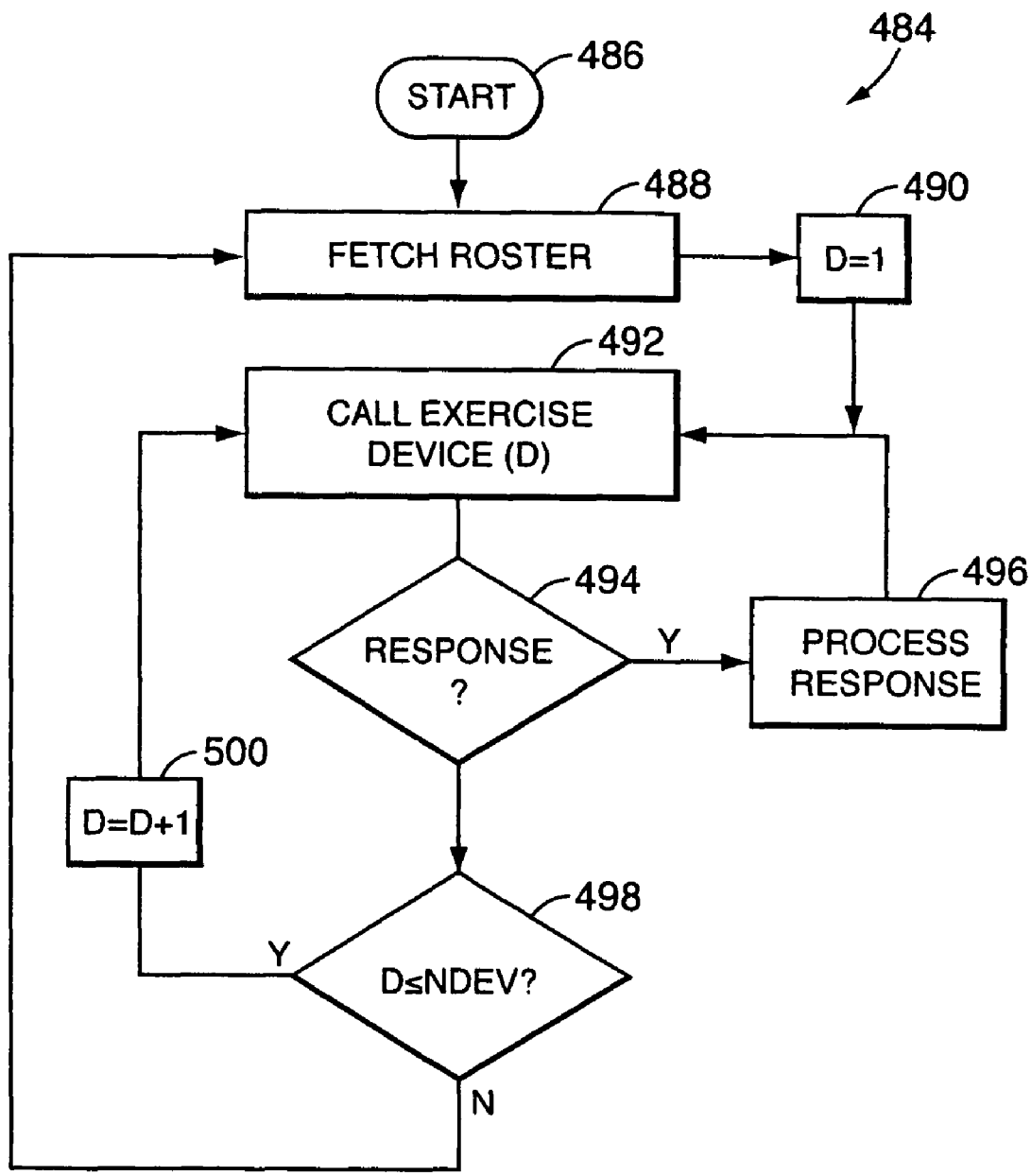
FIG. 24 illustrates the process "Run Cybergym Sessions" of FIG. 23 in greater detail.

FIG. 24 is a slow diagram illustrating the "Run Cybergym Sessions" process 484 of FIG. 23 in greater detail. Process 484 begins at 486 and, in an operation 488, the roster is again fetched. A counter D is initialized to 1 and in operation 490 and then exercise device number D is called. If exercise device (D) responds as determined by an operation 494, the response is processed in an operation 496 and process controller is returned to operation 492. If there is no response from the exercise device (D), it is determined whether all of the devices in the roster has been called in operation 498. That is, the variable D is compared to the value NDEV and, if it is less than or equal to NDEV (the number of devices in the roster), the variable D is increased by 1 in an operation 500 and operation control is return to 492. If the entire list has been called, operation control is returned to 488 to fetch the current roster.

Figure 25:
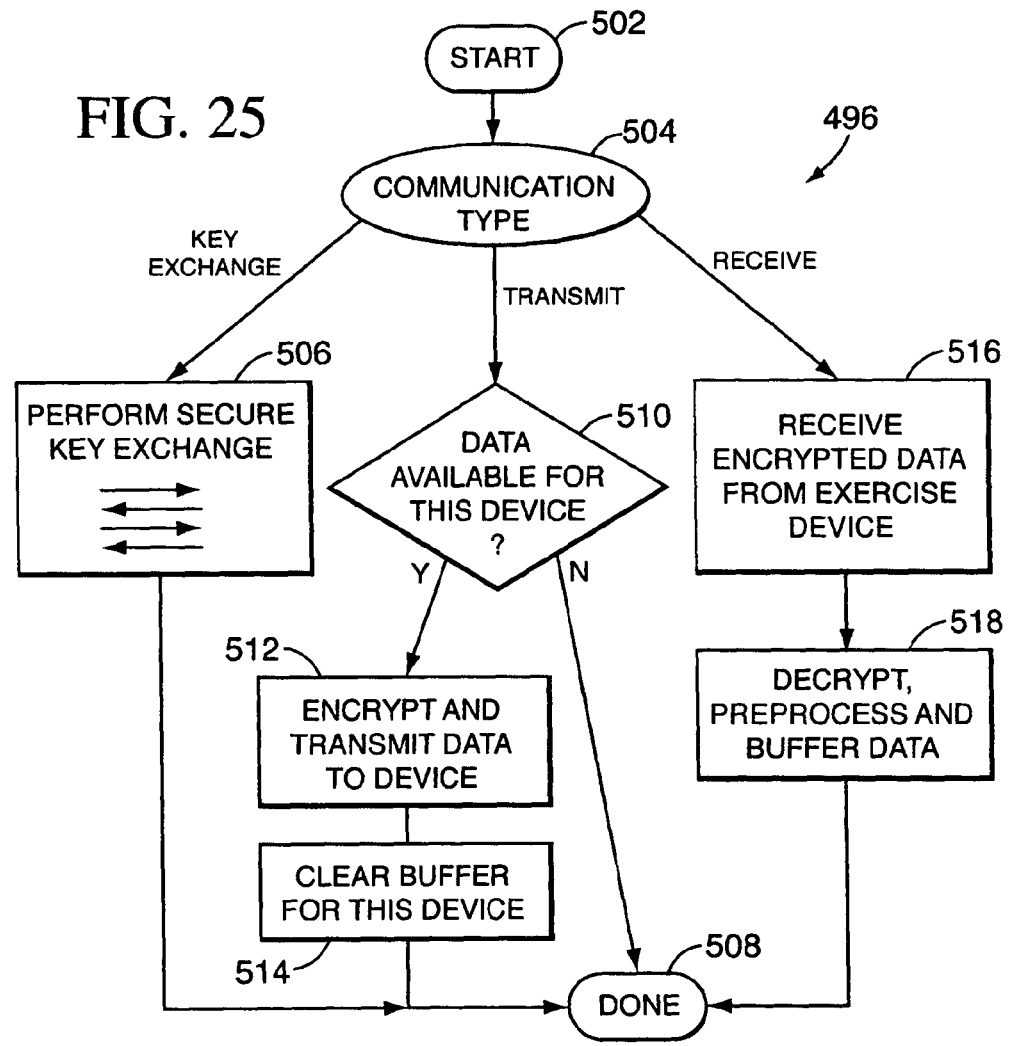
FIG. 25 is a flow diagram illustrating the "Process Response" operation of FIG. 24 in greater detail.

FIG. 25 illustrates the "process response" operation 496 of FIG. 24 in greater detail. More particularly, process 496 begins at 502 and, in an operation 504, the communication type is determined. If it is a key exchange communication type, an operation 506 performs a secure key exchange by one of a variety of methods, as was explained previously. The process is then completed at 508. However, if the communication type as determined by operation 504 is transmit, an operation 510 determines whether there is data available for this device. This is typically determined by looking in a lookup table associated with a buffer. If there isn't any data available, then the process is completed at 508. Otherwise, the data is encrypted and transmitted to the device in an operation 512. Once the data has been transmitted to the device and, preferably, the device is indicated that the data has been received and decrypted properly, the buffer is cleared for that device in an operation 514 and the operation is completed at 508. If the communication type is "receive", an operation 516 receives encrypted data from the exercise device. Next, the encrypted data is decrypted, preprocessed, and buffered as appropriate. The process is then completed at 508.

Figure 25A:
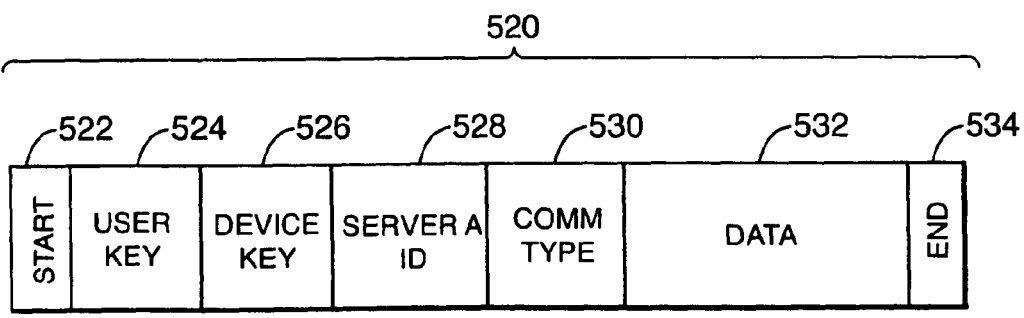
FIG. 25A is an illustration of a transmitted data packet in accordance with the present invention.

FIG. 25A illustrates an exemplary data packet sent in the transmit and receive operations that were discussed with reference to FIG. 25. In this instance, to send and receive packets are in the same format, although this is not necessarily the case in all embodiments of this invention. In this one exemplary illustration, the data packet 520 has a set of start bits which are typically a recognizable pattern for a receiving device. Next, the user key is transmitted in portion 524 of the packet, the developer's key is provided in the portion 526 of the packet, the server ID is provided in the portion 528 of the packet, and the communication type is provided in portion 530 of the packet. In this example, following the communication type is a portion 532 which contains data. This data portion can be a fixed length or a variable length as will be appreciated by those skilled in the art. Finally, an end portion 534 of the data packet 520 signals the end of the packet.

Figure 26:
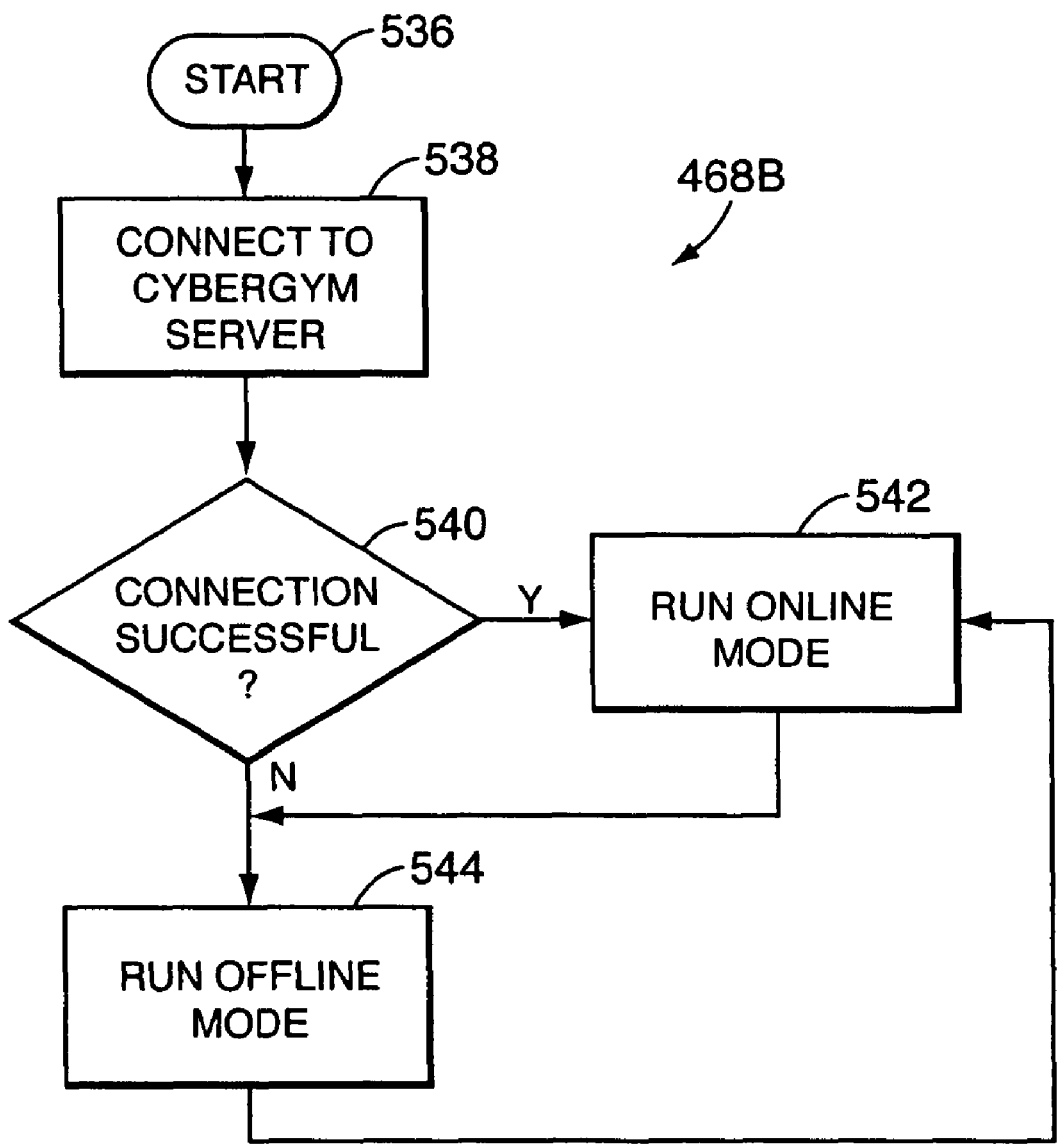
FIG. 26 is a flow diagram of the "Run Cybergym Daemon B" of FIG. 22.

In FIG. 26, the "Run Cybergym Daemon B" process 468 is illustrated in greater detail. More particularly, process 468B begins at 536, and, in an operation 538, there is an attempted connection to the Cybergym server. If, in operation 540, it is determined that the connection to the server with the Internet was successful, process 468B will run in online mode. The process 468B will continue to run on the online mode 542 until the Cybergym server can no longer be accessed over the Internet, at which time process control will be turned over to operation 544 to run in an offline mode. This operation 544 is also evoked when the connection to the server is not successful as determined by operation 540. The process 468B will continue to run in the offline mode in operation 544 until an Internet connection to the server is again re-established, at which time operation control will be turned over to operation 542 to run in an online mode.

Figure 27:
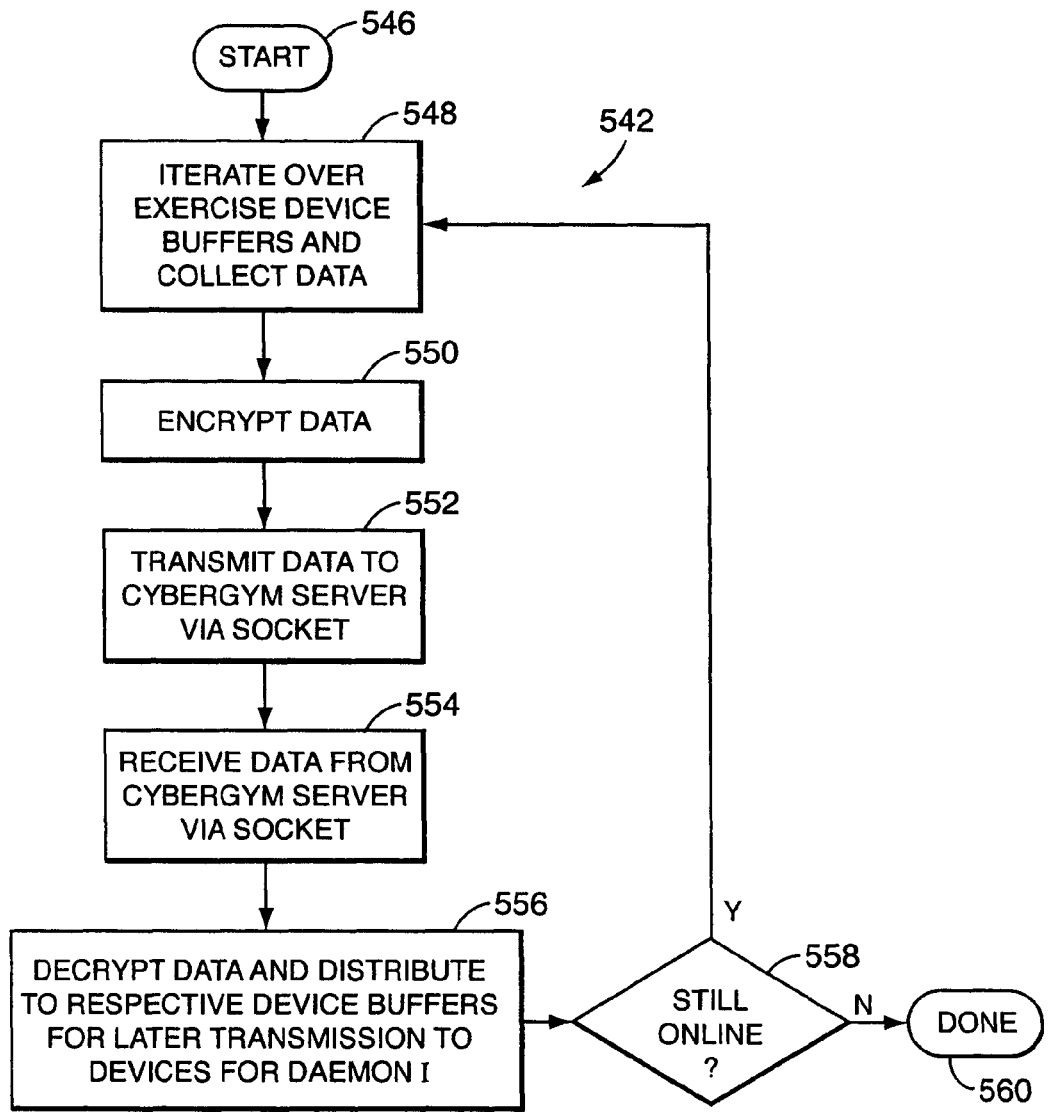
FIG. 27 is a flow diagram illustrating the "Run Online Mode" process of FIG. 26 in greater detail.

FIG. 27 is a flow diagram illustrating the "run online mode" process 542 of FIG. 26 in greater detail. The process 542 begins at 546 and, in an operation 548, the system iterates over the exercise device buffers and collects data. That is, each of the exercise devices will have a buffer region for the storage of its data. Next, in an operation 550, the data is encrypted. There are, of course, many suitable encryption techniques, although public key encryption is preferred in general. Public key encryption technologies are well known to those skilled in the art and are available both commercially and in the public domain (example, PGP encryption technology). Next, in an operation 552, the data is transmitted to the Cybergym server via a socket connection. As is well known to those skilled in the art, a socket connection takes care of much of the housekeeping overhead in the transmission of data. For example, sockets typically take care of the buffering functions, etc., that implement and facilitate the transfer of data. Next, data is received from the Cybergym server via the socket. An operation 556 decrypts the data and distributes it to respective device buffers for later transmission to the devices via the process 596 as best seen in FIG. 25. Finally, an operation 558 determines whether the Cybergym server is still online. If it is, process control is returned to operation 548. If not, the process 542 is completed at 560.

Figure 28:
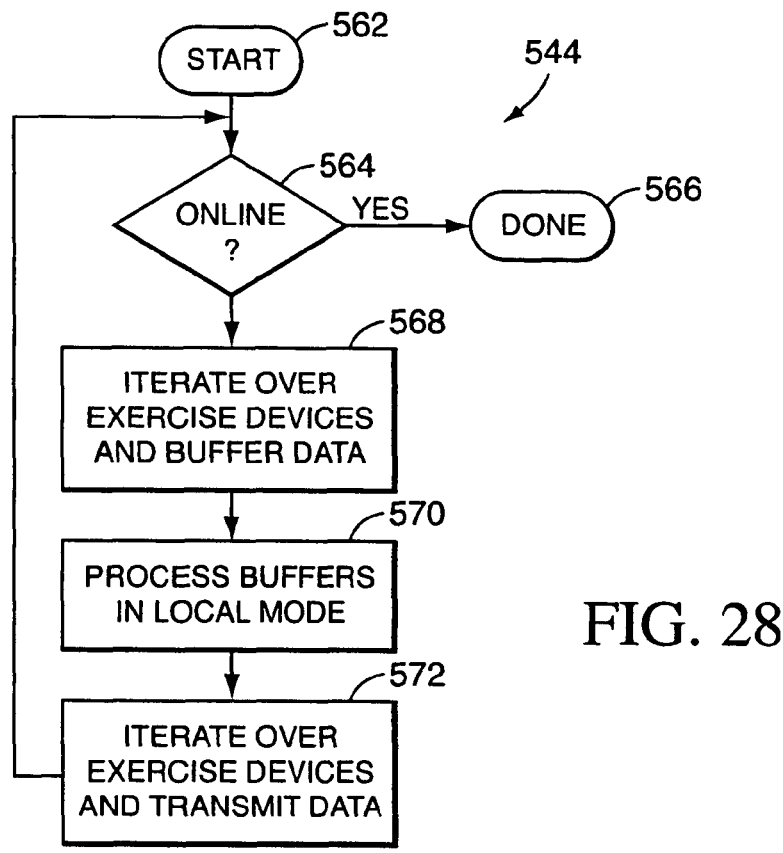
FIG. 28 is a flow diagram illustrating the "Run Offline Mode" process of FIG. 26 in greater detail.

FIG. 28 is a flow diagram illustrating the process "Run Offline Mode" 544 of FIG. 26 in greater detail. Process 544 begins at 562 and, in an operation 564, it is determined whether an connection to the Cybergym server has come online. If so, the process is completed at 566, such that the process 468B of FIG. 26 can run an online mode 542. Otherwise, the process 544 continues to run in the offline mode and, in an operation 568, the process iterates over the exercise devices and the buffer data. Next, in an operation 570, it process the buffers in local mode. Finally, in an operation 572, the process iterates over the exercise device and transmit data. Process control is then returned to operation 564.

As will be apparent to those skilled in the art, as it is used herein "iterate" means that the system is going through the roster device by device or buffer by buffer in an iterative fashion. That is, from a starting point, it first processes the device or buffer associated with that starting point, and then the point is iterated (typically by 1) to process the next device or buffer in the roster or other list. When the end of the roster or list is reached, it may be started again from the beginning in a circular fashion.

Figures 29, 30:
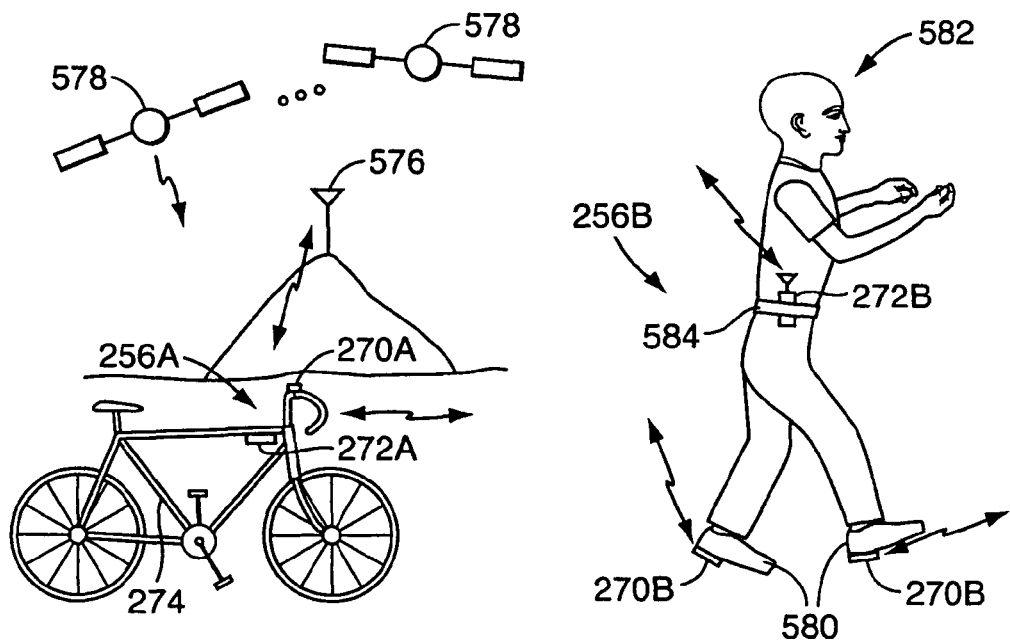
FIG. 29 illustrates a first implementation of a mobile local server.
FIG. 30 is an illustration of a second local server of FIG. 13.

FIG. 29 is an illustration of a mobile local system. More particularly, the mobile local system has a mobile exercise device controller 270A and a mobile local server 272A, which may be coupled together in an either wired or not wired fashion. Still alternatively, the devices 270A and 272A can be coupled together by the frame of the bicycle 274 or otherwise. It is quite common for bicycles to be provided with bicycle "computers" which provide such indication as speed, RPM, altitude, etc. The mobile exercise controller 270A would take over this functionality as well as providing the functionality of the exercise device controller 280. The mobile local server 272A would have essentially the same functionality as the fixed server illustrated with reference to FIG. 21, except that it preferably is a more "stripped-down" version, not including the options of the hard disk, graphics accelerator, and out-of-band transceiver. Also, lower power consumption devices would typically be used, and the connection to the Internet is by radio modem from an included antenna.

The mobile system illustrated in FIG. 9 can be in two-way communication via, for example, a cellular telephone system 576. Alternatively, radio modem services such as formerly provided by Ricochet, would be another communication methodology. While the server 272A could conceivably service a number of control units 270A, it is likely to be dedicated solely to that control unit. This is because bicyclists may not always be in sufficient proximity for the units 270A to communicate with a single server 272A and, in fact, bicycles that are in close proximity may not want to share the same server 272A. Exceptions include such situations as group races or competitions, such as the Tour de France. In such an instance, a server 272A could be in a pace car, which would service a number of controllers associated with individual bicycles.

The server 272A is also preferably included with a variety of sensor inputs, including GPS from multiple satellites 578, altimeter readings based on, for example, atmospheric pressure or, alternatively calculated from GPS information, inclinometers, etc. In this fashion, a mobile exercise device user can interact with a remote server, a trainer, or compete against other mobile and/or fixed exercise devices. For example, a user can be riding the bicycle while data such as distance, speed, RPM, elevation gain, etc., are transmitted to the remote server and provided to the trainer. The trainer can then download scripts or programs to the unit 270A indicating that a user should pick up the pace, shift to a lower gear, etc. Furthermore, out-of-band communications can also occur with the trainer, for example, by cellular telephone connection. The mobile exercisers can also compete and interact with fixed exercisers, again with some scaling and/or handicapping.

FIG. 30 is an illustration of yet another form of mobile local system 256B. More particularly, sensors and transmitters can be provided in the shoes 580 of a runner 582 which communicate with a mobile local server 272B attached to the belt 584 of the runner 582. For reasons similar to those discussed before, it is preferable that there be a one-to-one correspondence between the mobile units 270B and the mobile local server 272B. As was the case discussed with reference to FIG. 29, the mobile local server 272B can communicate with the Internet via a variety of channels, including radio modem channels, cellular phone channels, etc. The local mobile server 272B also preferably has multiple sensoring modes, including GPS. Similar sensors can be provided for other sports and activities such as weight lifting, swimming, etc.

As indicated above, the mobile interactive local systems allow a user (athlete) to at least upload data via the Internet and, preferably, download information. While the "in-band" bandwidth may be somewhat limited in certain embodiments, it can be augmented without a band communications as well. In addition to allowing the recording of exercise parameters on the Cybergym server and interacting with a Cybergym trainer, the mobile exercise devices permit competitions, even against different classes of exercise devices. For example, with a suitable handicap, a runner can race against a cyclist who may be competing with someone on a stationary rowing machine. This also permits amateurs (presumably on fixed exercise devices) to compete with professionals on mobile exercise devices. Furthermore, "virtual worlds" can be created with which one or more users can interact. In one scenario, each user can be represented by a spaceship which can "fly" through space, have dogfights, etc. based upon the use of the exercise devices and optional in-band or out of band controllers.

Figure 31:
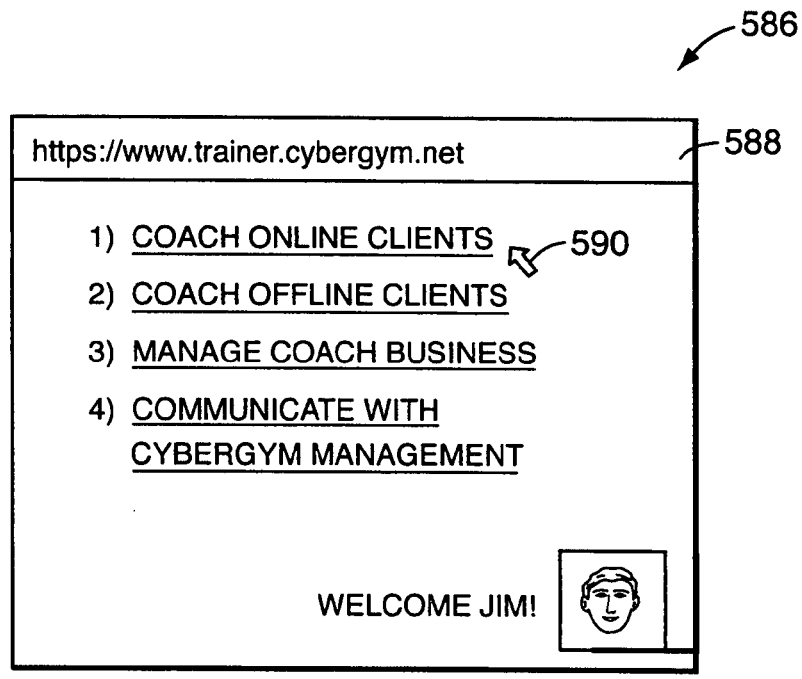
FIG. 31 illustrates a web page that may be displayed on a trainer machine of FIG. 13.

FIG. 31 illustrates a possible screen that can be displayed on the personal computer system 262A of a trainer 276A. As described previously, in a preferred embodiment of the present invention, the computational functionality with respect to the trainer machine 264A is provided by the Cybergym server 258. Therefore, the trainer 276A needs only to install a network browser on his trainer machine 262A to enjoy full functionality of the system 250. In this instance, the trainer 276A point to his browser to a URL 588, namely https://www.trainer.Cybergym.net. This brought up the display allowing the trainer to choose from a number of options. For example, the trainer can choose option: 1) coach online clients; 2) coach offline clients; 3) manage his or her coaching business; and, 4) communicate with Cybergym management. As is well known to those skilled in the art, the trainer 276A can select one of these options with a pointer 590 controlled by a pointing device such as a mouse or trackball. The trainer 276A then "clicks" on the pointer 590 by depressing the button on the mouse or trackball to select the appropriate next screen. It should be noted that these communications are all secured and encrypted, and are run over an https://connection.

Figure 32:
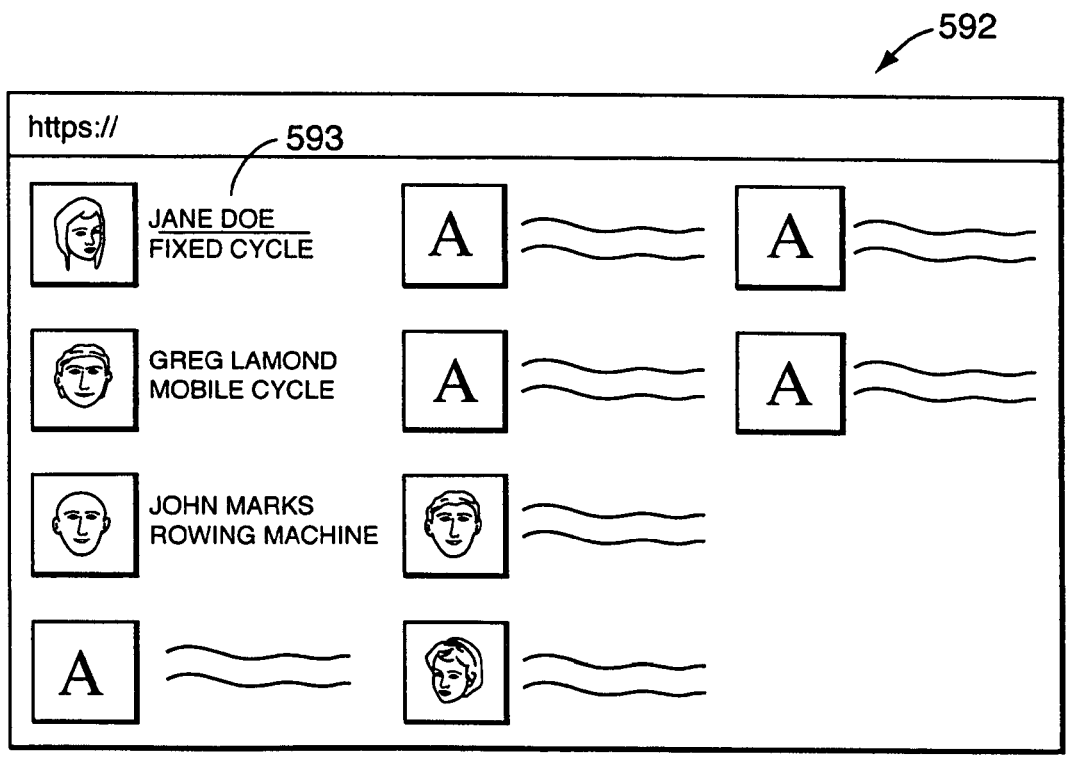
FIG. 32 illustrates another web page which may be displayed on the trainer machine for coaching online clients.

FIG. 32 illustrates a screen 592 which can be accessed by selecting the "Coach Online Clients" option from the list on screen 586. This is again a secure connection and it indicates all of the users in the group belonging to trainer 276A that are currently online. If the user has a exercise device provided with a video camera, the image of the user is displayed on the screen as shown. If the user is not working with an exercise device equipped with a video camera, and "A" is provided in place of his or her image to indicate that they are riding anonymously, at least in the visual sense. Preferably, the trainer 276A also has a trainer machine 262A that is provided with a video camera which would allow his or her image to be displayed at the exercise device, as long as it was provided with sufficient out-of-band devices. Of course, as the capability of in-band transmission increases, this information may also be transmitted to the user via an in-band connection, as described above.

Figure 33:
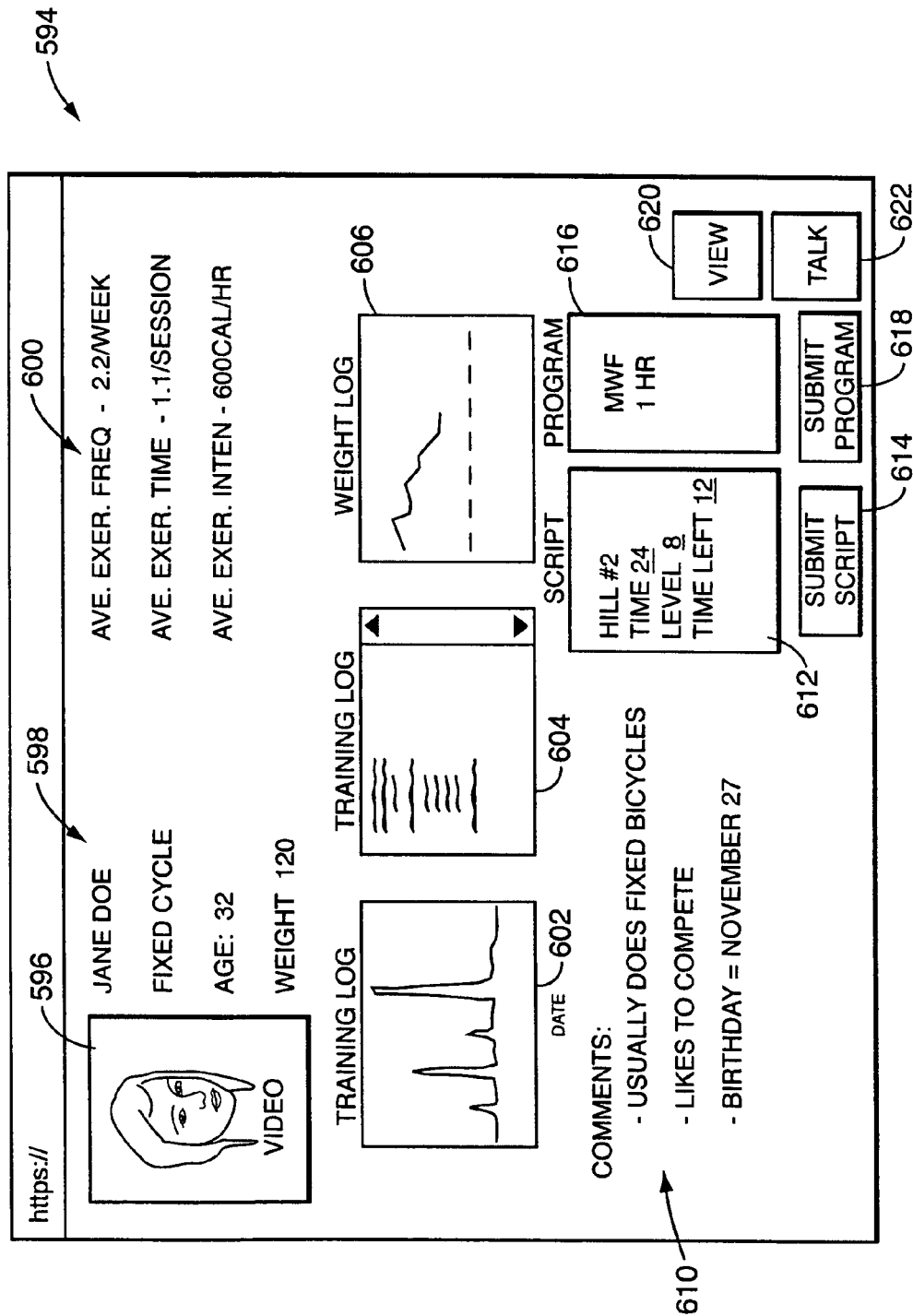
FIG. 33 is a web page that can be viewed on a trainer machine for coaching an individual client.

FIG. 33 illustrates a screen 594 which was accessed by selecting the user Jane Doe at 593. This provides a full screen of information specifically about the user Jane Doe. The screen 594 can include a video portion 596, basic information 598 about the user, information 600 concerning her exercise program, a variety of graphs and charts 602, 604, and 606 illustrating various parameters of her exercise history, and a comments field 610. The screen 594 also preferably displays a display of the current script 612 running on the device while allowing the trainer to modify it and submit it back to the device by means of a on-screen button 614. Similarly, the screen 594 also preferably includes a program window 616 which allows the trainer to view and modify the overall program for the user Jane Doe and to submit it by the on-screen button 618 to the user exercise device. An on-screen button 620 permits the trainer's camera to be toggled on and off and an on-screen button 622 permits a microphone to be switched on and off so that the trainer can either talk or not be heard by the user.

Figure 34:
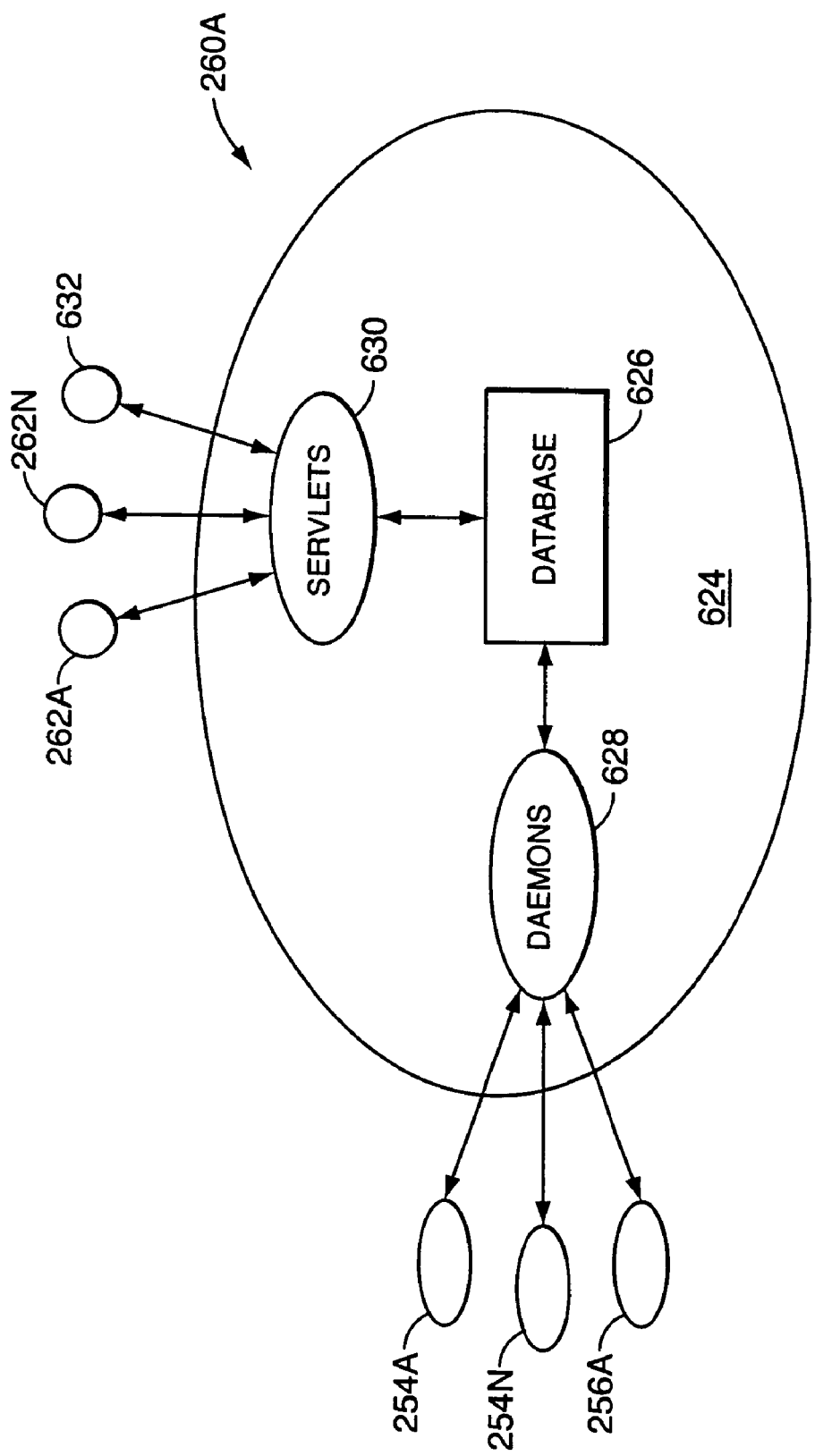
FIG. 34 is an illustration of a CYBERGYM server of the present invention.

In FIG. 34, a CYBERGYM server 260A is described in greater detail. As will be appreciated by those skilled in the art, a server 260A includes a hardware component and a software component. The hardware component (not show) is typically a personal computer, workstation, network server, etc. Sometimes it is implemented as a "virtual machine" wherein a number of logical machines are implemented on a single hardware machine. The software component 624 provides the functionality of the Cybergym system.

Software component 624 is based upon a database 626 which is used to store and retrieve information, programs (scripts), graphics, video, telemetry, and other data used in performance of the Cybergym system. This database is preferably provided as a relational database, such as is provided by Oracle Corporation of Redwood Shores, Calif.

Communicating with the database 626 are daemons 628 and servlets 630. The purpose of the daemons is to service the local servers, such as servers 254A, 254N and 256A, at least partially through the Internet, or other Wide Area Network (WAN). The purpose of the servlets is to is to service the trainer machines, such as trainer machines 262A and 262N, as well as any personal computer or "workstation" 632 used by a user. As is well known to those skilled in the art, servlets are often used to provide web-based interfaces to database driven web sites.

Figure 35:
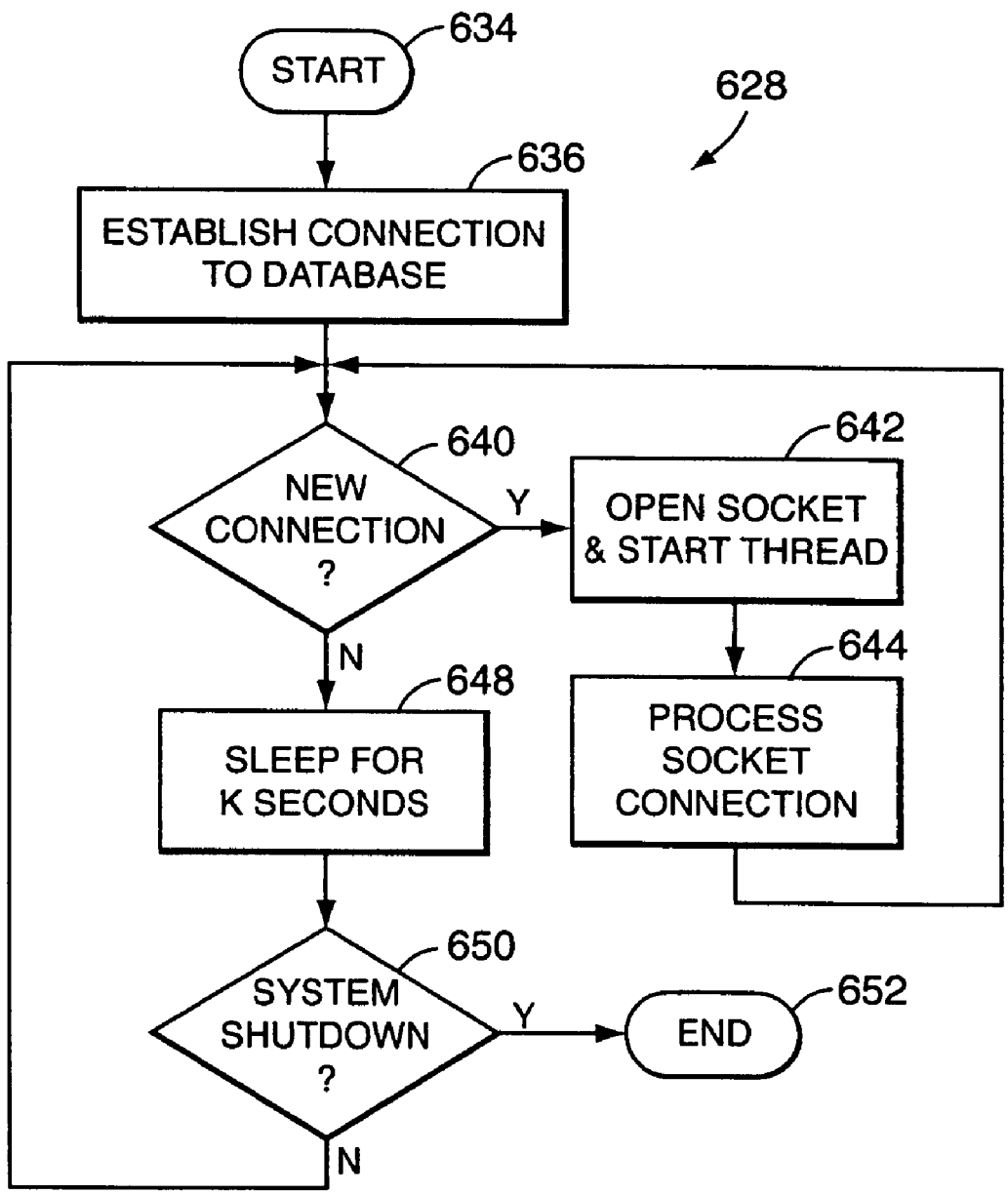
FIG. 35 is a flow diagram illustrating the operation of the daemon of FIG. 34 in greater detail.

FIG. 35 illustrates the daemon 628 of FIG. 34 in greater detail. Daemon 628 begins at 634 and, in an operation 636, establishes a connection to the database 626. Next, in an operation 640, it determines whether there is a new connection with a local server. If so, an operation 642 opens a socket to communicate with a local server (such as local server 266A or 272A), and starts a new "thread." As is well known to those skilled in the art, a "thread" is a new process which operates asynchronously from its parent process (i.e. daemon 628).

Next, in an operation 644, the socket connection made by operation 642 is processed. Process control then returns to operation 640.

If operation 640 does not detect a new connection, then the daemon is put to "sleep" for a period of time k seconds, e.g. k=1-5 seconds. After the period of time has elapsed, an operation 650 determines if there is a system shutdown. If so, the operation of the daemon 628 ends at 652. Otherwise, process control is again returned to operation 640.

Figure 36:
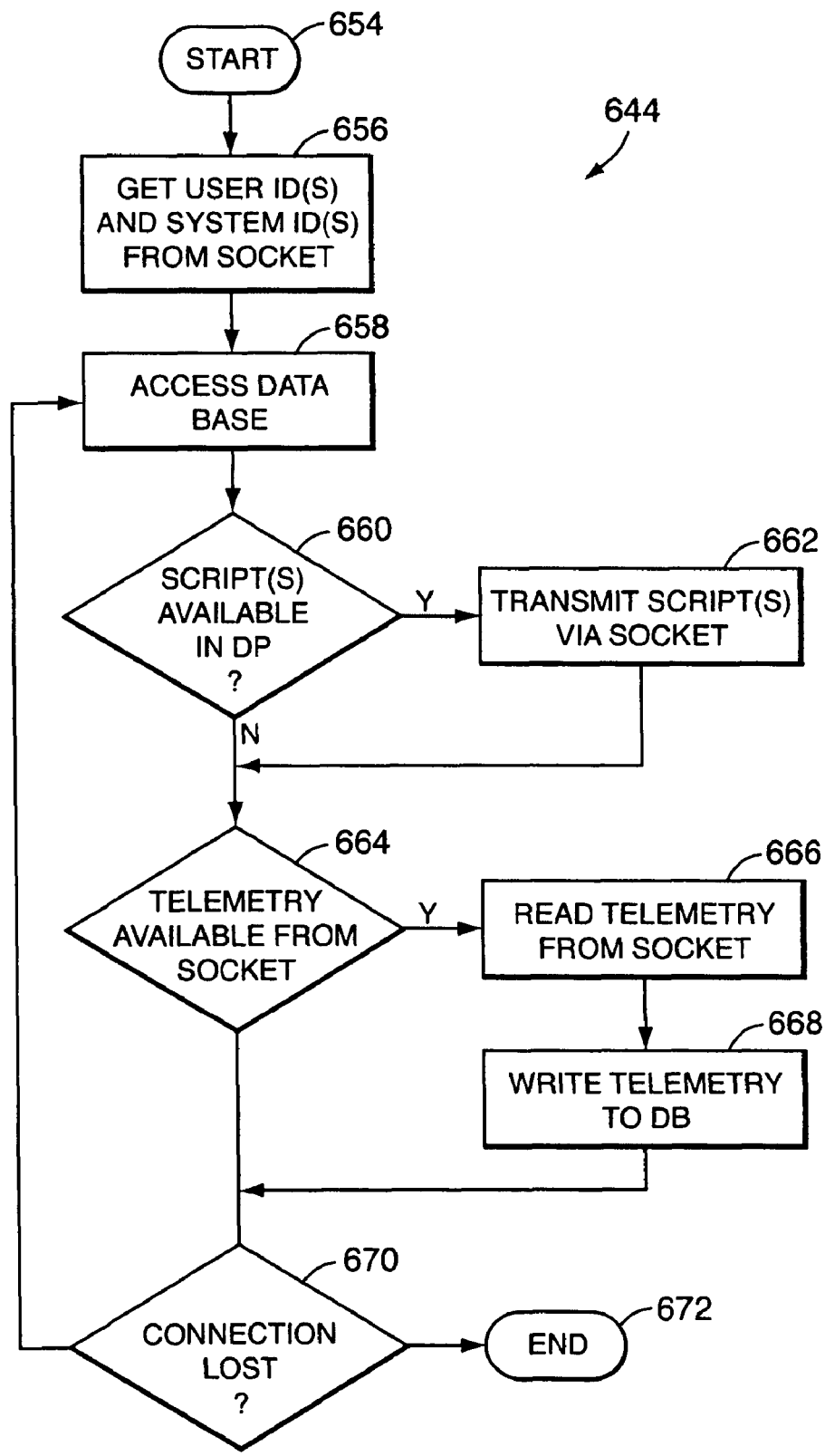
FIG. 36 is a flow diagram illustrating the "Process Socket Connection" operation of FIG. 34 in greater detail.

FIG. 36 illustrates the process "Process Socket Connection" 644 of FIG. 35 in greater detail. Process 644 begins at 654 and, in an operation 656, the user ID(s) and system ID(s) are obtained from the socket that was created by operation 642. Next, in an operation 658, the data base is accessed to obtain any scripts or other data or programs that are to be sent to the local servers. Operation 660 determines if there are any scripts available and, if so, they are transmitted to the local server via the socket in an operation 662. If there is telemetry or other data communication available from the socket as determined by an operation 664, the telemetry and/or other data communication is read from the socket in an operation 666 and is written to the database in an operation 668. An operation 670 then determines whether the connection has been lost, at which time the process is terminated at 672. Otherwise, process control is returned to operation 658 to continue the processing.

Figure 37:
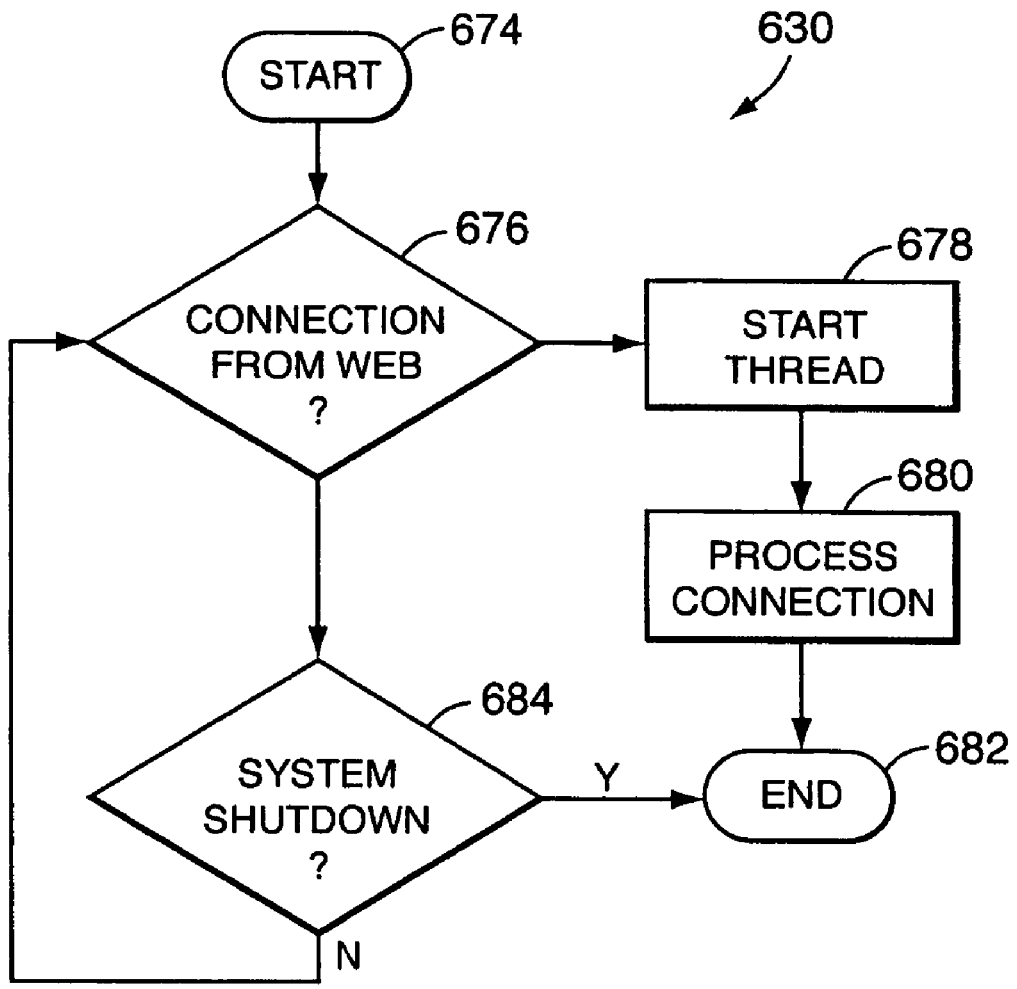
FIG. 37 is a flow diagram illustrating the servlet process of FIG. 34 in greater detail.

FIG. 37 is a flow diagram illustrating the servlet process 630 in greater detail. The servlet 630 begins at 674 and, in an operation 676 it is determined if there is a "connection" from the web. By "connection" it is meant that a connection or "request" has been sent from an Internet enabled machine to the server 260A. Upon the receipt of the request from, for example, a trainer at a trainer machine 262A or a user at a personal computer 632, the operation will recognize the desired connection and, in an operation 678, will start a new thread next, in an operation 680 the connection is processed, and the servlet will have completed its process at 682. If a connection from the web is not recognized by operation 676, an operation will determine if there has been a system shutdown. If so, the servlet is again completed at 682. Otherwise, process control is returned to operation 676 to again look for a connection from the web.

Figure 38:
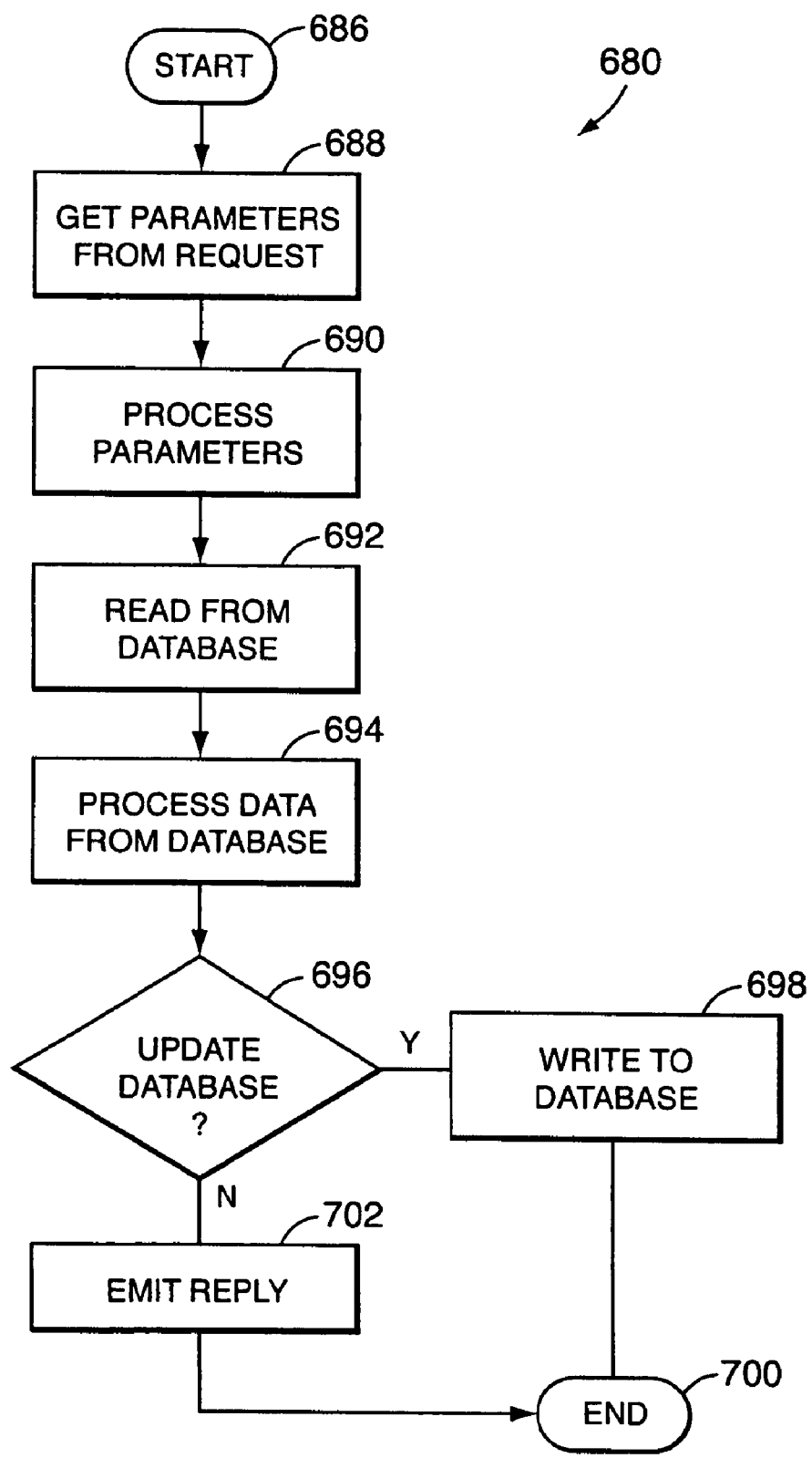
FIG. 38 is a flow diagram illustrating the "Process Connection" operation of FIG. 37 in greater detail.

FIG. 38 illustrates the process "Process Connection" 680 of FIG. 37 in greater detail. The process 580 begins at 686 and, in an operation 688, parameters are received from the request that came with the connection. Next, the parameters are processed in an operation 690. For example, if the trainer or user specified a request for information concerning a specific exercise session, it might be necessary to transform the name of the person received in the request into a user ID. Next, in an operation 692, the data, program, graphic, video, etc. ("information") required to fulfill the request is read from the database 692. Next, the information is processed in an operation 694. An operation 696 determines whether the database should be updated, based on the request type. For example, some requests merely interrogate the database for information, while others require the storage of information in the database. If the database is to be updated, an operation 698 writes to the database and the process 680 ends at 700. Otherwise, an operation 702 transmits the reply back to the requestor, and the process again ends at 700.

It will therefore be appreciated that in a preferred embodiment of the present invention, a distributed wide area network (WAN) such as the Internet is used to couple local servers, remote servers, and workstations together. Users at local systems can interact visually and even in a tactile manner with other users over the Internet. For example, a first user at a first local station can take a "virtual ride" with another user at a second local station through the Internet connection. Likewise, a remote "personal trainer" can interact with a user at a local station via the Internet communication linkage. The present invention therefore allow group exercise experiences, even when a user is physically alone.

While this invention has been described in terms of several preferred embodiments, it is contemplated that alternatives, modifications, permutations and equivalents thereof will become apparent to those skilled in the art upon a reading of the specification and study of the drawings. It is therefore intended that the following appended claims be interpreted as including all such alternatives, modifications, permutations and equivalents as fall within the true spirit and scope of the present invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An exercise system comprising:
a mobile exercise system including mobile exercise equipment and at least one exercise monitoring sensor coupled to said mobile exercise equipment for monitoring at least one operating parameter of said mobile exercise equipment, wherein use of said mobile exercise equipment results in physical travel of a user and said mobile exercise equipment over a substantial distance, said mobile exercise system at least temporarily storing exercise activity data developed from said at least one sensor in digital memory, said mobile exercise system being capable of wirelessly communicating said exercise activity data;
a mobile communication system separate from said mobile exercise system, said mobile communication system being adapted to wirelessly receive said exercise activity data from said mobile exercise system, said mobile communication system also being adapted to communicate said exercise activity data over a network; and
a remote server coupled to said network for selectively receiving and storing said exercise activity data in a computer-readable media.

2. An exercise system as recited in claim 1, wherein said mobile exercise system includes a mobile unit associated with a user, and wherein said at least one exercise monitoring sensor is associated with said mobile unit.

3. An exercise system as recited in claim 2, wherein said mobile unit is at least one of attached, carried, and worn by a user.

4. An exercise system as recited in claim 3, wherein said mobile unit is at least temporarily attached to apparel of said user.

5. An exercise system as recited in claim 4, wherein said apparel includes at least one of clothing and athletic gear.

6. An exercise system as recited in claim 5, wherein said athletic gear includes at least one of foot mounted and head mounted gear.

7. An exercise system as recited in claim 1, wherein said mobile unit is associated with said mobile exercise equipment used by said user.

8. An exercise system as recited in claim 7, wherein said mobile unit is attached to said mobile exercise equipment.

9. An exercise system as recited in claim 2, wherein said mobile communication system is associated with a pacer car.

10. An exercise system as recited in claim 1, wherein said mobile exercise system includes a mobile unit and said mobile communication system include a mobile server.

11. An exercise system as recited in claim 10, wherein said mobile unit and said mobile server are in wireless communication with each other.

12. An exercise system as recited in claim 10, wherein said mobile server is in wireless communication with said remote server.

13. An exercise system as recited in claim 10, wherein said mobile server is associated with a pacer car.

14. An exercise system as recited in claim 10, wherein said mobile server is associated with said mobile exercise equipment used by said user.

15. An exercise system comprising:
a mobile exercise device having at least one operating parameter that can be varied during use of said mobile exercise device, wherein use of said mobile exercise device results in physical travel of said mobile exercise device over a substantial distance;
mobile means coupled to said mobile exercise device for monitoring at least one operating parameter of said mobile exercise device during use thereof and developing exercise activity data therefrom, said mobile means being capable of wirelessly communicating said exercise activity data;
a mobile communication system separate from said mobile exercise device and said mobile means, said mobile communication system being adapted to wirelessly receive said exercise activity data from said mobile means, said mobile communication system also being adapted to communicate said exercise activity data over a network; and
server means coupled to said network for selectively receiving and storing said exercise activity data.

16. An exercise system comprising:
a mobile local system including:
a mobile exercise device having a sensor adapted to monitor and gather information about various parameters of the mobile exercise device, the mobile exercise device being adapted to wirelessly communicate the information about the various parameters of the mobile exercise device; and
a mobile communication system separate from said mobile exercise device, said mobile communication system being adapted to wirelessly receive the information about the various parameters of the mobile exercise device from the mobile exercise device, the mobile communication system also being adapted to communicate the information about the various parameters of the mobile exercise device over a wide area network;
a fixed local system including a fixed exercise device having an actuator adapted to alter various parameters of the fixed exercise device; and
a communications network adapted to enable the mobile local system to communicate with the fixed local system, the actuator of the fixed exercise device being adapted to adjust the parameters of the fixed exercise device to simulate the parameters of the mobile exercise device based on the information gathered by the sensor of the mobile exercise device and communicated to the fixed local system over the communications network.

17. In association with an exercise system for conducting a virtual competition between a plurality of users of the exercise system, the exercise system including a first local system comprising a first local exercise device and a second local system comprising a second local exercise device, the first and second local systems being adapted to track data about the use of the respective first and second local exercise devices, an exercise system server for facilitating the virtual competition, the exercise system server being adapted to:
(i) regulate and monitor the virtual competition between the plurality of users,
(ii) receive and process the data about the use of the first and second local exercise devices, the processing of the data by the exercise system server including handicapping the data if the first and second local exercise devices are different types of exercise devices.

18. An interactive exercise system, comprising:
a remote server adapted to communicate with a communications network;
a trainer machine adapted to communicate with the remote server via the communications network;
a plurality of fixed local systems adapted to communicate with the remote server via the communications network, each of the plurality of fixed local systems comprising:
a fixed local server adapted to communicate with the communications network; and
a fixed exercise device having a sensor adapted to process and send data to the remote server via the fixed local server and the communications network, and an actuator adapted to influence various parameters of the fixed exercise device;
a mobile local system adapted to communicate with the remote server via the communications network, the mobile local system comprising:
a mobile local server adapted to communicate with the communications network, the mobile local server being disposed in a mobile vehicle; and
a mobile exercise device separate from the mobile local server and the mobile vehicle, the mobile exercise device having a sensor adapted to monitor and gather information about various parameters of the mobile exercise device and wirelessly send the information to the mobile local server in the mobile vehicle for communication to the remote server via the communications network.

19. An exercise system server for use in connection with a mobile exercise unit and a fixed exercise unit, wherein the exercise system server receives mobile exercise activity data and fixed exercise activity data relating respectively to the use of the mobile exercise unit and the fixed exercise unit, wherein the exercise system server stores the mobile and fixed exercise activity data, and wherein the exercise system server processes the mobile and fixed exercise activity data by comparing the mobile and fixed exercise activity data and scaling the mobile or fixed exercise activity data based on differences between the mobile exercise unit and the fixed exercise unit.

20. An exercise system server that receives: (i) mobile exercise activity data relating to the use of a mobile exercise device; and (ii) local exercise activity data relating to the use of a local exercise device, wherein the exercise system server processes and handicaps the mobile and local exercise activity data by scaling the mobile exercise activity data or the local exercise activity data to account for: (i) the mobile and local exercise devices being different types of exercise devices; (ii) differences in operating parameters of the mobile and local exercise devices, or (iii) differences in environmental conditions at the mobile exercise device and the local exercise device.

* * * * *

UNITED STATES PATENT AND TRADEMARK OFFICE
CERTIFICATE OF CORRECTION

| | | |
|---|---|---|
| PATENT NO. | : 7,857,731 B2 | Page 1 of 2 |
| APPLICATION NO. | : 12/489031 | |
| DATED | : December 28, 2010 | |
| INVENTOR(S) | : Hickman et al. | |

It is certified that error appears in the above-identified patent and that said Letters Patent is hereby corrected as shown below:

On Title Page
Page 4
OTHER PUBLICATIONS, change ""Precor and Netpulse partner to
   Create the World's First Internet Powered Elliptical." Netpulse press release, Oct. 1, 2999" to
   --"Precor and Netpulse partner to
   Create the World's First Internet Powered Elliptical." Netpulse press release, Oct. 1, 1999--

Column 7
Line 33, after "58" insert --,--

Column 8
Line 27, change "system" to --systems--

Column 10
Line 43, change "be modifiable" to --modifiable--

Column 12
Line 38, change "pick it up" to --pick up--
Line 40, change "line was free" to --line is free--

Column 13
Line 47, change "the" to --them--

Column 14
Line 21, change "Internet, is" to --Internet, it is--
Line 31, change "from variety" to --from a variety--

Column 15
Line 27, change "a "frame" a video" to --A "Frame" of a video--

Signed and Sealed this
Seventh Day of June, 2011

David J. Kappos
*Director of the United States Patent and Trademark Office*

Column 16
Line 52, change "266A" to --226A--

Column 18
Line 8, change "operated" to --operate--

Column 19
Line 65, change "EPROM 312" to --EPROM 310--

Column 20
Line 31, change "266A" to --226A--
Line 37, change "an user" to --a user--
Line 39, change "unanimous" to --ananymous--

Column 23
Line 17, change "34" to --434--

Column 24
Line 56, change "has" to --have--

Column 26
Line 2, change "596" to --496--
Line 15, change "process" to --processes--
Line 22, change "buffer" to --buffers--

Column 27
Line 28, change "without a band" to --with out-of-band--
Line 51, change "point to his" to --points his--

Column 28
Line 52, change "is to is to" to --is to--